(12) United States Patent
Shapiro et al.

(10) Patent No.: US 11,400,168 B2
(45) Date of Patent: Aug. 2, 2022

(54) METHODS AND SYSTEMS FOR NONINVASIVE CONTROL OF BRAIN CELLS AND RELATED VECTORS AND COMPOSITIONS

(71) Applicant: CALIFORNIA INSTITUTE OF TECHNOLOGY, Pasadena, CA (US)

(72) Inventors: Mikhail G. Shapiro, Los Angeles, CA (US); Jerzy O Szablowski, Valley Village, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 99 days.

(21) Appl. No.: 16/213,991

(22) Filed: Dec. 7, 2018

(65) Prior Publication Data

US 2019/0175763 A1 Jun. 13, 2019

Related U.S. Application Data

(60) Provisional application No. 62/595,893, filed on Dec. 7, 2017.

(51) Int. Cl.
| | | |
|---|---|---|
| *A61K 48/00* | (2006.01) | |
| *A61P 21/00* | (2006.01) | |
| *C12N 15/113* | (2010.01) | |
| *A61M 37/00* | (2006.01) | |
| *A61N 7/00* | (2006.01) | |
| *A61K 38/17* | (2006.01) | |
| *A61K 9/00* | (2006.01) | |

(52) U.S. Cl.
CPC ........ *A61K 48/0058* (2013.01); *A61K 9/0019* (2013.01); *A61K 38/1709* (2013.01); *A61K 48/0016* (2013.01); *A61K 48/0025* (2013.01); *A61K 48/0066* (2013.01); *A61K 48/0075* (2013.01); *A61K 48/0083* (2013.01); *A61M 37/00* (2013.01); *A61N 7/00* (2013.01); *A61P 21/00* (2018.01); *C12N 15/113* (2013.01); *A61N 2007/003* (2013.01); *A61N 2007/0021* (2013.01); *A61N 2007/0039* (2013.01)

(58) Field of Classification Search
None
See application file for complete search history.

(56) References Cited

U.S. PATENT DOCUMENTS

| | | | |
|---|---|---|---|
| 2004/0049134 A1 | 3/2004 | Tosaya et al. | |
| 2014/0288421 A1* | 9/2014 | Shapiro | A61B 8/481 600/431 |
| 2018/0139954 A1* | 5/2018 | Tsukamoto | A01N 25/02 |
| 2019/0060400 A1* | 2/2019 | During | A61K 45/06 |

FOREIGN PATENT DOCUMENTS

| | | |
|---|---|---|
| WO | 2017/049252 A1 | 3/2017 |
| WO | 2017/097853 A1 | 6/2017 |
| WO | 2019/113538 A2 | 6/2019 |

OTHER PUBLICATIONS

Chu "Focused Ultrasound-Induced Blood-Brain Barrier Opening: Association with Mechanical Index and Cavitation Index Analyzed" Scientific Reports | 6:33264 (Year: 2016).*
Roth "DREADDs for Neuroscientists" Neuron 89 (Year: 2016).*
Jax "Body Weight Information for C57BL/6J (000664)" accessed from jax.org on Sep. 21, 2021 (Year: 2021).*
Kakava "An Intersectional Approach to Target Neural Circuits With Cell- and Projection-Type Specificity: Validation in the Mesolimbic dopamine system" Frontiers in Molecular Neuroscience Feb. 2019 | vol. 12 | Article 49 (Year: 2019).*
Schwarz "Viral-genetic tracing of the input-output organization of a central noradrenaline circuit" N AT U R E| vol. 524| Aug. 6, 2015 (Year: 2015).*
Adkison, K.D. and D.D. Shen, "Uptake of valproic acid into rat brain is mediated by a medium-chain fatty acid transporter." *Journal of Pharmacology and Experimental Therapeutics*, 1996. 276(3): p. 1189.
Airan, R.D., et al., "Noninvasive Targeted Transcranial Neuromodulation via Focused Ultrasound Gated Drug Release from Nanoemulsions." *Nano Letters*, 2017. 17(2): p. 652-659.
Akil, H., et al., "The Future of Psychiatric Research: Genomes and Neural Circuits." *Science*, 2010. 327(5973): p. 1580.
Alexander, G.M., et al., Remote control of neuronal activity in transgenic mice expressing evolved G protein-coupled receptors. Neuron, 2009. 63(1): p. 27-39.
Alonso, A., et al., "Focal Delivery of AAV2/1-transgenes Into the Rat Brain by Localized Ultrasound-induced BBB Opening." *Molecular therapy. Nucleic acids*, 2013. 2(2): p. e73-e73.
Apkarian, A.V., J.A. Hashmi, and M.N. Baliki, Pain and the brain: specificity and plasticity of the brain in clinical chronic pain. Pain, 2011. 152(3 Suppl): p. S49.
Armbruster, B.N., et al., Evolving the lock to fit the key to create a family of G protein-coupled receptors potently activated by an inertligand. Proc Natl Acad Sci U S A, 2007. 104(12): p. 5163-8.
Aschauer, D.F. et al., "Analysis of transduction efficiency, tropism and axonal transport of AAV serotypes 1,2, 5, 6, 8 and 9 in the mouse brain." *PLoS One*, 2013. 8(9): p. e76310.
Badea, A. et al., "Morphometric analysis of the C57BL/6J mouse brain." Neuroimage, 2007. 37(3): p. 683-93.
Banks, W.A., "Characteristics of compounds that cross the blood-brain barrier." *BMC neurology*, 2009. 9 Suppl 1(Suppl 1): p. S3-S3.
Banks, W.A., Peptides and the blood-brain barrier. Peptides, 2015. 72: p. 16-19.
Barar, J., et al., Blood-brain barrier transport machineries and targeted therapy of brain diseases. Bio Impacts : BI, 2016. 6(4): p. 225-248.

(Continued)

*Primary Examiner* — Adam Weidner
(74) *Attorney, Agent, or Firm* — Steinfl + Bruno, LLP

(57) ABSTRACT

Provided herein are methods, systems, and related vectors and compositions allowing for noninvasive control of neural circuits. In particular, the methods and systems herein described utilize acoustically targeted chemogenetics to achieve a noninvasive neuromodulation in specifically selected cell-types among spatially selected brain regions.

19 Claims, 15 Drawing Sheets

(56) References Cited

OTHER PUBLICATIONS

Baseri, B., et al., "Multi-modality safety assessment of blood-brain barrier opening using focused ultrasound and definity microbubbles: a short-term study." *Ultrasound Med Biol*, 2010. 36(9): p. 1445-59.
Bender, E., Gene therapy: Industrial strength. Nature, 2016. 537: p. S57.
Bernal-Casas, D., et al., "Studying Brain Circuit Function with Dynamic Causal Modeling for Optogenetic fMRI." *Neuron*, 2017. 93(3): p. 522-532.e5.
Betke, K.M., C.A. Wells, and H.E. Hamm, GPCR mediated regulation of synaptic transmission. Progress in neuro biology, 2012. 96(3): p. 304-321.
Blanchard, D.C. et al., "Ethoexperimental approaches to the biology of emotion." *Annu Rev Psychol*, 1988. 39: p. 43-68.
Burgess, A., et al., "Alzheimer disease in a mouse model: MR imaging-guided focused ultrasound targeted to the hippocampus opens the blood-brain barrier and improves pathologic abnormalities and behavior." *Radiology*, 2014. 273(3): p. 736-45.
Burgess, A., et al., "Therapeutic effects of focused ultrasound-mediated blood-brain barrier opening in a mouse model of Alzheimer's disease." *Journal of Therapeutic Ultrasound*, 2015. 3(Suppl 1): p. O16-O16.
Camerino, D.C. et al., "Ion channel pharmacology." *Neurotherapeutics*, 2007. 4(2): p. 184-98.
Carpentier, A., et al., Clinical trial of blood-brain barrier disruption by pulsed ultrasound. Sci Transl Med, 2016. 8(343): p. 343re2.
Castle, M.J., et al., "Controlling AAV Tropism in the Nervous System with Natural and Engineered Capsids" *Methods Mol Biol*, 2016. 1382: p. 133-49.
Cendes, F., et al., "Neuroimaging of epilepsy. Handbook of clinical neurology", 2016. 136: p. 985-1014.
Chan, K.Y., et al., "Engineered AAVs for efficient noninvasive gene delivery to the central and peripheral nervous systems." *Nat Neurosci*, 2017. 20(8): p. 1172-1179.
Chen, H. et al., "The size of blood-brain barrier opening induced by focused ultrasound is dictated by the acoustic pressure." *Journal of Cerebral Blood Flow & Metabolism*, 2014. 34(7): p. 1197-1204.
Chen, R., et al., "Wireless magnetothermal deep brain stimulation." *Science*, 2015. 347(6229): p. 1477-80.
Choi, J.J., et al., "Noninvasive and localized neuronal delivery using short ultrasonic pulses and microbubbles." *Proceedings of the National Academy of Sciences*, 2011. 108(40): p. 16539.
Choi, J.J., et al., "Noninvasive,transcranial and localized opening of the blood-brain barrier using focused ultrasound in mice." *Ultrasound Med Biol*, 2007. 33(1): p. 95-104.
Deffieux, T., et al., "Low-intensity focused ultrasound modulates monkey visuomotor behavior." *Current Biology*, 2013. 23(23): p. 2430-2433.
Deng, L., et al., "A multi-frequency sparse hemispherical ultrasound phased array for microbubble-mediated transcranial therapy and simultaneous cavitation mapping." *Phys Med Biol*61, 8476-8501 (2016).
Deverman, B.E., et al., "Cre-dependent selection yields AAV variants for widespread gene transfer to the adult brain." *Nat Biotechnol*, 2016. 34(2): p. 204-9.
DiMattia, M.A., et al., "Structural Insight into the Unique Properties of Adeno-Associated Virus Serotype 9." *Journal of Virology*, 2012. 86(12): p. 6947-6958.
Dittgen, T., et al., "Lentivirus-based genetic manipulations of cortical neurons and their optical and electrophysiological monitoring in vivo." *Proc Natl Acad Sci U S A*, 2004. 101(52): p. 18206-11.
Dobrakowski, P.P. et al. "MR-guided focused ultrasound: a new generation treatment of Parkinson's disease, essential tremor and neuropathic pain." *Interv Neuroradiol*20, 275-282(2014).
Downs, M.E. et al. "Long-Term Safety of Repeated Blood-Brain Barrier Opening via Focused Ultrasound with Microbubbles in Non-Human Primates Performing a Cognitive Task" (vol. 10,e0125911, 2015). *PLOS One*10 (2015).
Duyn, J. et al., "Magnetic resonance imaging of neural circuits." *Nature clinical practice. Cardiovascular medicine*, 2008. 5 Suppl 2(Suppl 2): p. S71-S78.
Eldridge, M.A.G., et al., Chemogenetic disconnection of monkey orbitofrontal and rhinal cortex reversibly disrupts reward value. Nature Neuroscience, 2015. 19: p. 37.
Elias, W.J. et al. "A Randomized Trial of Focused Ultrasound Thalamotomy for Essential Tremor." *N Engl J Med*375, 730-739 (2016).
Eliava, M., et al., "A New Population of Parvocellular Oxytocin Neurons Controlling Magnocellular Neuron Activity and Inflammatory Pain Processing." *Neuron*, 2016. 89(6): p. 1291-1304.
English, J.G. and B.L. Roth, Chemogenetics—a transformational and translational platform. JAMA Neurology, 2015. 72(11): p. 1361-1366.
Ginn, S.L., et al., Gene therapy clinical trials worldwide to 2012 an update. Journal of Gene Medicine, 2013. 15(2): p. 65-77.
Gomez, J.L., et al., "Chemogenetics revealed: DREADD occupancy and activation via converted clozapine." *Science*, 2017. 357(6350): p. 503.
Gossen, M. et al., "Tight control of gene expression in mammalian cells by tetracycline-responsive promoters." *Proc Natl Acad Sci U S A*, 1992. 89(12): p. 5547-51.
Grippo, R.M., et al., "Direct Midbrain Dopamine Input to the Suprachiasmatic Nucleus Accelerates Circadian Entrainment." *Curr Biol*, 2017. 27(16): p. 2465-2475.e3.
Heffner, C.S., et al., "Supporting conditional mouse mutagenesis with a comprehensive cre characterization resource." *Nat Commun*, 2012. 3: p. 1218.
Hirtz, D., et al., "How common are the "common" neurologic disorders?" *Neurology*, 2007. 68(5): p. 326-37.
Hsu, P.-H., et al., "Noninvasive and Targeted Gene Delivery into the Brain Using Microbubble-Facilitated Focused Ultrasound." *PLOS ONE*, 2013. 8(2): p. e57682.
https://en.wikipedia.org/wiki/Brain Feb. 17, 2020.
https://en.wikipedia.org/wiki/Neuron Feb. 17, 2020.
https://en.wikipedia.org/wiki/Receptor_activated_solely_by_a_synthetic, Nov. 4, 2018 2 pages.
Huang, Q., et al., Effective Gene Transfer into Central Nervous System Following Ultrasound-Microbubbles-Induced Opening of the Blood-Brain Barrier. Ultrasound in Medicine & Biology, 2012. 38(7): p. 1234-1243.
Hynynen, K. et al., "Image-guided ultrasound phased arrays are a disruptive technology for non-invasive therapy." *Phys Med Biol*61, R206-248 (2016).
Hynynen, K. et al., "Noninvasive MR imaging-guided focal opening of the blood-brain barrier in rabbits." *Radiology*220, 640-646(2001).
International Preliminary Report on Patentability for International Application No. PCT/US2018/064605 filed on Dec. 7, 2018 on behalf of California Institute of Technology. dated Jun. 18, 2020. 8 pages.
Ji B. et al., "Multimodal Imaging for DREADD-Expressing Neurons in Living Brain and Their Application to Implantation of iPSC-Derived Neural Progenitors" *The Journal of Neuroscience*,Nov. 2016, 15 pages.
Johnson, G.A., et al., "Waxholmspace: an image-based reference for coordinating mouse brain research." *Neuroimage*,2010. 53(2): p. 365-72.
Kheirbek, M.A., et al., "Differential control of learning and anxiety along the dorsoventral axis of the dentate gyrus." *Neuron*,2013. 77(5): p. 955-68.
Kim, K.M., et al., "Optogenetic mimicry of the transient activation of dopamine neurons by natural reward is sufficient for operant reinforcement." *PLoS One*,2012. 7(4): p. e33612.
King, R.L., et al., "Effective parameters for ultrasound-induced in vivo neurostimulation." *Ultrasound in medicine & biology*,2013. 39(2): p. 312-331.
Kobus, T. et al., "Safety Validation of Repeated Blood-Brain Barrier Disruption Using Focused Ultrasound." *Ultrasound in Medicine & Biology*(2015).
Koch, M., et al., "Hypothalamic POMC neurons promote cannabinoid-induced feeding." *Nature*,2015. 519(7541): p. 45-50.

(56) References Cited

OTHER PUBLICATIONS

Konofagou E. et al., "Ultrasound-Induced Blood-Brain Barrier Opening" *Curr Pharm Biotechnol*,Jun. 2012, 27 pages.

Koob, G.F. and N.D. Volkow, Neurocircuitry of addiction. Neuropsychopharmacology, 2009. 35(1): p. 217-238.

Kotterman, M.A., T.W. Chalberg, and D.V. Schaffer, Viral Vectors for Gene Therapy: Translational and Clinical Outlook.Annu Rev Biomed Eng,2015. 17: p. 63-89.

Lambert, D.G., "Drugs and receptors." *Continuing Education in Anaesthesia Critical Care & Pain*,2004. 4(6). p. 181-184.

Landhuis, E., "Ultrasound for the brain." *Nature*2017. 551: p. 257-259.

Lein, E.S., et al., "Genome-wide atlas of gene expression in the adult mouse brain." *Nature*,2007. 445(7124): p. 168-76.

Leinenga, G. et al., "Scanning ultrasound removes amyloid-beta and restores memory in an Alzheimer's disease mouse model." *Sci Transl Med*,2015. 7(278). p. 278ra33.

Libby, L.A. et al., "fMRI as a measure of cognition related brain circuitry in schizophrenia." *Current topics in behavioral neurosciences*,2012. 11: p. 253-267.

Lindeberg, J., et al., "Transgenic expression of Cre recombinase from the tyrosine hydroxylase locus." *Genesis*,2004. 40(2): p. 67-73.

Lipsman N. et al., "Blood-brain barrier opening in Alzheimer's disease using MR-guided focused ultrasound" *Nature Communications*,2018. 8 pages.

Luo, L. et al., "Genetic Dissection of Neural Circuits." *Neuron*,2008. 57(5): p. 634-660.

Magnus, C.J., et al., Chemical and genetic engineering of selective ligand-ion channel interactions. Science (New York, N.Y.), 2011. 333(6047): p. 1292-1296.

Mahler, S.V., et al., "Designer receptors show role for ventral pallidum input to ventral tegmental area in cocaine seeking." 2014. 17(4): p. 577-85.

Majka, P., et al., "Common atlas format and 3D brain atlas reconstructor: infrastructure for constructing 3D brain atlases." *Neuroinformatics*,2012. 10(2): p. 181-97.

McDannold, N., et al., "Targeted, noninvasive blockade of cortical neuronal activity." *Scientific reports*,2015. 5.

McDannold N. "Temporary disruption of the blood-brain barrier by use of ultrasound and microbubbles: safety and efficacy evaluation in rhesus macaques" *Cancer Research*,Jul. 2012, 22 pages.

Mehić, E., et al., "Increased anatomical specificity of neuro modulation via modulated focused ultrasound." *PLoS One*,2014. 9(2): p. e86939.

Mendell, J.R., et al., Single-Dose Gene-Replacement Therapy for Spinal Muscular Atrophy. New England Journal of Medicine, 2017. 377(18): p. 1713-1722.

Mooney, S.J., et al., "Focused Ultrasound-Induced Neurogenesis Requires an Increase in Blood-Brain Barrier Permeability." *PLoS One*,2016. 11(7): p. e0159892.

*National-Institutes-of-Mental-Health*, "The Numbers Count: Mental Disorders in America." http://www.lb7.uscourts.gov/documents/12-cv-1072url2.pdf.

Nomoto M. et al., "Cellular tagging as a neural network mechanism for behavioral tagging" *Nature Communications*,Aug. 2016, 11 pages.

O'Reilly, M.A. et al., "Ultrasound enhanced drug delivery to the brain and central nervous system." *Intl J Hyperthermia*28, 386-396(2012).

Pangalos, M.N. et al., "Drug development for CNS disorders:strategies for balancing risk and reducing attrition." *Nat Rev Drug Discov*,2007. 6(7): p. 521-32.

Pardridge, W.M., Drug transport across the blood-brain barrier. Journal of cerebral blood flow and metabolism : official journal of the International Society of Cerebral Blood Flow and Metabolism, 2012. 32(11): p. 1959-1972.

Pardridge, W.M., The blood-brain barrier: bottleneck in brain drug development. NeuroRx : the journal of the American Society for Experimental Neuro Therapeutics, 2005. 2(1): p. 3-14.

Pignataro D. et al., "Adeno-Associated Viral Vectors Serotype 8 for Cell-Specific Delivery of Therapeutic Genes in the Central Nervous System" *Frontiers in Neuroanatomy*,Feb. 2017, 13 pages.

Plummer, C. et al., "EEG source localization in focal epilepsy:where are we now?" *Epilepsia*,2008. 49(2): p. 201-18.

Rangarajan, S., et al., AAV5-Factor VIII Gene Transfer in Severe HemophiliaA. New England Journal of Medicine, 2017.

Ressler, K.J. and H.S. Mayberg, Targeting abnormal neural circuits in mood and anxiety disorders: from the laboratory to the clinic. Nature Neuroscience, 2007. 10: p. 1116.

Roth B., "DREADDs for Neuroscientists" *Neuron*,Feb. 2016, 25 pages.

Russell, S., et al., Efficacy and safety of voretigene neparvovec (AAV2-hRPE65v2) in patients with RPE65-mediated inherited retinal dystrophy: a randomised, controlled, open-label, phase 3 trial. Lancet, 2017. 390(10097): p. 849-860.

Russo, S.J. and E.J. Nestler, The brain reward circuitry in mood disorders. Nature Reviews Neuroscience, 2013. 14(9): p. 609-625.

Sakurai, T., The role of orexin in motivated behaviours. Nature Reviews Neuroscience, 2014.

Samiotaki, G. et al., "Enhanced delivery and bioactivity of the neurturin neurotrophic factor through focused ultrasound-mediated blood-brain barrier opening in vivo." *Journal of Cereb Blood Flow Metab*35, 611-622(2015).

Sananbenesi, F., et al., "A hippocampal Cdk5 pathway regulates extinction of contextual fear." *Nat Neurosci*,2007. 10(8): p. 1012-9.

Sato, T. et al., "Ultrasonic Neuro modulation Causes Widespread Cortical Activation via an Indirect Auditory Mechanism." *bioRxiv*,2017.

Shapiro, M.G., et al., "Unparalleled control of neural activity using orthogonal pharmacogenetics." *ACS Chem Neurosci*3, 619-629(2012).

Sheikov, N., et al., Cellular mechanisms ofthe blood-brain barrier opening induced by ultrasound in presence of microbubbles. Ultrasound Med Biol, 2004. 30(7): p. 979-89.

Shin, L.M. and I. Liberzon, The neuro circuitry of fear, stress, and anxiety disorders. Neuropsychopharmacology, 2009. 35(1): p. 169-191.

Slimko, E.M., et al., Selective electrical silencing of mammalian neurons in vitro by the use of invertebrate ligand-gated chloride channels. J Neurosci, 2002. 22(17): p. 7373-9.

Smith, K.S., et al., DREADDs: Use and Application in Behavioral Neuroscience. Behavioral neuroscience. 2016. 130(2): p. 137-155.

Song, K.H., et al., "Microbubble gas volume: A unifying dose parameter in blood-brain barrier opening by focused ultrasound." *Theranostics*,2017. 7(1): p. 144-152.

Sternson, S.M. et al., "Chemogenetic tools to interrogate brain functions." *Annual review of neuroscience*37, 387-407(2014).

Sun T. et al., "Closed-loop control of targeted ultrasound drug delivery across the blood-brain/tumor barriers in a rat glioma model", *PNAS Epub.*,Nov. 2017, pp. E10281-E10290.

Szablowski, J.O., et al., "Acoustically targeted chemogenetics for the non-invasive control of neural circuits." *Nature Biomedical Engineering*, 2018. 2(7): p. 475-484.

Tarini, M. et al., "Ambient occlusion and edge cueing to enhance real time molecular visualization." *IEEE Transactions on Visualization and Computer Graphics*,2006. 12(5): p. 1237-1244.

Thompson, K.J. et al., DREADD Agonist21 Is an Effective Agonist for Muscarinic-Based DREADDs in Vitro and in Vivo. ACS Pharmacol. Transl. Sci., 2018. 1(1): p. 12.

Thomsen, G.M., et al., Delayed Disease Onsetand Extended Survival in the SOD1(G93A) Rat Model of Amyotrophic Lateral Sclerosis after Suppression of Mutant SOD1 in the Motor Cortex. The Journal of Neuro science, 2014. 34(47): p. 15587-15600.

Thévenot, E., et al., "Targeted delivery of self-complementary adeno-associated virus serotype 9 to the brain, using magnetic resonance imaging-guided focused ultrasound." *Human gene therapy*,2012. 23(11): p. 1144-1155.

Tinberg, C.E., et al., Computational design of ligand-binding proteins with high affinity and selectivity. Nature, 2013. 501(7466): p. 212-216.

Treat, L.H. et al. "Targeted delivery of doxorubicin to the rat brain at therapeutic levels using MRI-guided focused ultrasound." *Int J Cancer*121, 901-907(2007).

(56) References Cited

OTHER PUBLICATIONS

Tufail, Y., et al., "Transcranial pulsed ultrasound stimulates intact brain circuits." *Neuron*,2010. 66(5): p. 681-694.

Tung, Y.S., et al., "In vivo transcranial cavitation threshold detection during ultrasound-induced bloodbrain barrier opening in mice." *Phys Med Biol*,2010. 55(20): p. 6141-55.

Tung, Y.S. et al., "The mechanism of interaction between focused ultrasound and micro bubbles in blood-brain barrier opening in mice." *Journal of the Acoustical Society of America*130, 3059-3067(2011).

Tye, K.M. et al., "Optogenetic investigation of neural circuits underlying brain disease in animal models." *Nature Reviews Neuroscience*,2012. 13: p. 251.

Tyler, W.J. et al., "Ultrasonic modulation of neural circuit activity." *Current Opinion in Neurobiology*,2018. 50: p. 222-231.

VanElzakker, M.B., et al., "From Pavlov to PTSD: the extinction of conditioned fear in rodents, humans, and anxiety disorders." *Neurobiol Learn Mem*,2014. 113: p. 3-18.

Wang, D.S., et al., Cationic versus neutral microbubbles for ultrasound-mediated gene delivery in cancer. Radiology, 2012. 264(3): p. 721-732.

Wang, K.S. et al., "Using fMRI to study reward processing in humans: past, present, and future." *Journal of neurophysiology*,2016. 115(3): p. 1664-1678.

Wang, S., et al., "Microbubble Type and Distribution Dependence of Focused Ultrasound induced Blood Brain Barrier Opening." *Ultrasound in medicine & biology*,2014. 40(1): p. 130-137.

Wang, S., et al., "Non-invasive, Focused Ultrasound-Facilitated Gene Delivery for Optogenetics." *Scientific Reports*,2017. 7: p. 39955.

Wang, S., et al., "Noninvasive, neuron-specific gene therapy can be facilitated by focused ultrasound and recombinant adeno-associated virus." *Gene therapy*,2015. 22(1): p. 104-110.

Watakabe, A., et al., "Comparative analyses of adeno-associated viral vector serotypes 1, 2, 5, 8 and 9 in marmoset, mouse and macaque cerebral cortex." *Neuroscience Research*,2015. 93: p. 144-157.

Whissell P.D. et al., "The use of DREADDs to deconstruct behavior", Frontiers in Genetics,2016, vol. 7, pp. 1-15.

Whitaker, A.M. et al., "Animal models of post-traumatic stress disorder and recent neurobiological insights." *Behav Pharmacol*,2014. 25(5-6): p. 398-409.

Zhu, H., et al., "Chemogenetic inactivation of ventral hippocampal glutamatergic neurons disrupts consolidation of contextual fear memory." *Neuropsychopharmacology*,2014. 39(8): p. 1880-92.

Zincarelli, C., et al., "Analysis of AAV Serotypes 1-9 Mediated Gene Expression and Tropism in Mice After Systemic Injection." *Molecular Therapy*,2008. 16(6): p. 1073-1080.

International Search Report and Written Opinion for International Application No. PCT/US2018/064605 filed on Dec. 7, 2018 on behalf of California Institute of Technology dated May 24, 2019 12 pages.

* cited by examiner

METHODS AND SYSTEMS FOR NONINVASIVE CONTROL OF BRAIN CELLS AND RELATED VECTORS AND COMPOSITIONS

CROSS-REFERENCE TO RELATED APPLICATION

The present application claims priority to U.S. Provisional Application No. 62/595,893, entitled "Acoustically Targeted Chemogenetics" filed on Dec. 7, 2017, the contents of which is incorporated by reference in its entirety.

FIELD

The present disclosure relates to methods and systems for control of brain cells and related vectors and compositions. In particular, the methods and systems and related vectors and composition can be directed to provide non-invasive control of brains cells and related neural circuits and/or used to treat and/or prevent conditions associated with dysfunctions of neural circuits.

BACKGROUND

Dysfunctions of neural circuits can occur in individuals and are often associated with various neurological and psychiatric conditions wherein dysfunctions are typically found in specific spatial locations and cell types [1-5].

Conventional pharmacological treatments for such diseases are as specific as they typically act throughout the entire brain. Conversely surgical treatments are able to target specific parts of the brain for excision or electrical stimulation. Surgical treatments however require invasive approaches, leading to significant tissue damage and increasing the risk of complications. In addition, surgical treatments leading to a permanent change in the brain structure, such as resection or ablation, lack reversibility and temporal dose control.

As a consequence, development of approaches to neuromodulation which enable spatial, cell-type and temporal control of neural circuits as well as correction of related dysfunctions (with particular reference to dysfunction associated with neurological and psychiatric conditions) without the need for surgical treatment is still challenging.

SUMMARY

Provided herein are methods, systems, and related vectors and compositions which in several embodiments, allow spatial, cell-type and/or temporal stimulation of target brain cell of a neural circuit of an individual without need of a surgical treatment.

In particular, the methods and systems herein described are based on the use of a chemogenetic protein configured to activate or inhibit, when in an operative state, the activity of a target brain cell with respect to a neural circuit of an individual, in combination with a chemical actuator configured to switch the chemogenetic protein conformation into the operative state, upon binding with the chemogenetic protein, the combined use performed to specifically and/or selectively activate or inhibit the target brain cell activity and in preferred embodiments, to modify an existing behavior and/or physiology of the individual associated with the target brain cell activity, through the specific and/or selective activation or inhibition of the target brain cell of the target circuit.

In particular, according to a first aspect a method and system are described to control a target brain cell activity with respect to a target neural circuit of an individual.

The method comprises applying focused ultrasound to a target brain region of the individual the target brain region comprising the target brain cell, and systemically administering to the individual an effective amount of microbubble contrast agents. In the method, the applying focused ultrasound and the systematically administering microbubble contrast agent is performed to induce transient blood-brain barrier opening at the target brain region.

The method also comprises before, simultaneously, in combination with, or after applying focused ultrasound, systemically administering to the individual an effective amount of an expression vector configured to enter the brain at the transient blood-brain barrier opening and to specifically deliver and express in the target brain cells a gene encoding a chemogenetic protein under control of a promoter configured to be active in the target brain cell, the chemogenetic protein configured to activate or inhibit the target brain cell activity following binding with a corresponding chemical actuator or metabolite thereof.

In the method, the applying, the systemically administering an effective amount of microbubble contrast agents and the systemically administering an effective amount of an expression vector are performed to deliver and express the gene encoding a chemogenetic protein in a controlled percentage population of the target brain cell in the target brain region to obtain a chemogenetically treated target brain region in which target brain cells of the controlled percentage population comprise the chemogenetic protein.

The method further comprises systemically administering to the individual the corresponding chemical actuator, to allow binding of the corresponding chemical actuator or a metabolite thereof with the chemogenetic protein in the target brain cells of the controlled population of the chemogenetically treated target brain region, and activation or inhibition of the target brain cell activity.

In preferred embodiments, the controlled percentage population is at least 40%, and more preferably at least 50%.

The system comprises at least the expression vector configured to enter the brain at a transient blood-brain barrier opening and to specifically deliver and express in the target brain cells a gene encoding the chemogenetic protein under control of a promoter configured to be active in the target brain cell, the microbubble contrast agent and a chemical actuator configured to activate the chemogenetic protein through direct binding to the chemogenetic protein of the chemical actuator or of a metabolite thereof, for simultaneous combined or sequential use in the method to control a target brain cell activity herein described.

According to a second aspect a method and system are described to modify a target behavior or physiological function of an individual associated with a target brain cell activity with respect to a neural circuit of the individual.

The method comprises applying focused ultrasound to a target brain region of the individual the target brain region comprising the target brain cell, and systemically administering to the individual an effective amount of microbubble contrast agents. In the method, the applying focused ultrasound and the systematically administering microbubble contrast agent is performed to induce transient blood-brain barrier opening at the target brain region.

The method also comprises before, simultaneously, in combination with or after applying focused ultrasound, systemically administering to the individual an effective amount of an expression vector configured to enter the brain at the transient blood-brain barrier opening and to specifically deliver and express in the target brain cells a gene encoding a chemogenetic protein under control of a promoter configured to be active in the target brain cell, the chemogenetic protein configured to activate or inhibit the target brain cell activity following binding with a corresponding chemical actuator or metabolite thereof to modify the target behavior or physiological function of an individual.

In the method, the applying, the systemically administering an effective amount of a microbubble contrast agent and the systemically administering an effective amount of an expression vector are performed to deliver and express the gene encoding a chemogenetic protein in a controlled percentage population of the target brain cell in the target brain region associate with the target behavior or physiological function, and to obtain a chemogenetically treated target brain region in which the controlled percentage population of the target brain cell comprises the chemogenetic protein.

The method further comprises systemically administering to the individual the corresponding chemical actuator, to allow binding of the corresponding chemical actuator or a metabolite thereof with the chemogenetic protein in the controlled percentage population of the target brain cell of the chemogenetically treated target brain region, to modify the target behavior or physiological function of the individual.

In preferred embodiments, the controlled percentage population is preferably at least 40% and more preferably at least 50%.

The system comprises at least the expression vector configured to enter the brain at a transient blood-brain barrier opening and to specifically deliver and express in the target brain cells a gene encoding the chemogenetic protein under control of a promoter configured to be active in the target brain cell, the microbubble contrast agent and a chemical actuator configured to activate the chemogenetic protein through direct binding to the chemogenetic protein of the chemical actuator or of a metabolite thereof, for simultaneous, combined or sequential use in the method to modify a target behavior or physiological function of an individual herein described.

According to a third aspect, a method and system are described for treating or preventing in an individual a condition associated with a target brain cell activity with respect to a neural circuit of the individual.

The method comprises applying focused ultrasound to a target brain region of the individual the target brain region comprising the target brain cell, and systemically administering to the individual an effective amount of microbubble contrast agents. In the method, the applying focused ultrasound and the systematically administering microbubble contrast agent is performed to induce transient blood-brain barrier opening at the target brain region.

The method also comprises before, simultaneously, in combination with or after applying focused ultrasound, systemically administering to the individual an effective amount of an expression vector configured to enter the brain at the transient blood-brain barrier opening and to specifically deliver and express in the target brain cells a gene encoding a chemogenetic protein under control of a promoter configured to be active in the target brain cell, the chemogenetic protein configured to activate or inhibit the target brain cell activity following binding with a corresponding chemical actuator or metabolite thereof to treat or prevent the condition in the individual.

In the method, the applying, the systemically administering an effective amount of microbubble contrast agents and the systemically administering an effective amount of an expression vector are performed to deliver and express the gene encoding a chemogenetic protein in a controlled percentage population of the target brain cell in the target brain region, the controlled percentage population associated with the treating or preventing of the condition in the individual, and to obtain a chemogenetically treated target brain region in which target brain cells of the controlled percentage population comprise the chemogenetic protein.

The method further comprises systemically administering to the individual the corresponding chemical actuator, to allow binding of the corresponding chemical actuator or a metabolite thereof with the chemogenetic protein in the target brain cells of the controlled population of the chemogenetically treated target brain region, thus treating or preventing the condition in the individual.

In preferred embodiments, the controlled percentage population is at least 40%, more preferably at least 50%.

The system comprises a pharmaceutical composition comprising the expression vector configured to express the gene encoding for the chemogenetic protein in a target brain cell and a pharmaceutically acceptable vehicle. The system further comprises a pharmaceutical composition comprising a chemical actuator configured to activate the chemogenetic protein through direct binding to the chemogenetic protein of the chemical actuator or of a metabolite thereof, for combined or sequential use in the method to treat or prevent in an individual a neurological condition of the individual herein described.

Methods and systems herein described and related vectors and compositions allow in several embodiments to perform specific and/or selective activation of one or more target brain cell of neural circuits without the need of surgery or other invasive procedures.

In particular, methods and systems herein described and related vectors and compositions allow in several embodiments achievement of a temporal, cell and spatial selectivity in activation of target brain cells previously only achievable with a direct intracranial injection of gene delivery vectors, Accordingly, methods and systems herein described and related vectors and compositions allow in several embodiments to perform neuromodulation of neural circuits through selective stimulation of specific types of target brain cells performed without need of surgery or other invasive procedures and in particular without the need for permanently attached or implanted devices for chronic use.

Methods and systems herein described and related vectors and compositions allow in several embodiments to perform neuromodulation of neural circuits among spatially selected target brain regions without the need of surgery or other invasive procedures, and without the need for permanently attached or implanted devices for chronic use. In particular in some embodiments, the spatially selected brain regions can have millimeter sizes.

Methods and systems herein described and related vectors and compositions allow in several embodiments to perform noninvasive neuromodulation of neural circuits without a need for multiple acoustic treatments as instead required by known methods (up to dozens in larger species[6, 7]).

Methods and systems herein described and related vectors and compositions allow in several embodiments to achieve non-invasive neuromodulation with spatial precision, cell-type precision, molecular pathway precision and temporal precision.

Methods and systems herein described and related vectors and compositions allow in several embodiments to achieve non-invasive neuromodulation through stimulation of specific pathways in the target brain cell.

In view of the above methods and systems herein described and related vectors and compositions allow in several embodiments a specific and selective activation or inhibition of excitatory neurons in selectively targeted brain areas and in particular regions involved in memory formation and volitional behavior and implicated in several neuropathologies, including the hippocampus and midbrain.

Furthermore, compared to invasive and surgical procedure, methods and systems herein described and related vectors and compositions allow in several embodiments to comprehensively transduce selected regions or an entire brain region in a single session with relatively minimal tissue disruption or damage even in locations deep within the brain while providing spatial selectivity. The methods and systems can also achieve neuromodulation without the need for permanently attached or implanted devices for chronic use.

The methods and systems herein described and related vectors and compositions can be used in connection with various applications wherein control of neural circuits is desired. For example, methods and systems herein described and related vectors and compositions can be used to treat individuals for neurological or psychiatric conditions associated with the activation or inhibition of one or more neural circuits in an individual. Additional exemplary applications include uses of the methods and systems herein described and related vectors and compositions in several fields including basic biology research, applied biology, bio-engineering, medical research with particular reference to study of neurological and psychiatric disease mechanisms, related therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 1, Panel (b) provides a schematic exemplary illustration of the ATAC sequence, the blood-brain barrier (BBB) is opened locally using focused ultrasound, and systemically injected adeno-associated virus (AAV) encoding a designer receptor exclusively activated by designer drug (DREADD) enters the treated area. After several weeks, (the DREADD is expressed in the targeted region in cells possessing selected promoter activity. At any desired subsequent time, the DREADD-expressing neurons can be excited or inhibited through a chemogenetic drug such as clozapine-n-oxide (CNO).

FIG. 2 Panel (a) shows a rendering of mouse brain with hippocampus highlighted in red and targeted locations of the center of FUS-BBBO beams indicated with grey circles. The selected renderings are an anatomical representation of the hippocampus in MRI images below. Panels show, from left to right: isometric view of the brain, axial view of the brain, followed by rendered slices including dorsal, and then ventral hippocampus. FIG. 2 Panel (b) shows images from a representative T1-weighted MRI scan acquired immediately after FUS-BBBO, with brighter areas indicating relaxation enhancement from Prohance extravasation, as shown by arrowheads. Representative of n=24 mice analyzed. Scale bars 2 mm. FIG. 2 Panel (c) shows images of representative brain sections from a single animal showing dorsal (top) and ventral (bottom) hippocampus immunostained for hM4Di-mCherry 6 weeks after FUS-BBBO and injection of AAV9 encoding this hM4Di-mCherry under the CaMKIIa promoter. The DAPI stain demarcates cell nuclei. Representative of n=4 independent brains analyzed. Scale bar, 500 µm. FIG. 2 Panel (d) shows magnified views of the dorsal (top) and ventral (bottom) hippocampus showing widespread expression in molecular layers (MO) of the dentate gyrus, stratum orens (SO), subiculum (SU), granular (SG) and pyramidal cell layers of hippocampus (SP). Representative of n=4 independent brains analyzed. Scale bar, 200 µm. FIG. 2 Panel (e) shows representative immunostaining result for hM4Di-mCherry in a mouse that received the same viral construct, but did not undergo FUS-BBBO. Representative of n=3 independent brains analyzed. Scale bar, 500 µm.

FIG. 3 Panel (a) shows a chart reporting the percentage of cells bodies with detectable mCherry fluorescence in pyramidal layers of the hippocampus and overlaying FUS-targeted cortex, following an exemplary DREADD administration according to methods herein described with thalamus as an untargeted negative control. These values serve as a measure of relative transduction efficiency in different fields of hippocampus. The letters v and d indicate ventral and dorsal sites, respectively. n=5 mice; one-way ANOVA test compared to thalamus, $F_{(9, 40)}$=13.89; **, p=8.7E-10, with Tukey-HSD post-hoc test. FIG. 3 Panel (b) shows representative images of mCherry fluorescence in each field for the exemplary administration of FIG. 3 Panel (a). The DAPI stain marks cell nuclei. Representative of n=6 mice. Scale bars represent 100 µm. FIG. 3 Panel (c) shows representative co-immunostaining for hM4Di-mCherry and CaMKIIa following an exemplary DREADD administration according to methods herein described. Arrowheads indicate cells positive for CaMKIIa. Representative of n=6 mice. FIG. 3 Panel (d) shows representative co-immunostaining for hM4Di-mCherry and Gad1 following an exemplary DREADD administration according to methods herein described. Arrowheads indicate cells positive for Gad1. (e) Percentage of DREADD-expressing cells in the CA2 region that are positively stained for CaMKIIa or Gad1, representing excitatory and inhibitory cells, respectively. n=6 mice; p=4.75E-

9, two-tailed t-test assuming unequal variance. Scale bars in c-d are 50 μm. Bar graphs represent the mean±SEM.

Figure 4:
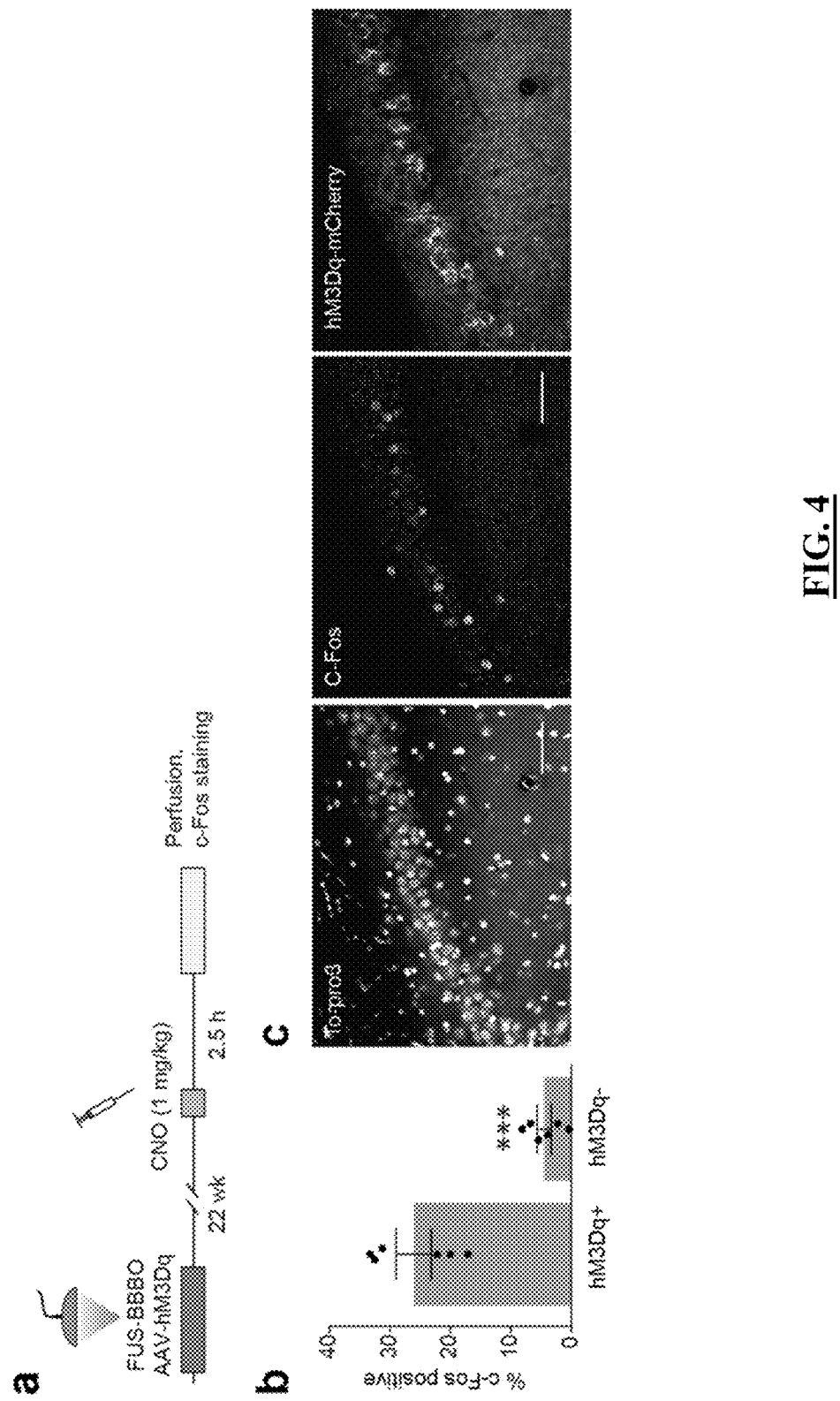

FIG. 4 shows graphs and an image illustrating neuronal activation by an exemplary ATAC method with excitatory DREADDs. In particular, FIG. 4 Panel (a) shows a schematic illustration an exemplary excitatory DREADD activation protocol. FUS-BBBO and an IV injection of AAVs was followed by a period of expression, and an IP injection of CNO in saline (1 mg/kg). 2.5 hours later, mice were perfused and their brains were extracted for histological evaluation. FIG. 4 Panel (b) shows a diagram illustrating fraction of cells in the CA3 field of the hippocampus staining positively for c-Fos after CNO administration, as a function of whether the cells are positive or negative for hM3Dq-mCherry. (***, p=7.1E-4, two tailed t-test, assuming unequal variance, n=6 independently targeted hemispheres in n=3 mice). FIG. 4 Panel (c) shows a representative immunohistology image of CA3 with c-Fos, hM3Dq-mCherry and nucleus (To-pro3) staining. n=6 independently targeted hemispheres analyzed from n=3 mice. Scale bar, 50 μm. Bar graphs represent the mean±SEM.

Figure 5:
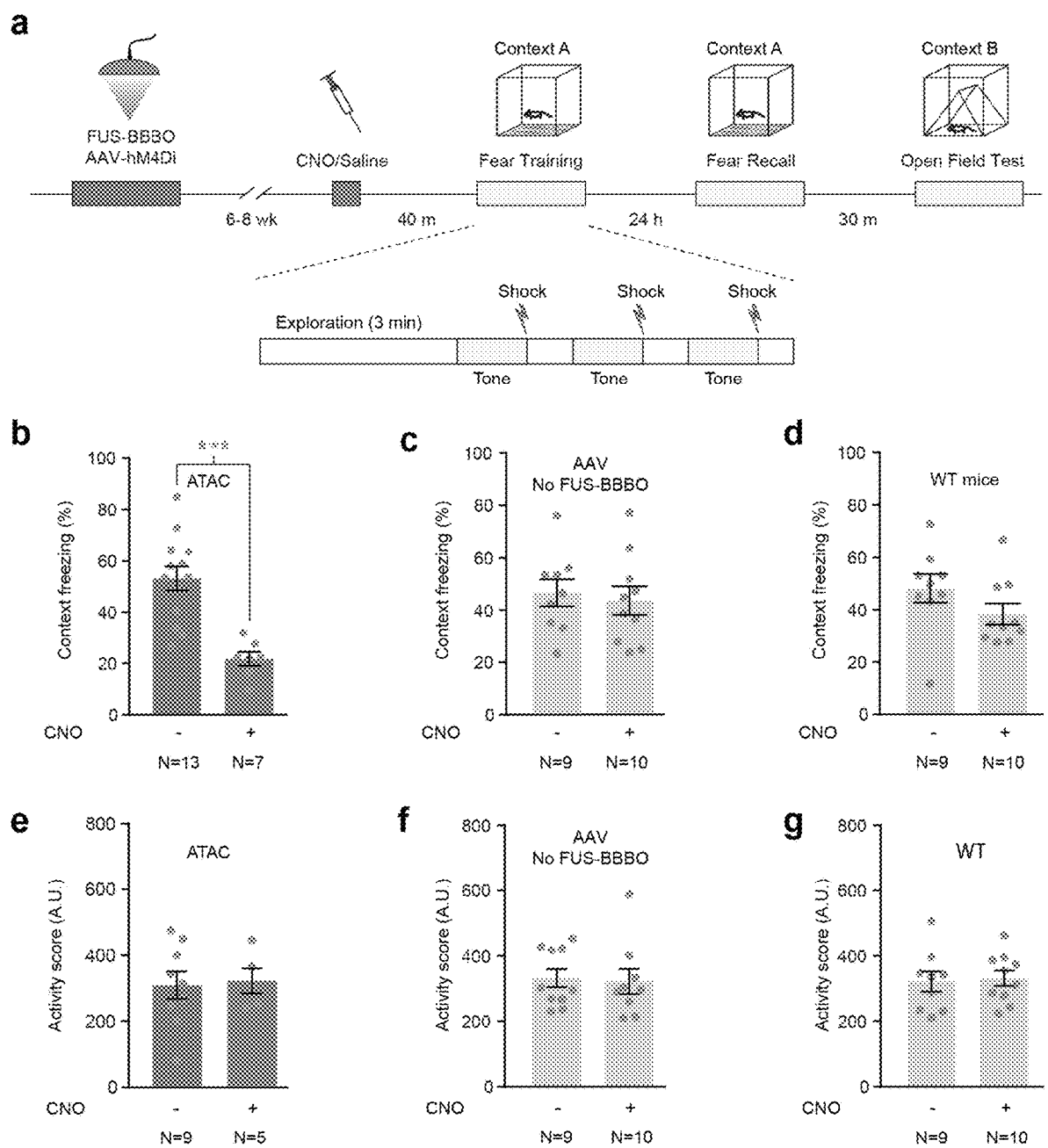

FIG. 5 shows graphs reporting inhibition of fear memory formation using ATAC. In particular, FIG. 5 Panel (a) shows a schematic illustration of an exemplary ATAC and fear conditioning protocol. 6-8 weeks after FUS-BBBO and administration of AAV-DREADD (hM4Di-mCherry), mice were injected with CNO or saline, then placed in a fear conditioning chamber with an electrified floor. After 3 minutes of free exploration, the mice received 3×30-second tones (80 dB) paired with an electric shock during the last 2 s of the tone (0.7 mA) There was a 1-minute interval between tones. 24 h after training, the mice were placed in the same chamber and allowed to explore for (8 min 40 s). 30 min later, the mice were placed in a different context for a 3-minute open field test. FIG. 5 Panel (b) shows diagrams illustrating the percentage of time spent freezing in the fear recall context (Context A) for ATAC mice treated with CNO or saline (p=1.9E-5, two-tailed heteroscedastic t-test) according to an exemplary ATAC method of the present disclosure. FIG. 5 Panel (c) shows diagrams illustrating the percentage of time spent freezing in the fear recall context (Context A) for mice that received IV injection of AAV-DREADD without FUS-BBBO, with CNO and saline treatment (no effect found, p=0.69, two-tailed heteroscedastic t-test) according to an exemplary ATAC method of the disclosure. FIG. 5 Panel (d) shows diagrams illustrating the percentage of time spent freezing in the fear recall context (Context A) for wild-type mice treated with CNO or saline (no effect found, p=0.17, two-tailed heteroscedastic t-test) according to an exemplary ATAC method of the disclosure. FIG. 5 Panel (e) shows diagrams illustrating the exploratory activity score in the non-fear context (Context B) for ATAC mice treated with CNO or saline (p=0.81, two-tailed heteroscedastic t-test) according to an exemplary ATAC method of the disclosure. FIG. 5 Panel (f) shows diagrams illustrating the exploratory activity score in the non-fear context (Context B) for mice that received IV injection of AAV-DREADD without FUS-BBBO, with CNO or saline treatment (no effect founds, p=0.65; two-tailed Mann-whitney test used due to non-normal distribution of data points) according to an exemplary ATAC method of the disclosure. FIG. 5 Panel (g) shows diagrams illustrating the exploratory activity score in the non-fear context (Context B) for wild-type mice that received, with CNO or saline treatment (no effect founds, p=0.79 two-tailed heteroscedastic t-test) according to an exemplary ATAC method of the disclosure. Bar graphs represent the mean±SEM. N provided under each bar indicates number of mice tested in that experimental condition.

Figure 6:
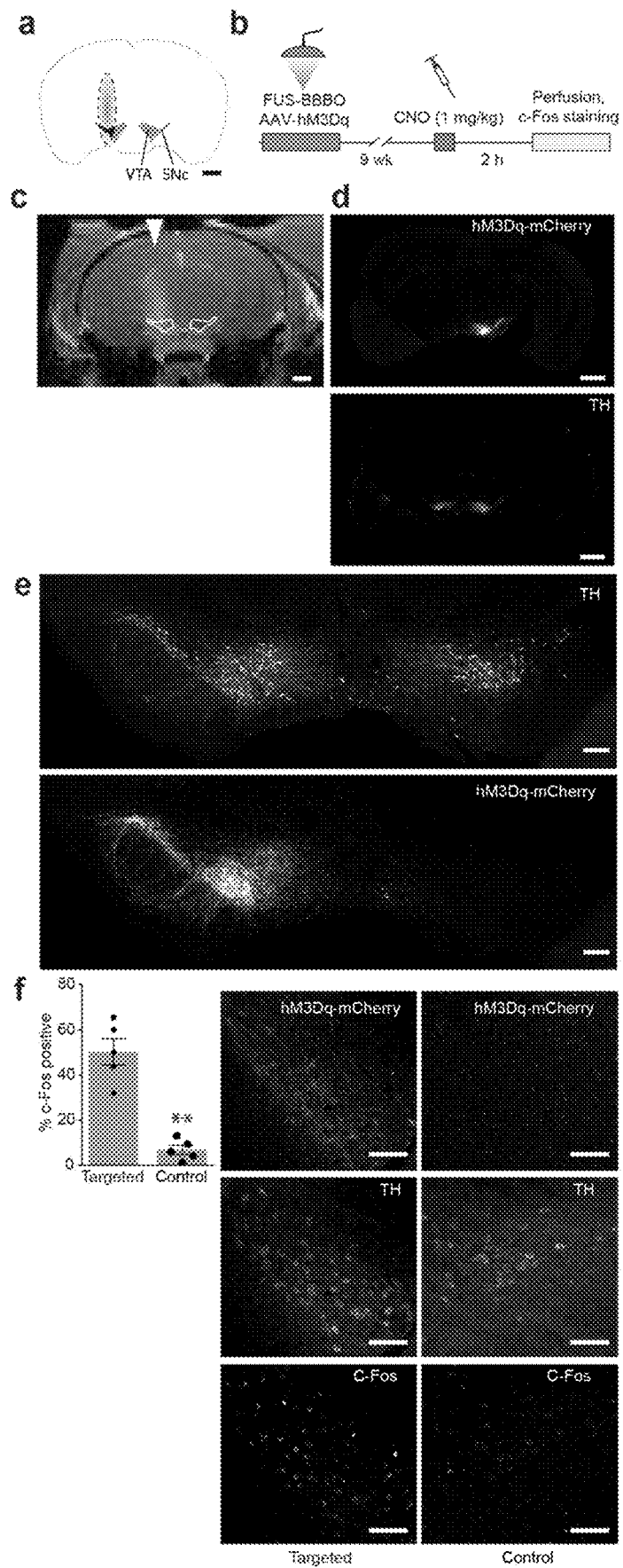

FIG. 6 shows graphs and images illustrating an exemplary embodiment of intersectional-ATAC method of the disclosure performed in the midbrain of CRE transgenic mice. In particular, FIG. 6 Panel (a) shows a schematic illustration of an exemplary intersectional attack experiment according to the present disclosure. FUS-BBBO (grey) was used to target AAV encoding DIO-Syn1-hM3Dq-mCherry unilaterally to the midbrain of TH-CRE mice. Approximate locations of the TH-positive SNc/VTA and FUS target region shown in cyan and pink, respectively. Scale bar is 1 mm. FIG. 6 Panel (b) shows a schematic illustration of an exemplary protocol for c-Fos induction according to methods of the present disclosure. After a period of expression, mice received an IP injection of CNO (1 mg/kg), and 2 hours later were perfused and their brains extracted for histological evaluation. FIG. 6 Panel (c) shows images of a representative $T_1$-weighted MRI scan indicating the site of BBBO (representative of 7 mice) according to an exemplary method of the present disclosure. Outlines show the approximate location of SNc/VTA. The arrowhead indicates the lateral targeting of FUS. Scale bar is 1 mm. FIG. 6 Panel (d) shows images illustrating results of immunostaining for hM3Dq-mCherry and TH, counterstained with DAPI (white) according to an exemplary method herein described. 5 mice were evaluated with similar results. Scale bar is 1 mm. FIG. 6 Panel (e) shows a magnified view of VTA/SNc area in FIG. 6 Panel (d). Scale bar is 200 μm. FIG. 6 Panel (f) shows a diagram and images illustrating the quantification of activated (c-Fos-positive), TH-positive neurons in the ATAC-targeted SNc/VTA region after treatment with CNO according to an exemplary method of the disclosure, compared to contralateral control (p=1.1E-3, paired, two-tailed, t-test, n=5 mice), together with representative histology images of the targeted and contralateral brain regions stained for c-Fos, TH and hM3Dq-mCherry. Scale bar is 100 μm. Bar graphs represent the mean±SEM.

Figure 7:
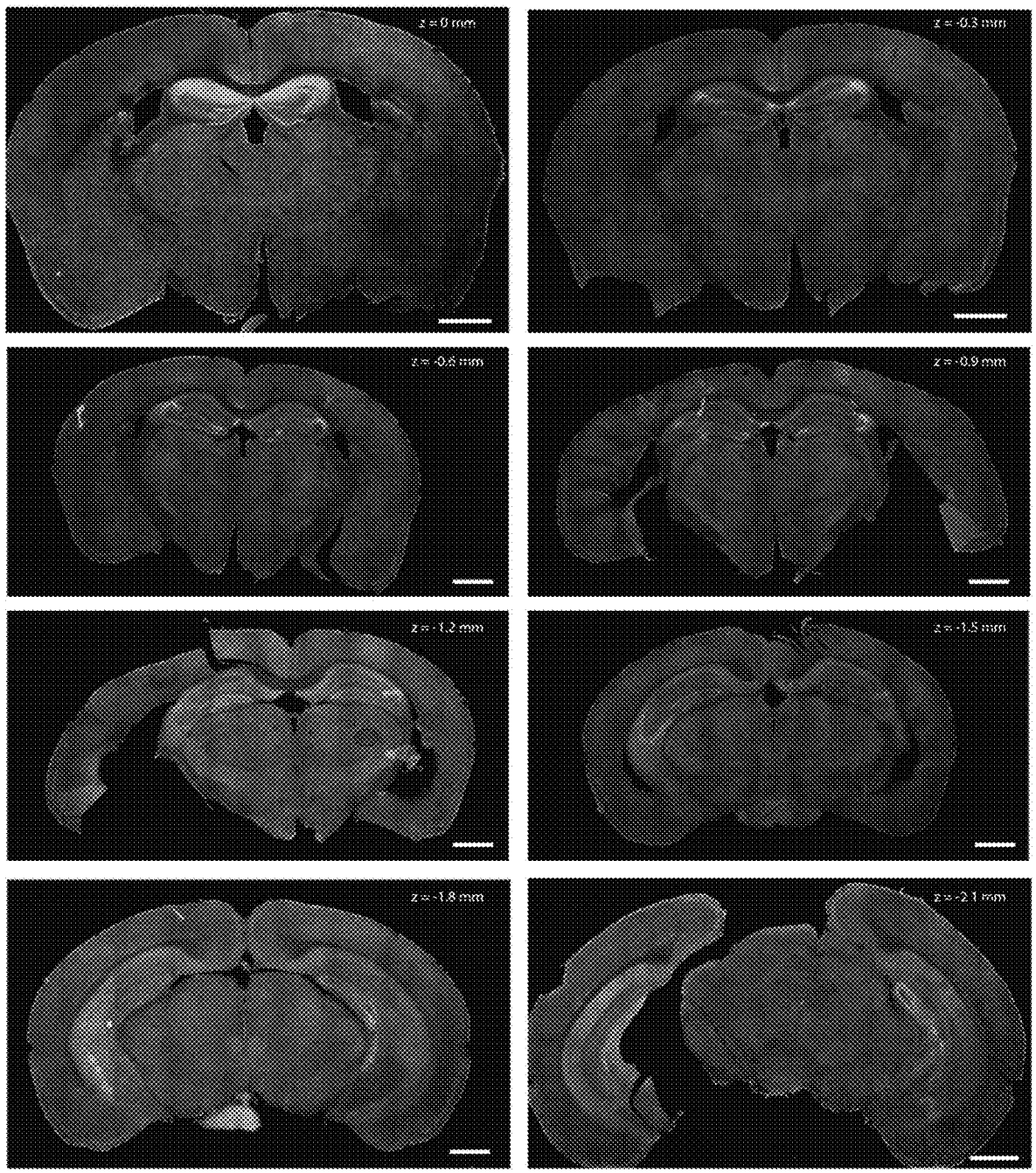

FIG. 7 shows images illustrating an exemplary spatial targeting obtained with an exemplary ATAC method. Additional brain sections from a representative mouse immunostained for hM4Di-mCherry (bright grey) 6 weeks after FUS-BBBO and injection of AAV9 encoding hM4Di-mCherry under the CamkIIa promoter. The DAPI stain demarcates cell nuclei (dark grey, background). Scale bar, 500 μm. Representative of n=4 mice analyzed by immunostaining.

Figure 8:
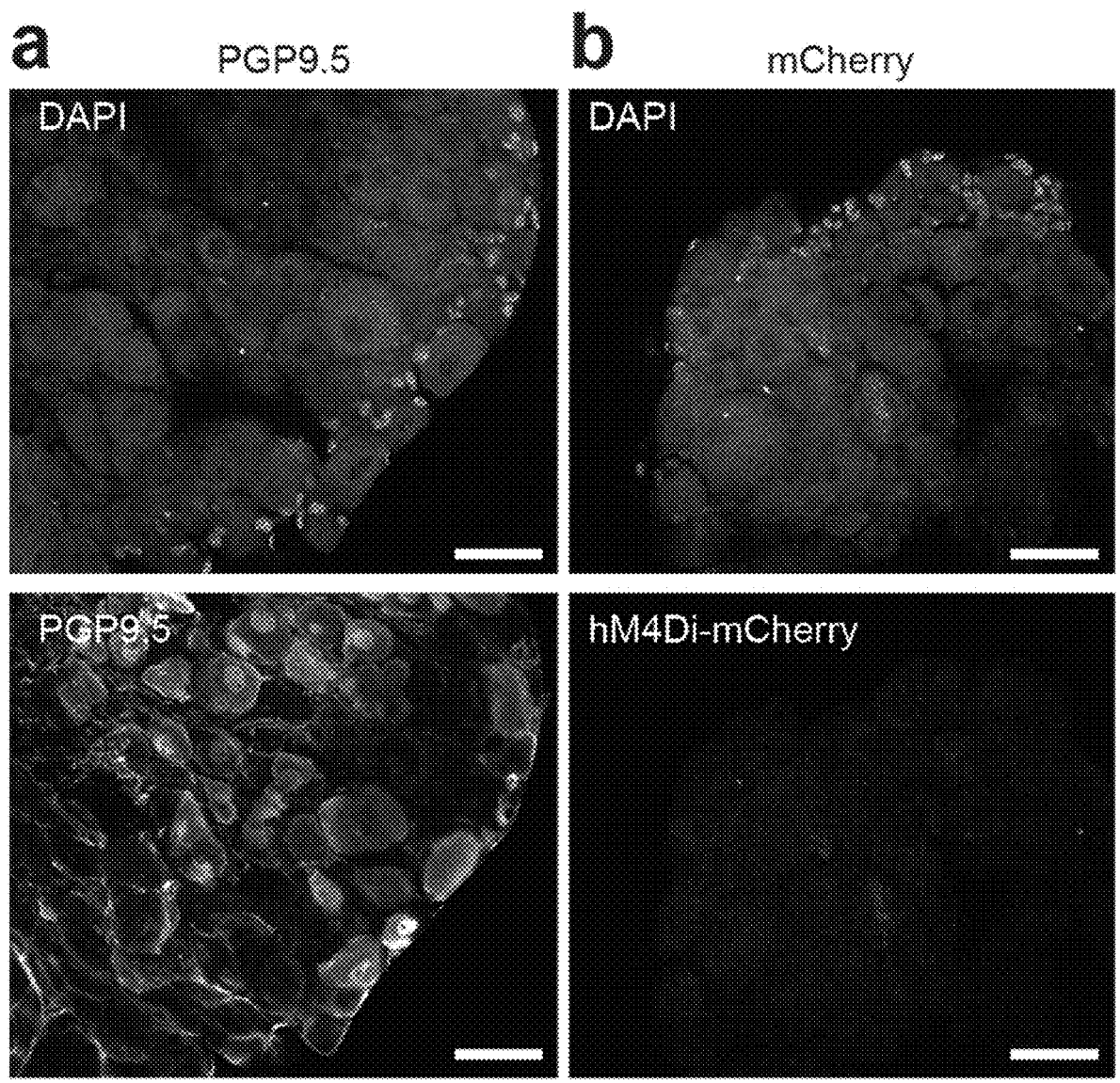

FIG. 8 shows images illustrating that selective AAV9-mediated gene delivery according to an exemplary method of the disclosure fails to target peripheral neurons. In particular, FIG. 8 Panel (a) shows an image of dorsal root ganglion (DRG) sections from a representative mouse immunostained for a positive control neuronal marker PGP9.5 (bright grey) according to an exemplary gene delivery of the disclosure, and counterstained with DAPI. FIG. 8 Panel (b) shows DRG sections from a representative mouse immunostained for hM4Di-mCherry (bright grey) 6 weeks after an exemplary FUS-BBBO and a systemic injection of AAV9 encoding hM4Di-mCherry under the CamkIIa promoter, performed in accordance with an exemplary method of the disclosure. The DAPI stain demarcates cell nuclei (dark grey). Scale bars, 50 μm. Expression of hM4Di-mCherry at the FUS-focus was confirmed in the brain of all animals used in this experiment. Representative of n=4 mice.

Figure 9:
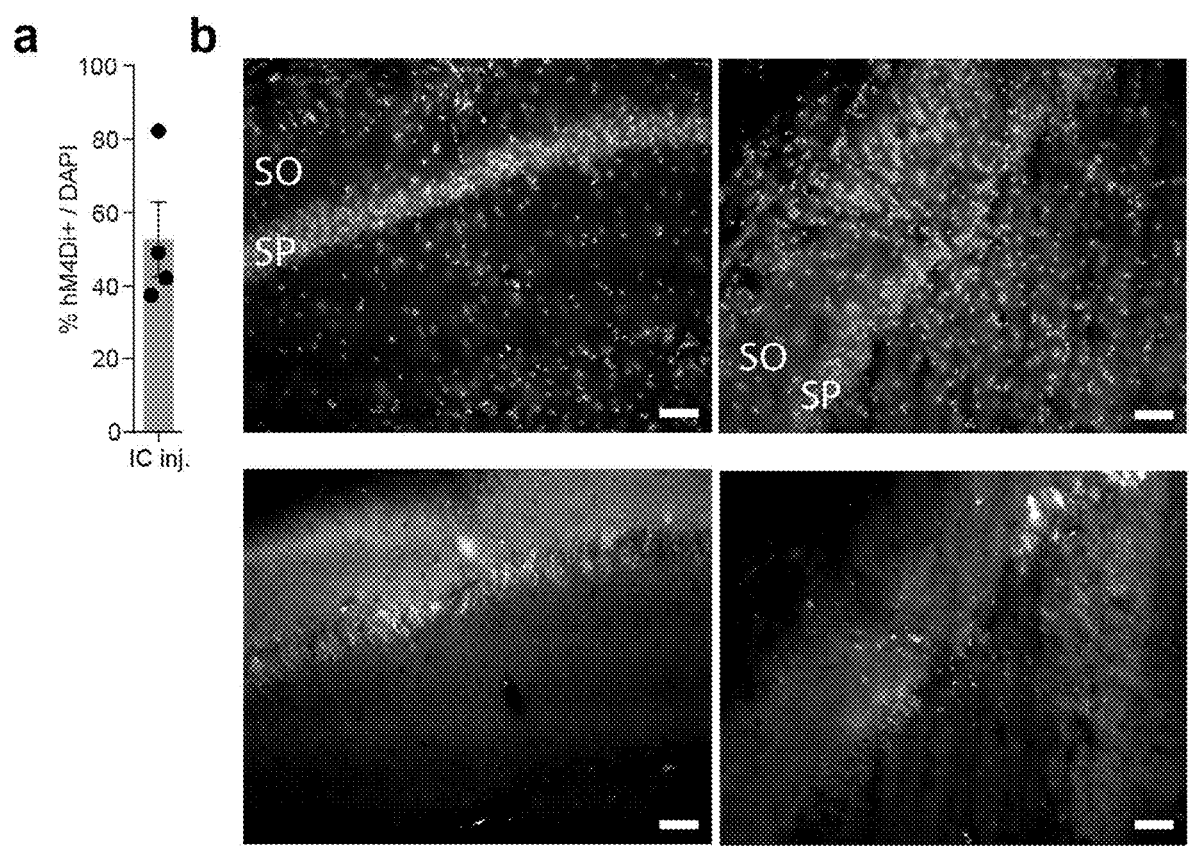

FIG. 9 shows a diagram and images reporting gene expression following an intracranial injection. In particular, FIG. 9 Panel (a) shows a diagram illustrating the results of intracranial injection into both dorsal and ventral hippocampus of an AAV9 encoding inhibitory DREADD (hM4Di-mCherry) under a CamkIIa promoter. After 7 weeks of expression, the percentage of positive cell bodies showing mCherry fluorescence in the granular cell layer of the hippocampus was counted at the sites of injection and normalized to DAPI. FIG. 9 Panel (b) shows images of representative sections at the site of injection of FIG. 9 Panel (a) showing mCherry fluorescence and DAPI staining. Expression can be seen in stratum oriens (SO) and some of the cell bodies in pyramidal layer (SP). Scale bar is 50 µm. Representative of n=4 mice and 8 injections.

Figure 10:
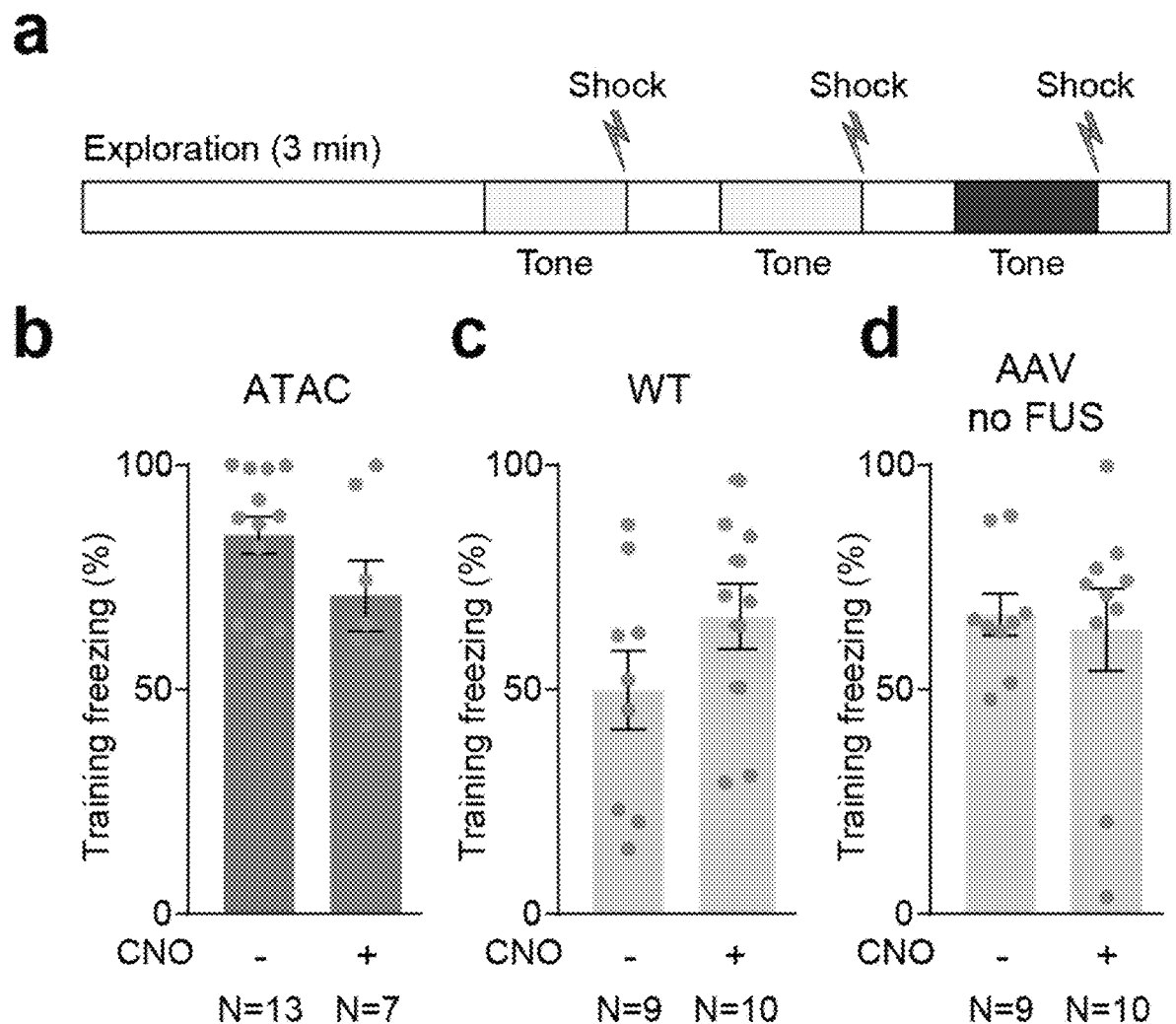

FIG. 10 shows graphs reporting cued conditioning acquisition during training of mice treated with an exemplary ATAC method of the disclosure. In particular, FIG. 10 Panel (a) shows a schematic illustration of the cued conditioning paradigm used in exemplary experiments. Foot shocks are preceded by 30 s audible tones, and freezing is measured during the third tone (dark grey). FIG. 10 Panel (b) shows diagrams illustrating the percentage of time spent freezing during the third tone for ATAC mice treated with CNO according to an exemplary method of the disclosure, or saline (no difference detected, p=0.22, two-tailed, Mann-Whitney test was used due to non-normal distribution). FIG. 10 Panel (c) shows diagrams illustrating the percentage of time spent freezing during the third tone for wild-type mice treated with CNO according to an exemplary method of the disclosure, or saline (no difference detected, p=0.17, two-tailed, heteroscedastic t-test). FIG. 10 Panel (d) shows diagrams illustrating the percentage of time spent freezing by CNO-treated mice that received IV injection of AAV-DREADD without FUS-BBBO according to an exemplary method herein described (no difference detected, p=0.44, two-tailed, Mann-Whitney test used due to non-normal distribution). Bar graphs represent the mean±SEM. N provided under each bar indicates number of mice tested for that experimental condition.

Figure 11:
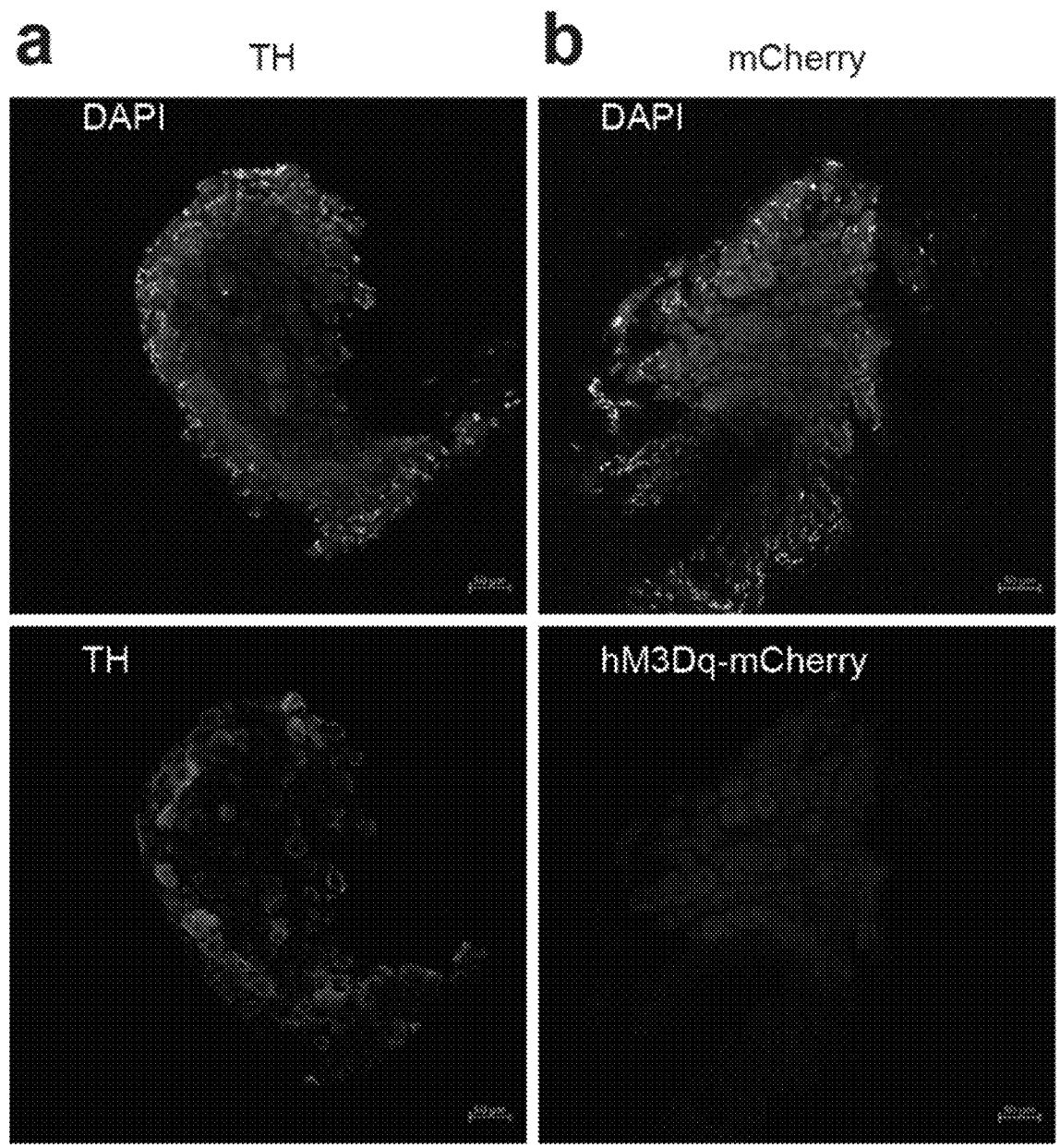

FIG. 11 shows images showing a lack of AAV9-mediated gene delivery into TH-positive peripheral neurons following administration according to an exemplary method herein described. In particular, FIG. 11 Panel (a) shows dorsal root ganglion (DRG) sections from a representative TH-CRE mouse immunostained for a positive control tyrosine-hydroxylase neurons (TH) and counterstained with DAPI. FIG. 11 Panel (b) shows DRG sections from a representative mouse immunostained for hM3Dq-mCherry 9 weeks after a FUS-BBBO and a systemic injection of AAV9 encoding a floxed DIO-hM3Dq-mCherry expressed from the Syn1 promoter. The DAPI stain demarcates cell nuclei. Scale bars, 50 µm. Expression of hM3Dq-mCherry at the FUS-focus was confirmed in the brains of all animals used in this experiment. Representative of n=4 mice.

Figure 12:
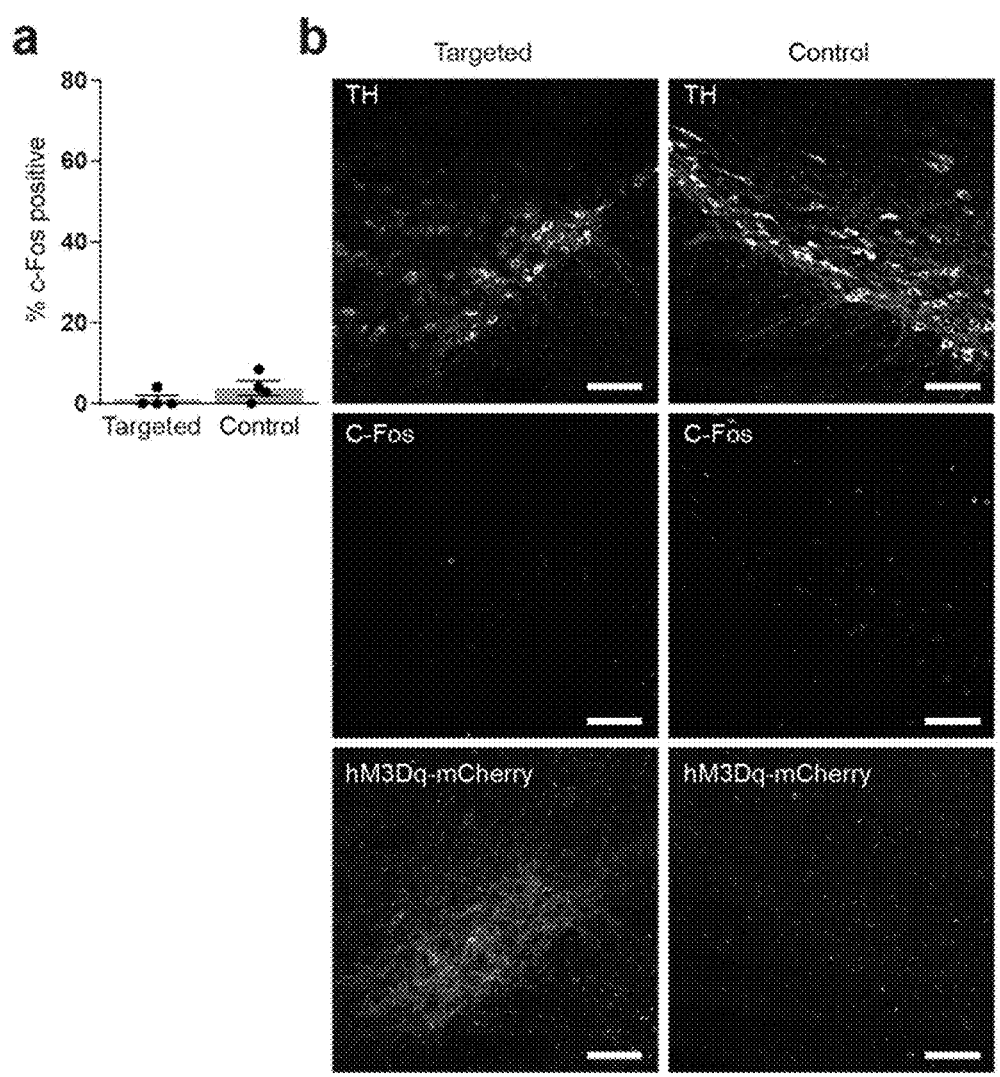

FIG. 12 shows a diagram and images reporting activity of an activatory DREADD in target brain cell according to an exemplary method of the disclosure, in the absence of CNO. In particular, FIG. 12 Panel (a) shows a diagram illustrating the quantification of activated (c-Fos-positive), TH-positive neurons in the ATAC-targeted SNc/VTA region after treatment with saline, compared to contralateral control (no difference detected, p=0.26, paired, two-tailed, t-test, n=4). FIG. 12 Panel (b) shows representative histology images of the targeted and contralateral control brain regions stained for c-Fos, TH and hM3Dq-mCherry. Scale bar is 100 µm. Representative of n=4 mice. Bar graphs represent the mean±SEM.

Figure 13:
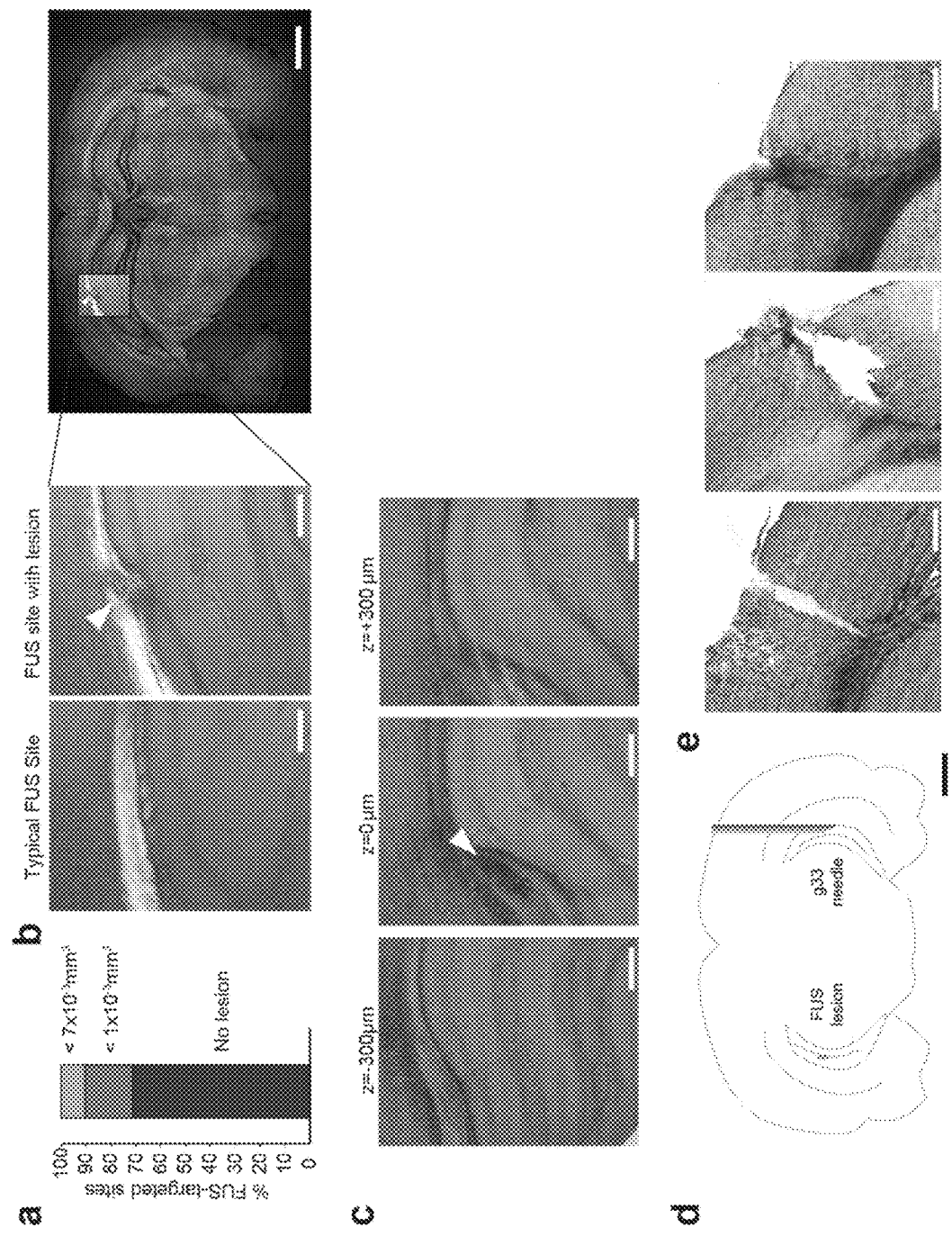

FIG. 13 shows a diagram, images and schematics illustrating an exemplary tissue effects of FUS-BBBO performed according to an exemplary method of the present disclosure. In particular, FIG. 13 Panel (a) shows a diagram illustrating the classification of histological findings at 84 FUS sites in 14 mice. Overall 71.4% of FUS sites had normal histology; 28.6% of sites had small lesions. FIG. 13 Panel (b) shows images of hematoxylin-stained tissue sections containing a typical, undamaged FUS site and a FUS site with a lesion. Mice were perfused and sectioned 6-8 weeks after FUS-BBBO and AAV9 injection. Scale bars represent 200 µm in the color images and 1 mm in the grayscale image. n=14 mice and n=84 independently targeted FUS-sites within these mice were analyzed. FIG. 13 Panel (c) shows images of a representative set of sections at the center of, and ±300 µm away from, a lesion-containing FUS site. n=14 mice analyzed. Scale bars 100 µm. FIG. 13 Panel (d) shows a schematic illustrating the size comparison of the average lesion found at <30% of FUS-BBBO sites (left) and a 33-gauge needle used for intracranial injections in mice (right). Scale bar, 1 mm. FIG. 13 Panel (e) shows images of exemplary hematoxylin-stained tissue 7 weeks after the intracranial injection of AAV9-DREADD. A loss of tissue at and around the needle tract (left and middle panels) and scarring could be found at all injected sites. n=3 mice and n=12 injection sites analyzed. Scale bars are 200 µm.

Figure 14:
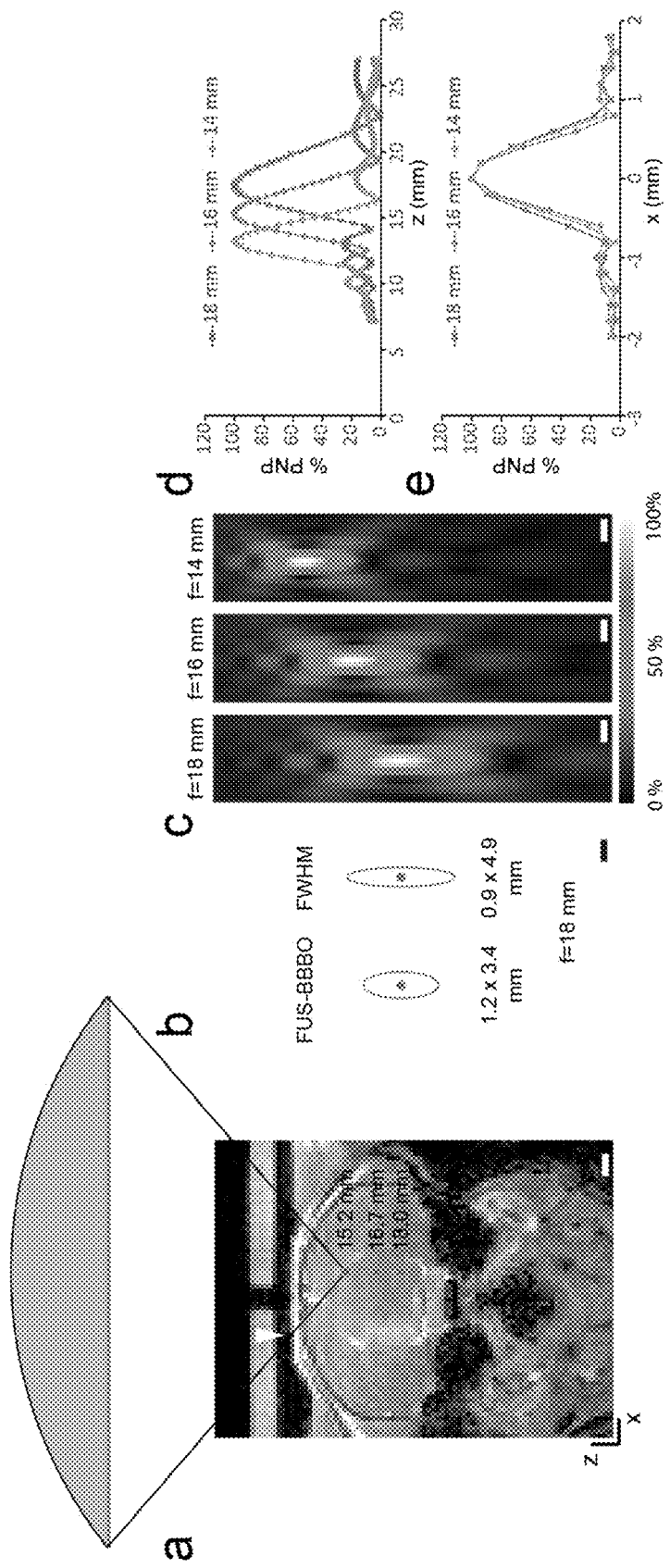

FIG. 14 shows images and charts illustrating an exemplary ultrasound field characterization for 8-element annular array used in the exemplary methods herein described. In particular. FIG. 14 Panel (a) shows an image illustrating the location of the transducer (25 mm diameter) and the targeted focal sites (dots labeled with focal distances) used in this study, overlaid on MRI image of a mouse that received FUS-BBBO targeted to the SNc/VTA site on the left side of its brain at a focal distance of 18 mm. BBBO is indicated by bright $T_1$ contrast (MRI parameters: FLASH 2D, TE 3 ms, TR 100 ms, slice thickness 350 µm, resolution 80×80 µm). n=7 mice analyzed by MRI. FIG. 14 Panel (b) illustrates the expected size of BBB opening of FUS-BBBO as compared to the size of full width half maximum (FWHM) ultrasound pressure. FIG. 14 Panel (c) shows an image illustrating normalized ultrasound pressure fields along the axis of propagation for three focal distances as measured from the face of the transducer (f=18, 16, 14 mm) in water. Instrument characterization based on manufacturer's data, n=1. FIG. 14 Panels (d-e) shows charts illustrating normalized peak negative pressure (PNP) along the axis of propagation (Panel d), and radially at the axial peak (Panel e), for three focal distances (f=18, 16, 14 mm). Instrument characterization based on manufacturer's data, n=1. Scale bars are 1 mm in FIG. 14 Panels (a) and (c), and the panels are rendered at the same scale to enable comparison between them. The presence of skull, or other aberrating or reflecting tissues in vivo, can modify the appearance of the ultrasound beam, potentially resulting in a more complex pattern.

Figure 15:
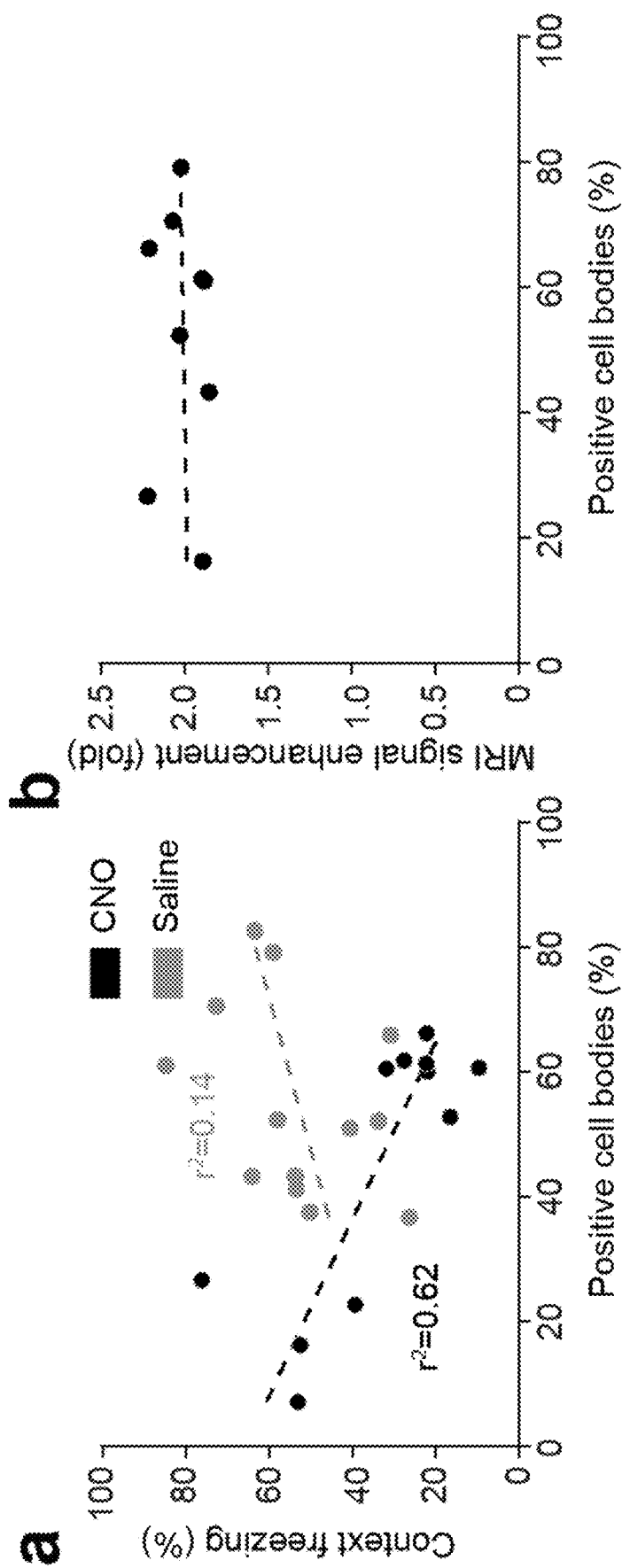

FIG. 15 shows graphs reporting correlation between DREADD expression, fear memory formation and MRI signal enhancement detected in outcome of an exemplary method of the disclosure. In particular, FIG. 15 Panel (a) shows a chart reporting the percentage of time spent freezing in the fear recall context for ATAC mice treated with CNO according to an exemplary method of the disclosure, or saline as a function of hM3Dq-mCherry expression in dorsal CA3. A negative correlation exists for CNO-treated mice, but not for saline-treated mice. Dorsal CA3 was chosen as a site of interest because it had the strongest and most consistent expression throughout the experimental cohort, thus making it directly comparable. N=24 mice analyzed. FIG. 15 Panel (b) shows a chart illustrating the correlation between MRI signal in the FUS-targeted area and hM4Di-mCherry expression intensity following the exemplary method of FIG. 15 Panel (a). Lack of correlation suggests that variability in gene expression could be due to problematic tail-vein injections of the virus, or imperfect correspondence between FUS-BBBO delivery of viruses and small molecules such as Prohance ($r^2<0.01$, N=8).

DETAILED DESCRIPTION

Provided herein are methods, systems, and related vectors and compositions which in several embodiments, allow spatially, cell-type and/or temporally controlled stimulation of the activity of a target brain cell of an individual without need of a surgical treatment.

The term "individual" as used herein indicates an animal comprising a brain which is an organ that serves as the center of the nervous system that coordinates its actions by transmitting signals to and from different parts of its body. The term individual therefore encompasses all vertebrate and most invertebrate animals. In particular, in vertebrates the brain is part of the central nervous system (CNS) together with the spinal cord within a spinal canal. The CNS is enclosed and protected by the meninges, a three-layered system of membranes, including a tough, leathery outer layer called the dura mater. In vertebrates, the nervous system further comprises a peripheral nervous system (PNS) which is a collective term for the nervous system structures that do not lie within the CNS. Exemplary individuals comprise amphibians, reptiles, birds, mammals such as livestock animals, laboratory animals and human beings.

The wording "brain cell" as used herein indicates cells that form the brain of an individual with the exclusion of blood vessels and meninges (dura mater, arachnoid mater, and pia mater in mammals) of the individual. Exemplary brain cells comprise neurons and glial cells.

The terms "neuron", "nerve cell or "neural cell" as used herein interchangeably indicate an electrically excitable cell that receives, processes, and transmits information through electrical and chemical signals. A neuron consists of a cell body (or soma) which contains the neuron's nucleus (with DNA and typical nuclear organelles), branching dendrites (signal receivers) and a projection called axon, which take information away from the cell body and conduct the nerve signal. At the other end of the axon, axon terminals transmit the electro-chemical signal across a synapse (the gap between the axon terminal and the receiving cell). Accordingly, neural brain cells are nerve cells of the brain that transmit nerve signals to and from the brain.

The wording "glial cells" as used herein indicates non-neuronal cells that maintain homeostasis, form myelin, and provide support and protection for neurons within the gray matter of the brain. Glial cells typically comprise macroglial cell such as oligodendrocytes, astrocytes, and ependymal cells, and microglia. Oligodendrocytes are cells that coat axons in the central nervous system (CNS) with their cell membrane, forming a specialized membrane differentiation called myelin, producing the myelin sheath. The myelin sheath provides insulation to the axon that allows electrical signals to propagate more efficiently Astrocytes (also called astroglia) are cells having numerous projections that link neurons to their blood supply while forming the blood-brain barrier. Astrocytes regulate the external chemical environment of neurons by removing excess potassium ions, and recycling neurotransmitters released during synaptic transmission. In particular, astrocytes in the gray matter of a brain comprise protoplasmic astrocytes having short, thick, highly branched processes. Ependymal cells, also named ependymocytes, line the ventricular system of the brain and are involved in the creation and secretion of cerebrospinal fluid (CSF) and beat their cilia to help circulate the CSF and make up the blood-CSF barrier and are also thought to act as neural stem cells. Microglia includes specialized macrophages capable of phagocytosis that protect neurons of the central nervous system (see for example https://en.wikipedia.org/wiki/Neuron).

Brain cells are comprised within areas of the brain defined as gray matter and white matter. The gray matter indicates an area of the brain comprising primarily neuronal cell bodies, neuropil (dendrites and myelinated as well as unmyelinated axons), glial cells (astrocytes and microglia), and synapses. White matter indicates an are of the brain which mainly comprise myelinated axons, also called tracts.

Brain cells are also comprised within "brain regions" which are areas anatomically defined by appearance and position as well as by their locations and their relationships with other parts of the brain. Exemplary brain regions in the sense of the disclosure comprise the medulla (region containing many small nuclei involved in a wide variety of sensory and involuntary motor functions such as vomiting, heart rate and digestive processes), the pons (region of the brainstem directly above the medulla, which contains nuclei that control often voluntary but simple acts such as sleep, respiration, swallowing, bladder function, equilibrium, eye movement, facial expressions, and posture, includes) the hypothalamus (small region at the base of the forebrain composed of numerous small nuclei, each with distinct connections and neurochemistry, and engaged in additional involuntary or partially voluntary acts such as sleep and wake cycles, eating and drinking, and the release of some hormones), the thalamus (a region of nuclei with diverse functions such as relaying information to and from the cerebral hemispheres, motivation, and action-generating systems such as the action generating systems for several types of "consummatory" behaviors such as eating, drinking, defecation, and copulation, in the subthalamic area also zona incerta), the cerebellum (a region modulating the outputs of other brain regions, whether motor related or thought related, to make them certain and precise), the optic tectum (a region usually referred to as the superior colliculus in mammals, allowing actions such as eye movements and reaching movements to be directed toward points in space, most commonly in response to visual input), the pallium (a region of gray matter that lies on the surface of the forebrain also identified in reptiles and mammals as cerebral cortex which with multiple functions including smell and spatial memory), the hippocampus, (a region involved in complex events such as spatial memory and navigation in fishes, birds, reptiles, and mammals), the basal ganglia (a region involved in action selection as the related brain cells send inhibitory signals to all parts of the brain that can generate motor behaviors, and in the right circumstances release the inhibition, it comprises regions such as caudate nucleus, putamen, globus pallidus, substantia nigra, subthalamic nucleus, nucleus accumbens) and the olfactory bulb (a region that processes olfactory sensory signals and sends its output to the olfactory part of the pallium (see for example https://en.wikipedia.org/wiki/Brain). Additional brain regions can be identified by a skilled person In several embodiments of the present disclosure brain cell are further comprised in neural circuits possibly comprising cells and regions of additional parts of the body including cells of the peripheral nervous systems and other systems and organs of the body of the individual.

The wording "neural circuits" as used herein refers to a population of cells including neurons interconnected by synapses to pass an electrochemical signal from a neuron to another to carry out a specific function when activated. In particular the specific function neural circuits herein described manifests in a behavior or physiological function of the individual.

The term "behavior" as used herein indicates an internally coordinated responses (actions or inactions) of a whole living individual to internal and/or external stimuli. Exemplary behaviors in the sense of the disclosure comprise eating, drinking, defecation, and copulation, speaking, contemplating, remembering, focusing attention and additional behaviors identifiable by a skilled person.

The wording "physiological function" as used herein indicates a series of action and reactions performed by components of a living organism such as organ systems, organs, cells, and biomolecules to carry out the chemical and physical functions that exist in the living system. Exemplary physiological functions comprise action and reactions performed by components of the organism of an individual to carry out digestion of food, circulation of blood, contraction of muscles as well as other biophysical and biochemical phenomena, related to the coordinated homeostatic control mechanisms, and the continuous communication between cells in a living organism.

Neural circuits control behaviors and physiological function of an individual and changes in activity of neural circuits can lead to changes in behaviors and physiological functions of an individual as will be understood by a skilled person. [8-10]

Exemplary neural circuit comprise the trisynaptic circuit in the hippocampus. the Papez circuit linking the hypothalamus to the limbic lobe, and neural circuits in the cortico-basal ganglia-thalamo-cortical loop which transmit information from the cortex, to basal ganglia, and thalamus, and back to the cortex, as well as the microcircuitry internal to the striatum the largest structure within the basal ganglia and additional circuits identifiable by a skilled person.

Methods and systems of the disclosure and related vectors and compositions only target brain cells whose cell bodies, dendrites or synapses are located in the gray matter. Accordingly the wording "target brain cell" refers only to brain cells of the gray matter and the wording "target brain regions" only refer to brain regions comprising target brain cells, such as cerebral cortex, cerebellum, thalamus; hypothalamus; subthalamus, basal ganglia such as putamen, globus pallidus, nucleus accumbens; septal nuclei, deep cerebellar nuclei, dentate nucleus, globose nucleus, emboliform nucleus, fastigial nucleus), brainstem and regions thereof such as sub stantia nigra, red nucleus, olivary nuclei, cranial nerve nuclei. The wording "target neural circuit" as used herein only refers to neural circuits that comprise target brain cells such as trisynaptic circuit in the hippocampus.

In particular methods and systems herein described and related vectors and compositions are directed to control a target brain cell activity with respect to a neural circuit, a behavior, a physiological function and/or a condition associated with a target brain cell activity with respect to a neural circuit of the individual.

In particular, the target brain cell activity indicates a series of biological and biochemical reactions resulting in a direct or indirect effect on the synapses of the neural circuit and related passage of the electrochemical signals. Exemplary target brain cell activity in the sense of the disclosure comprise action potential, intrinsic electroresponsive properties like intrinsic transmembrane voltage oscillatory patterns, and production and/or release of chemicals such as neurotransmitters, gliotransmitters, and additional chemicals identifiable by a skilled person.

A target cell activity with respect to a neural circuit can also be associated with a behavior and/or physiological function of the individual. The wording "associated to" as used herein with reference to two items indicates a relation between the two items such that the occurrence of a first item is accompanied by the occurrence of the second item, which includes but is not limited to a cause-effect relation and sign/symptoms-disease relation.

Accordingly, method to detect a target brain cell activity with respect to a neural circuit comprise not only imaging technique such as PET and fMRI and source-localized EEG, but also behavioral and/or physiological evaluation as will be understood by a skilled person. In research animals the activity a target brain cell activity with respect to a neural circuit can additionally be evaluated through invasive recordings or through histology, as shown previously [11].

In methods and systems herein described, the activity of a target brain cell activity with respect to the neural circuit is upregulated or downregulated through a specific and selective delivery and expression of chemogenetic protein configured to activate or inhibit the target brain cell activity following binding with a corresponding chemical actuator or metabolite thereof.

The wording "chemogenetic protein" refers to a protein having an operative state and inoperative state with respect to the activity of a target brain cell. In particular, chemogenetic receptor in an operative state is configured to react with additional molecules in a cell to provide activation or inhibition of the existing activity of a target brain cell through biochemical reactions.

Exemplary reactions of chemogenetic proteins in an operative state that result in activation or inhibition of an existing activity of a target cell with respect to a neural circuit comprise changes in signaling, transmembrane potential, gene expression that lead to changes in probability of generation of action potentials and/or secretion of chemicals in the target brain cell. These changes can be performed by the chemogenetic protein directly and/or by changing the excitability (probability of activation) of ion channels that induce action potentials, by changing the concentration of ion channels within the cells, or by expressing a new set of ion channels that can achieve the same function as will be understood by a skilled person. For example Non-olfactory G protein-coupled receptors (GPCRs), which are among preferred chemogenetic proteins in the sense of the disclosure, follow the Gq/Gs/Gi pathway which change probability of generation of action potential when expressed in neurons.

In particular chemogenetic proteins that can be used in methods and systems of the disclosure and related vectors and compositions comprise protein receptors that activate downstream signaling in the cells or gene expression; and ligand-activated ion channels that change the composition of ions inside, and outside of the cell membrane[12].

Exemplary chemogenetic proteins comprise receptors such as kinases, non-kinase enzymes, G protein-coupled receptors (GPCRs) and ligand-gated ion channels, which can have activating or inhibiting effects on the activity of a target brain cell where they are expressed as will be understood by a skilled person.

In particular, chemogenetic proteins suitable in methods and systems of the disclosure and related vectors and compositions comprise DREADDs (hM4Di (inhibitory), hM3Dq (activatory), hM3Ds (activatory), KORD (activatory), PSAM/PSEM ligand activated ion channels (both inhibitory and activatory versions), GluCl (inhibitory)[13], Tetracycline transactivator (changes in gene expression, inhibition)[14], reverse transactivator (changes in gene expression, activation)[15] and others identifiable to a person skilled in the art.

Conversion of a chemogenetic protein from an inoperative state to an operative state is performed through binding of a corresponding compound also indicated as ligand.

The term "corresponding" used in connection with elements such as ligand and chemogenetic protein identify two or more elements capable of reacting one with another under appropriate conditions. Typically, a reaction between corresponding moieties and in particular chemogenetic protein and respective ligand, results in binding of the two elements.

The term "bind", "binding", "conjugation" as used herein indicates an attractive interaction between two elements which results in a stable association of the element in which the elements are in close proximity to each other.

Attractive interactions in the sense of the present disclosure includes both non-covalent binding and, covalent binding. Covalent binding indicates a form of chemical bonding that is characterized by the sharing of pairs of electrons between atoms, or between atoms and other covalent bonds. For example, attraction-to-repulsion stability that forms between atoms when they share electrons is known as covalent bonding. Covalent bonding includes many kinds of interaction, including σ-bonding, π-bonding, metal to non-metal bonding, agostic interactions, and three-center two-electron bonds. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions.

Binding between a chemogenetic actuator and ligand is typically non-covalent bonding which result in the conversion of the chemogenetic protein from an inoperative state to an operative state. The conversion can occur through a conformational change, aggregation or di- or multimerization as will be understood by a skilled person.

In particular, in embodiments herein described, chemogenetic proteins are selected to specifically respond to a class of ligands comprising chemical actuators or metabolites thereof.

The wording "chemical actuators" as used herein indicates molecules configured to cross the blood brain barrier of the individual and to convert a chemogenetic protein from an inoperative state to an operative state with respect to the activation or inhibition of a target brain cell activity. Chemical actuators in the sense of the disclosure are typically pharmaceutically inert.

In some embodiments the chemical actuator is configured to directly convert a chemogenetic protein from an inoperative state to an operative state through binding of the chemical actuator with the chemogenetic protein. In some embodiments the binding of the chemical actuator to the chemogenetic protein is specific with respect to the molecules present in the environment where the chemogenetic protein is located.

In some embodiments the chemical actuator is configured to indirectly convert the state of a chemogenetic protein from an inoperative state to an operative state through binding of a metabolite of the chemical actuator with the chemogenetic protein. The term metabolite indicates a molecule that can be obtained through breakdown of chemical bonds by enzymes, thermal degradation, or conjugation/binding of a reference molecule with molecules already present in the body. In some embodiments the binding of the metabolite with the chemogenetic protein is specific with respect to the molecules present in the environment where the chemogenetic protein is located.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. By "stable complex" is meant a complex that is detectable and does not require any arbitrary level of stability, although greater stability is generally preferred.

In embodiments of the disclosure chemical actuators and related metabolite refers to molecules which in itself are not naturally present or are present but are biologically inert with respect to the target brain cell not expressing the corresponding chemogenetic protein at the concentrations required for the chemogenetic protein to activate or inhibit the target cell activity when in an operative state.

In some embodiments, a chemical actuator or related metabolite configured to bind the chemogenetic receptor can be a molecule that cross through the BBB based on the lipid-mediate free diffusion. Those molecules can have a molecular weight below 500 Daltons, a number of hydrogen bonds lower than and low affinity ($K_D$ higher than 10 micromolar) to efflux pumps such pGp [16-18]. An example of these molecule is clozapine, can activate chemogenetic receptors of DREADD class at doses >10-fold below what is typically used in the clinic, and consequently has limited side effects.

In some embodiments, a chemical actuator or related metabolite configured to bind the chemogenetic receptor can be a molecule that is a conjugate of another molecule present in the body that naturally cross the BBB, such as amino acids or hexoses. A conjugate refers to a compound formed by the joining of two or more chemical compounds. Examples of these molecules have a binding affinity to GLUT1 and LAT1 transporters.

In some embodiments, a chemical actuator or related metabolite configured to bind the chemogenetic receptor can be a small molecule configured to cross the Blood Brain Barrier (BBB) through active transport by the transporters present in the BBB. Exemplary chemical actuators or related metabolite having these features includes α-amino acids that have a binding affinity to LAT1, LAT2, transporter (e.g. melphalan), or molecules that place the amino- and carboxyl-groups within 0.4 nm radius of the relative positions of these two functional groups in α-amino acids (e.g. gabapentin) in the solution structure of the molecule. Exemplary chemical actuator or related metabolite having these features also include beta-amino acids and conjugates which cross the BBB through pathways analogous to transport of beta-alanine, as well as other conjugates of amino acids, which are actively transported through the BBB[19] which are configured for entering the BBB.

In some embodiments, a chemical actuator or related metabolite configured to bind the chemogenetic receptor can be a fatty acid or a conjugate thereof, which is configured to crosses the BBB through fatty acid transporter[20]

In some embodiments, a chemical actuator or related metabolite configured to bind the chemogenetic receptor can be a protein/peptide therapeutics that cross the BBB. Exemplary chemical actuators or related metabolite having these features include conjugates or protein fusions of antibody (or antibody-fragments) targeting endogenous protein transporters that are present in the BBB[19, 21] (E.g. TfR, PepT1, PepT2, Oatp2, OAT-K1, OATP) and allow trans-BBB transport. Exemplary chemical actuators or related metabolite having these features further include molecules exhibiting affinity to the endogenous protein transporters present in the BBB, e.g. peptides evolved by directed evolution, or through in silico protein engineering methods[22].

In some embodiments, a chemical actuator or related metabolite configured to bind the chemogenetic receptor can be a molecule passing through the BBB using transcytosis of engineered immunoglobulin or fusion proteins that bind to receptors present in the BBB[23].

In some embodiments, a chemical actuator or related metabolite configured to bind the chemogenetic receptor can be a molecule native in species other than the species of the individual, e.g. salvinorin A is a natural product that can be used to activate KORD receptor in mammals.

In some embodiments, a chemical actuator or related metabolite configured to bind the chemogenetic receptor can be molecules that have been engineered to specifically bind with a corresponding chemogenetic proteins.

In some embodiments a chemical actuator or related metabolite configured to bind the chemogenetic receptor can be deliverable through a number of routes, such as oral administration or injections intravenously, subcutaneously, intramuscularly or intraperitoneally [24, 25].

Table 1 from Roth [26] shows a list of exemplary chemogenetic proteins and corresponding chemical actuators that can activate the chemogenetic proteins through direct specific binding to the chemogenetic protein

TABLE 1

Exemplary chemogenetic proteins and corresponding chemical actuators

| Name | Protein(s) | Ligand | Reference |
|---|---|---|---|
| Representative kinases | | | |
| Allele-specific kinase inhibitors | v-I388G | Compound 3g | Liu et al., 1998 |
| Analogue-sensitive kinases | v-Src (I338G, v-Src-as1), c-Fyn (T339G, c-Fyn-as1), c-Abl (T315A, c-Abl-as2), CAMK IIα (F89G, CAMK IIα-as1) and CDK2 (F80G, CDK2-as1) | K252a and PPI analogues | Bishop et al, 1998 |
| Rapamycin-insensitive TOR complex 2 | TORC2 V2227L | BEZ235 | Bishop et al., 2000 |
| ATP-binding pocket mutations in EphB1, EphB2 and EphB3 | Ephb1$^{T697G}$, Ephb2$^{T699A}$, and Ephb3$^{T706A}$ | PP1 analogues | Soskis et al., 2012 |
| ATP-binding pocket mutations of TrkA, TrkB and TrkC | TrkA$^{F592A}$, TrkB$^{F616A}$, and TrkC$^{F617A}$ | 1NMPP1 and 1NaPP1 | Chen et al., 2005 |
| Representative Enzymes | | | |
| Metalloenzymes | Achiral biotinylated rhodium-diphosphine complexes | | Collot et al., 2003 |
| Engineered transaminases | Chemically conjugating a pyridoxamine moiety within the large cavity of intestinal fatty acid binding protein | Enhanced activity | Haring and Distefano, 2001 |
| Representative GPCRs | | | |
| Allele-specific GPCRs | β2-adrenergic receptor, D113S | 1-(3',4'-dihydroxyphenyl)-3-methyl-L-butanone (L-185,870) | Strader et al., 1991 |
| RASSL-Gi (receptors activated solely b synthetic ligand) | k-opioid chimeric receptor | Spiradoline | Coward et al., 1998 |
| Engineered GPCRs | 5-HT2A serotonin receptor F340→L340 | Ketanserin analogues | Westkaemper et al., 1999 |
| Gi-DREADD | M2- and M4 mutant muscarinic receptors | Clozapine-N-Oxide | Armbruster and Roth, 2005; Armbruster et al., 2007 |

TABLE 1-continued

Exemplary chemogenetic proteins and corresponding chemical actuators

| Name | Protein(s) | Ligand | Reference |
|---|---|---|---|
| Gq-DREADD | M1, M3, and M5-mutant muscarinic receptors | Clozapine-N-oxide | Armbruster and Roth, 2005; Armbruster et al., 2007 |
| Gs-DREADD | Chimeric M3-frog Adrenergic receptor | Clozapine-N-oxide | Guettier et al., 2009 |
| Arrestin-DREADD | M3Dq R165L | Clozapine-N-oxide | Nakajima and Wess, 2012 |
| Axonally-targeted silencing | hM4d-neurexin variant | Clozapine-N-oxide | Stachniak et al., 2014 |
| KORD | k-opioid receptor D138N mutant | Salvinorin B | Vardy et al., 2015 |
| Representative Channels | | | |
| GluC1 | Insect Glutmate chloride channel; Y182F mutation | Ivermectin | Lerchner et al., 2007 |
| TrpV1 | TrpV1 in TrpV1 KO mice | capsaicin | Arenkiel et al, 2008 |
| PSAM | Chimeric channels $PSAM^{Q79G,L141S}$ | $PSEM^{9S}$ | Magnus et al., 2011 |
| PSEM | PSAM-GlyR fusions | $PSEM^{89S}$; $PSSEM^{22S}$ | Magnus et al., 2011 |

Additional exemplary chemogenetic proteins and corresponding chemical actuators suitable in methods and systems of the disclosure and related vectors and compositions are identifiable by a skilled person upon reading of the present disclosure.

In some embodiments, chemogenetic receptors can be engineered to modify the related binding selectivity to minimize the binding affinity with their native ligand and maximize affinity for another chemical actuator non native to the individual. For example, a native human muscarinic receptor (hM3, human muscarinic receptor 3) can be engineered into a chemogenetic receptor (DREADD), through mutations introduced to change its binding affinity from acetylcholine to clozapine-n-oxide. At the same time, the engineered receptor can be tested against other ligands present in the mouse brain to ascertain that no endogenous ligands in the brain will lead to activation of the receptor [27]. In another example, a receptor from a different species (e.g. GluCl) can respond to an available drug that does not have significant effect in a mammalian system.[13].

In some embodiments, chemogenetic proteins comprise Designer Receptor Exclusively Activated by Designer Drugs or DREADDs. DREADDs are modified versions of natural activatory or inhibitory GPCRs, engineered to respond to synthetic molecules rather than endogenous ligands[28]. DREADDs have been considered for clinical translation due to their ability to selectively control neural circuits [24].

DREADDs can be classified as Gi-based DREADDs (Gi-DREADDs), Gq-based DREADDs (Gq-DREADDs), and Gs- and β-Arrestin-DREADDs. Exemplary DREADDs include hM3Dq, hM4Di, GsD, R165L β-Arr DREADD, hM4D$^{nrxn}$, KORD (κ-opioid-derived DREADD) and others identifiable to a person skilled in the art. Detailed information about various chemogenetic receptors and particularly DREADDs can be found in the review article by Roth B. L. which is incorporated by reference in its entirety.

For example, Gi-DREADDs include hM2Di, hM4Di, and KORD. hM2Di and hM4Di can be activated by chemical actuators such as clozapine-N-oxide (CNO), DREADD agonist 21 [29], and perlapine. KORD can be activated by pharmaceutically inert compound such as salvinorin B. Both hM4Di and KORD inhibit neuronal activity via two mechanisms: (a) induction of hyperpolarization by Gβ/γ-mediated activation of G-protein inwardly rectifying potassium channels (GIRKs) and (b) via inhibition of the presynaptic release of neurotransmitters (e.g., synaptic silencing).

Gq-DREADDs include hM1Dq, hM3Dq and hM5Dq DREADD. Gq-DREADD can be activated by chemical actuators such as CNO, a pharmacologically inert metabolite of the atypical antipsychotic drug clozapine.

Gs-DREADDs are created by swapping the intracellular regions of the turkey erythrocyte β adrenergic receptor for equivalent regions of a rat M3 DREADD to create a rat eGs-DREADD. β-Arrestin-DREADDs are DREADDs signaling exclusively via β-arrestin.

The chemogenetic protein, for example a hM4Di DREADD, or hM3Dq DREADD can change activity of cells in which it is expressed upon exposure to a drug. Such activity can be defined as any perturbation of signaling, transmembrane potential, gene expression, or molecular composition of the cell. Other chemogenetic proteins could be ligand-activated ion channels (such as PSEM/PSEM, or ivermectin responsive GluCl), or a drug-activated transcription factor, such as tetracycline transactivator (tTA).

In embodiments herein described, selection of a specific chemogenetic receptor is performed based on the desired effect on a target brain cell activity with respect to a target neural circuit and in particular whether an activation or inhibition of the target brain cell activity is desired.

In particular, in embodiments where an inhibition of the target brain cell activity with respect to a target neural circuit is desired, an inhibitory GPCR coupled to Gi g-protein, such as hM4Di DREADD[28], an inhibitory ion channel that leads to decrease of likelihood of depolarization, such as GluCl[13], or other receptors that lead to decreased likelihood of neuronal activation, such as through depolarization of the membrane, can be selected.

In embodiments where an activation or increase of a target brain cell activity with respect to a target neural circuit is desired, an activatory GPCR coupled to Gq or Gs g-protein, such as hM3Dq[27] or activatory ion channel that leads to increase of likelihood of depolarization of the membrane, such as $Ca^{2+}$ conducting PSAM/PSEM[30] can be selected.

In some embodiments of the methods and systems herein described and related vectors and composition, selection of an activating or inhibiting chemogenetic protein can be performed to obtain a target behavior or physiological function of an individual and/or to treat or prevent the condition in the individual associated with the activity of the target brain cell with respect to the target neural circuit of the individual, as will be understood by a skilled person. For example, to reduce the activity of an overactive region of the brain, such as an epileptogenic focus in epilepsy, an inhibiting chemogenetic protein would be chosen and targeted to excitatory cells within the epileptogenic focus.

In methods and system herein described administering a chemogenetic protein configured to activate or inhibit, when in an operative state, a target brain cell activity with respect to a target neural circuit, is performed by acoustically delivering to the target controlling brain cell of the individual an expression vector configured to express in the target controlling brain cell a gene encoding for a chemogenetic protein to obtain a chemogenetically treated target brain cell comprising an expressed chemogenetic protein.

In particular, in methods and systems of the disclosure the acoustically delivering is performed by applying focused ultrasound to a target region in the brain of a subject and systemically administering an effective amount of microbubble contrast agents designed to stably cavitate in response to the ultrasound field produced by the focused ultrasound at the target brain region for a time and under conditions to induce transient blood-brain barrier opening;

before, simultaneously, in combination with and/or after applying focused ultrasound, systemically administering an effective amount of an expression vector configured to enter the brain at the site of an open blood-brain barrier and deliver to the brain cells at that site a gene encoding a chemogenetic protein under the control of a promoter active in the target brain cell, the chemogenetic protein configured to activate or inhibit the target brain cell activity following binding with a corresponding chemical actuator or metabolite thereof.

The term "ultrasound" refers to sound with frequencies higher than the audible limits of human beings, typically over 20 kHz. Ultrasound devices typically can range up to the gigahertz range of frequencies, with most medical ultrasound devices operating in the 0.2 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a person skilled in focused ultrasound.

Focused ultrasound ("FUS") refers to the technology that uses ultrasound energy to target specific areas of a subject, such as a specific area of a brain or body. FUS focuses acoustic waves by employing concave transducers that usually have a single geometric focus, or an array of ultrasound transducer elements which are actuated in a spatiotemporal pattern such as to produce one or more focal zones. At this focus or foci most of the power is delivered during sonication in order to induce mechanical effects, thermal effects, or both. The frequencies used for focused ultrasound are in the range of 200 KHz to 8000 KHz. Depending on the design of the ultrasound transducers and the ultrasound parameters, the target brain region can be as in a range between 1 and 10 mm in diameter as will be understood by a skilled person.

In particular, in embodiments herein described the applying focused ultrasound can be performed by performing FUS-BBBO.

The term "FUS-BBBO" refers to techniques that applies ultrasound waves to a target region, in conjunction with microbubbles, to temporally induce localized blood-brain barrier ("BBB") opening noninvasively and regionally. In particular, FUS delivers low frequency ultrasound waves which cause mechanical oscillations in microbubbles resulting in disruption of endothelial cells ("EC") tight junctions leading to enhanced BBB permeability to agents. FUS—BBBO has also been tested in the clinic as will be understood by skilled person [31], Accordingly, in methods and systems of the present disclosure, the applying of a focused ultrasound is performed together with the systemic administration to the individual of an effective amount of microbubble contrast agents designed to stably cavitate in response to an ultrasound field produced by the focused ultrasound at the target brain region, for a time and under conditions allowing to obtain a transient BBB opening, In particular the applying ultrasound can be performed before, simultaneously, or in combination administration of a microbubble contrast agent according to any settings that will ensure application of ultrasound in presence of an effective amount of microbubbles at the BBB of the individual in correspondence with the target region.

The term "contrast agent" refers to an agent (material) in aqueous media, including water, saline, buffer, liquid media, configured to increase contrast in ultrasound methods. By an increase in contrast, it is meant that the differences in image intensity between adjacent tissues visualized by an ultrasound imaging method are enhanced.

The contrast agent can be provided in any pharmaceutically and/or physiologically suitable liquid or buffer known in the art. For example, the contrast agent can be contained in water, physiological saline, balanced salt solutions, buffers, aqueous dextrose, glycerol or the like. In certain embodiments, the contrast agent can be combined with agents that can stabilize and/or enhance delivery of the contrast agent to the target site. For example, the contrast agent can be administered with detergents, wetting agents, emulsifying agents, dispersing agents or preservatives.

The contrast agent comprised in methods and systems of the disclosure comprises "microbubbles" defined as particles smaller than the blood vessel diameter and able to undergo stable cavitation or capable of inducing stable cavitation. In particular microbubble contrast agents in the sense of the disclosure comprises microbubbles designed to stably cavitate in response to an ultrasound field produced by the focused ultrasound at the target brain region. Microbubbles can comprise an inert gas encapsulated by a shell. The microbubbles in general have an average diameter between 1 and 5 microns.

Exemplary microbubbles include The Definity®, Sonovue®, Optison®, and USphere®. Such microbubbles contain an encapsulated gas (typically perfluren, C3F8) and a shell. This shell depends on the manufacturer and can be either lipid or protein. For example, definity contains a mixture of DPPA, DPPC, MPEG5000 DPPE lipids in the shell. Optison has a shell made out of albumin. Sonovue has a phospholipid shell and USphere, is made of lipid and polymeric adducts.

Microbubbles are typically administered intravenously to the individual for a time and in an effective amount to achieve a concentration in the target brain region causing in combination with ultrasound waves mechanical oscillations disruption of tight junctions between endothelial cells ("EC") without disrupting the cells leading to enhanced BBB permeability.

In embodiments herein described the timing of contrast agent depends on the half life of microbubbles in the organism of the given individual as will be understood by a skilled person.

In embodiments herein described, the microbubbles are typically administered to the target region before the application of focused ultrasound at a time sufficient to provide the microbubbles to the BBB at appropriate concentrations. Typically, the microbubbles are administered between 0 and 1 minutes before the application of focused ultrasound. In some cases, the microbubbles are administered first, followed by an immediate application of focused ultrasound.

In some exemplary embodiments, wherein the FUS is applied about 10 seconds after administering of the contrast agent, the microbubble concentration can be in the range of 1E5-1E7 microbubbles per g of body weight for mice; 2.4E7-2.4E9 microbubbles/kg of body weight for rats, and 1.2E7-1.2E9 per kg of body weight for non-human primates and humans.

In some preferred embodiments, the microbubble concentration is 1.5E9 microbubbles/kg of body weight in mice, 2.4E8 per kg of body weight in rats, and 1.2E8 per kg of body weight in non-human primates and humans.

Additional combinations of timing and concentrations of the administering of a contrast agent according to methods of the instant disclosure can be identified by a skilled person taking into account that the presence of microbubbles present in the blood supply allows for the reduction of the ultrasound intensity that is necessary for BBB opening, the containment of most of the disruption within the vasculature, and the reduction of the likelihood of irreversible neuronal damage. [32]. In this connection, increase of the concentration of contrast agent will allow increase of the time interval before applying the focused ultrasound according to methods of the disclosure. For example, increase of the concentration of the contrast agent by 10-times, allows one to wait 5 minutes and still have the same BBB opening as one would have by injecting $1/10^{th}$ and waiting 10 seconds.

Accordingly, in embodiments herein described, the applying focused ultrasound to a target region in the brain of an individual and systemically administering to the individual an effective amount of microbubble contrast agents is performed to temporally induce blood-brain barrier opening. The term "transient" "temporary" refers to a reversible opening for a limited period of time before the blood-brain barrier returning to its initial state.

In the embodiments herein described, applying focused ultrasound to a target region in the brain can transiently or temporarily open the blood-brain barrier ("BBB") in the target region to allow the delivery of an effective amount of vector.

The term "BBB" refers to a highly selective semipermeable border that separates the circulating blood from the brain and extracellular fluid in the central nervous system. BBB allows the passage of water, some gases, and lipid-soluble molecules by passive diffusion, as well as the selective transport of small molecules such as glucose and amino acids that are crucial to neural function, but restricts the diffusion of solutes in the blood and large or hydrophilic molecules into the cerebrospinal fluid. As such, the BBB is able to prevent the entrance of most substances such as toxins, drugs, viruses and bacteria from the blood stream into brain tissue. Due to the BBB's restrictive permeability, the BBB presents a natural barrier for the delivery of gene vectors to the brain.

In some embodiments, the subject is placed in a direct contact with an ultrasound-conductive medium, such as ultrasound gel or degassed water, that is coupled to an ultrasound transducer. The transducer is focused on the area of intended opening of the BBB. If needed, multiple transducers or array transducers can be used to correct for aberration in the sound field due to the skull or vertebrae.

The targeted region is chosen based on medical imaging and/or anatomical information of the subject. Such imaging includes, but is not limited to, MRI, CT, PET, ultrasound imaging. Anatomical information will use external fiducial markers on the body to establish location of the targeted site.

The sites and cells targeted depend on various applications and the intended effect. Different brain regions perform different functions and therefore neuromodulation of different brain regions with ATAC can lead to different behavioral/therapeutic/cell-activity effects. For example, for epilepsy treatment such site could be a seizure focus area. While for memory-related disorders, it could be a hippocampus. And for treatment of Parkinson's disease, it could be the basal ganglia.

In some embodiments, single- and/or multi-element ultrasound transducers operating at frequencies of 100 kHz to 100 MHz are used. The preferred ultrasound frequency range is between 1 and 10 MHz for rats and mice, and 0.2 to 1.5 MHz for non-human primates and humans. The transducers are typically driven by a waveform generator and radiofrequency amplifier. Accounting for attenuation through the medium, brain tissue and bone, the acoustic output power at the transducer focus is sufficient to open the BBB after infusion of microbubble contrast agents and mechanical index is kept below 1.9, and above 0.2. The preferred range of mechanical indices of ultrasound at the brain is between 0.2 and 0.6 for all species. The term "mechanical index" is a measure of acoustic power, i.e. the amount of acoustic energy per time unit. Acoustic power shows the amplitude of the pulse pressure of the ultrasound beam. Mechanical index provides information about the magnitude of energy administered to a subject during the ultrasound application.

In the embodiments herein described, the methods further comprise administering an effective amount of an expression vector encoding a chemogenetic receptor to the target brain region and particularly to specific cell types among the target brain region before, simultaneously, in combination with or after the applying focused ultrasound.

In particular, in methods and systems herein described the administering the expression vector can be performed before, simultaneously, in combination or after the applying ultrasound and the administration of a microbubble contrast agent, in accordance with any settings that will presence of an effective expression vector at the transient BBB opening site.

An "expression vector" in the sense of the disclosure indicates a construct configured to introduce a specific gene into a target cell, and to produce the protein encoded by the gene using the target cell mechanism. An expression vector typically comprises elements necessary for gene expression such as a promoter, a correct translation initiation sequence such as a ribosomal binding site and start codon, a termination codon, and a transcription termination sequence. An expression vector can also comprise additional elements such as an origin of replication, a selectable marker, and a suitable site for the insertion of a gene such as the multiple cloning site.

Expression vectors comprise viral vectors, and gene delivery nanomaterials comprising appropriate regulatory elements such as promoters, enhancers, and post-transcriptional and post-translational regulatory sequences that are compatible with the target cell expressing the gene, as would be understood by a skilled person.

Expression vectors that can be delivered with focused ultrasound typically have a size below 50 nm in diameter, and can be administered systemically to circulate in the serum.

Exemplary expression vectors that can be used in methods and systems herein described, include viral vectors such as adeno-associated vectors. Expression vectors can also include non-viral gene delivery nanomaterials such as polymeric nanoparticles or liposomes, and others identifiable by a person skilled in the art.

In some embodiments, expression vectors that can be used in methods and systems herein described comprise naked DNA bound electrostatically to microbubbles can be used for delivery, so microbubbles in a way are the delivery vectors. [33, 34]

In some preferred embodiments, the viral vectors used in the current disclosure comprise adeno-associated viral vectors ("AAV"). AAVs are nonenveloped, single-stranded DNA viruses of the *Dependoparvovirus* genus of the Parvoviridae family. AAVs are innately nonpathogenic, poorly immunogenic, and broadly tropic, making them attractive gene delivery candidates for virus-based gene therapies. AAV vectors have shown to stably transfect mammalian cells without integration into the target genome. [35-39] AAVs are currently investigated in clinical trials with promising result s[35, 36, 40, 41], and recent developments in AAV vectors also enable some variants to cross the BBB on their own[42].

AAVs of various serotypes can be used as vectors for carrying chemogenetic protein genes. AAV serotypes are identified based on their interacting glycan moieties that mediate the initial attachment of AAVs to the cell surface. Examples of AAV serotypes include AAV serotype 1 ("AAV1"), AAV2, AAV3, AAV5, AAV6, AAV9 and other serotypes identifiable to a person skilled in the art such as AAV7, AAV8, AAV11, AAV-DJ.

In most preferred embodiments, the viral vectors used for delivery of genes encoding for chemogenetic protein can comprise AAV9. The concentrations used for this serotype are at least 1E9 viral particles per gram of body weight, and at most 1E12 viral particles per gram of body weight. The preferred concentration is in the range of 1E10-2E10 viral particles for gram of body weight for mice, 1E10-2E10 viral particles per gram of body weight for rats, and 2E13-2E14 viral particles per kilogram of body weight for non-human primates and humans.

The results can be replicated with other delivery vectors and the choice of vector will depend on the species as will be understood by a skilled person upon reading of the present disclosure.

In embodiments herein described, the expression vector and related concentrations can be selected based on the desired transfer speed from blood stream to the target region, the desired percentage population to be transfected, species, and cell tropism as will be understood by a skilled person [43, 44]

In an exemplary preferred embodiment wherein the methods and systems of the disclosure are designed to activate or inhibit the activity of at least 40% of target brain cell the AAV serotype is AAV9. The concentrations used for this serotype will be at least 1E9 viral particles per gram of body weight, and at most 1E12 viral particles per gram of body weight. The preferred concentration for mice is 1E10 viral particles for gram of body weight. For rats this concentration range is 1E10 viral particles per gram of body weight, and for non-human primates and humans is at least 2E13 viral particles per kilogram of body weight.

In other exemplary embodiments expression vectors can be other AAV serotypes and the concentrations will be adapted as will be understood by a skilled person. In particular AAV2 will require 10-fold the AAV9 concentration.

Non-viral gene delivery vectors can also be used. The unifying feature is that the vector is configured to lead to expression of a chemogenetic protein in at least 40% of the targeted gene population when used in combination with FUS BBB opening. For humans and non-human primates the alternative AAV serotypes are those that do not have neutralizing antibodies in the serum of particular subject/patient.

In particular, several target brain regions can require more or less virus, for example
CA2 and CA3 fields of hippocampus will require ½ of the preferred dose due to efficient transfer of the AAV from bloodstream and good virus tropism to those regions [11];
the dentate gyrus region will require ⅔rds of the virus dose[11]; and
The CA1 region of hippocampus will require 2-fold higher dose to ensure 25% transfection efficiency [11]

For example, in embodiments wherein the targeted neural circuits require high efficiency of delivery, AAV9 is preferred. In some embodiments wherein a decreased spread of the vectors is desired, or when neutralizing antibodies against AA9 are present in the serum of a treated subject, AAV1, AAV8, and AAV2 can be used to increase the accuracy of delivery and circumvent the immunogenicity of the vector.

In methods and systems of the present disclosure, levels of transfection by the expression vector following the related administered can be tested by biopsy and subsequent histology, which can then be tested using immunostaining and cell-counts, and imaging techniques such as PET with radiolabeled ligand, which will show average level of expression in the tissue.

Selection of an expression vector can also be performed in view of the target brain regions and in particular, in view of the target brain region size, target cells and tropism of the vector for the target cell as well as in view of presence or absence of neutralizing antibodies for the vector. For example for brain regions that are of the size of a FUS BBBO beam or larger, and there is no AAV9 neutralizing antibodies, AAV9 is preferred. If the targeted site is smaller then the FUS beam and/or the individual organisms have neutralizing antibodies against AAV9, or AAV2 or more preferably AAV8 or even more preferably AAV1, can be used at equivalent doses. The delivery and expression of the chemogenetic in a percentage population of least 40% of the target brain cells of the target brain region will be restricted to a smaller region compared to AAV9.

Non-viral expression vectors, such as nanomaterials, microbubble bound DNA or free DNA, can be used to replace viral expression vectors in cases where a large amount of serum neutralizing antibodies is present in the subject for all known AAV serotypes. The appropriate dosing will need to be determined empirically for each new expression vector.

In methods and systems of the present disclosure, levels of transfection by the expression vector following the related administered can be tested by biopsy and subsequent histology, which can then be tested using immunostaining and cell-counts, and imaging techniques such as PET with radiolabeled ligand, which will show average level of expression in the tissue.

In embodiments herein described, the expression vector carrying a gene encoding for a chemogenetic protein acoustically delivered to a target brain region comprises the gene encoding a chemogenetic protein under control of a promoter configured to be active in the target brain cell.

In particular in embodiments herein described, the nucleic acids encoding the chemogenetic protein can be under the control of a cell specific promoter operatively connected to the gene of the chemogenetic protein. A "promoter" as used herein indicates is a region of DNA that initiates transcription of a particular gene as will be understood by a skilled person. In embodiments wherein cell specific promoter of the vector are selected to be cell specific, the vectors is configured to have the promoter controlling the expression of the chemogenetic gene, specifically recognized by the native synthetic machinery of the target controlling brain cell.

In some particular embodiments, wherein the target brain cell is a neuron, the cell specific promoter is a synapsin, such as synapsin1 and in particular human synapsin1. Other variants of Synapsin 1 promoter exist (eg. Rat synapsin 1 promoter) which are closely associated and identifiable to a skill person.

In some embodiments, a neuron cell specific promoter can be a tyrosine hydroxylase promoter, a melanopsin promoter, or a promoter that expresses in retinal neurons.

In another embodiment, the neuron cell specific promoter can be a PRSx8 promoter which specifically targets catecholaminergic neurons. PRSx8 is based on an upstream regulatory site in the human Dopamine Beta-Hydroxylase ("DBH") promoter and drives high levels of expression in adrenergic neurons.

In another embodiment, the neuron-specific promoter can be preprotachykinin-1 promoter (TAC-1).

Other exemplary cell-specific promoters include neuron-specific enolase (NSE) and the promoters listed in the following Table 2.

TABLE 2

Exemplary cell-specific promoters

| Name | Size | Specificity |
| --- | --- | --- |
| GFAP104 | 845 bp | Hybrid of EF1a and GFAP |
| CamKIIa | 1.2 kb | Specific expression in excitatory neurons in the neocortex and hippocampus |
| CK0.4 | 217 bp | Calcium/Calmodulin-dependent kinase II alpha |
| GFAP | 2.0 kb | Specific in astrocyte |
| MBP | 1.3 kb | Myelin basic protein promoter, efficient transduction of oligodendrocytes by adeno-associated virus type 8 vectors |
| Synapsin | 471 bp | Specific in neuron |
| Mecp2 | 230 bp | Truncated Mcep2 neuron specific |
| c-fos | 1.7 kb | Activity-dependent promoter |
| Somatostat | 1.2 kb | Restricting expression to GABAergic neuron |
| Rpe65 | 700 bp | Retinal Pigment epithelium-specific expression in vivo and in vitro |
| NSE | 1.3 kb | Neuron-specific enolase promoter |

Additional promoters specific for any target neurons and/or glial cells can be identified by a skilled person e.g. by sequencing transcriptome of selected group of cells in model organisms (e.g. mouse) and finding specific genes that are expressed in that cell line, producing cell-specific proteins (CSP). One would then perform a computational search of sequences resembling promoters and enhancers upstream of that gene on the DNA, package that sequence along with a reporter gene (RG) in a viral vector. For each candidate sequence one would use an antibody against a cell-specific protein (CSP) to confirm identity of the cells in histology and confirm that expression of a reporter gene (RG) is restricted only to cells that also contain CSP. Such procedure can be understood by a person skilled in the art.

Expression vectors herein described can further comprise additional regulatory sequences that can be also cell specific. Accordingly, in some embodiments, an expression vector of the disclosure can comprise a polynucleotide encoding for one or more chemogenetic proteins herein described, under control of one or more regulatory sequence regions in a configuration allowing to express chemogenetic proteins encoded by the polynucleotide in presence of suitable cellular transcription and translation factors.

Regulatory regions of a gene herein described comprise transcription factor binding sites, operators, activator binding sites, repressor binding sites, enhancers, protein-protein binding domains, RNA binding domains, DNA binding domains, silencers, insulators and additional regulatory regions that can alter gene expression in response to developmental and/or external stimuli as will be recognized by a person skilled in the art.

In some embodiments an expression vector can comprise one or more polynucleotides encoding a chemogenetic protein herein described under control of one or more regulatory sequences including enhancer regions in a configuration allowing regulation of expression of the chemogenetic proteins encoded by the polynucleotide in presence of necessary cellular transcription and translation factors. The regulatory sequences such as promoter and/or enhancer regions can be arranged proximally and/or distally 5' and/or 3' to the one or more polynucleotides encoding for a chemogenetic protein herein described. The expression vector can also comprise additional regulatory elements such as ribosome binding sites, and transcription termination sequences. In some embodiments, the regulatory sequences of promoter and/or enhancer regions regulating expression of one or more polynucleotides encoding a temperature sensitive transcription factors comprise DNA regulatory region regulated by binding of one or more temperature sensitive transcription factors.

In embodiments, wherein in addition to a cell specific promoter, one or more regulatory regions of the vector are selected to be cell specific, the vectors is configured to have the promoter and the regulatory regions controlling the expression of the chemogenetic gene, specifically recognized by the native synthetic machinery of the target brain cell.

For example, the expression vector and/or promoter can be selected to target controlling brain cell in hippocampus, which control formation of memory and can contribute to beginning of seizure activity, similarly area of temporal cortex and amygdala can also contribute to formation of seizures and reducing activity of activatory neurons (CamkIIa promoter) or inducing activity of inhibitory neurons (Parvalbumin positive neurons) can bring reduction of seizure frequency and severity. In dopaminergic cells in basal ganglia, upregulation of dopaminergic cell (tyrosine hydroxylase promoter) activity can be beneficial in treatment of Parkinson's disease. The same dopaminergic cells in ventral tegmental area can be activated to improve outcomes of mood disorders.

In some embodiments, wherein the target brain region is of microns dimensions the expression vector can comprise one or more regulatory regions which are in series with regulatory regions of the target brain cell in accordance with an intersectional approach.

The term "in series" as used herein refers to a connection between a regulatory regions and related regulatory molecule through biochemical reactions along a single linear circuit path.

An 'in-series' arrangement requires presence and activity of both regulatory regions independently activated or repressed in temporal succession, to obtain expression of the chemogenetic protein in the target brain cell.

Accordingly, in embodiments performed with an intersectional approach, the expression of the expression vector encoding the chemogenetic protein can be controlled by the activation or inhibition of at least another molecular component through direct or indirect reaction of the at least another molecular component with the expression vectors herein described.

In some embodiments, the individual is a transgenic animal engineered to express regulatory regions and/or corresponding molecules In a representative example, the transgenic animal can be a transgenic mice expressing Cre recombinase under a cell-specific promoter, to achieve cell-specific and circuit-specific expression of DREADDs. The Cre-recombinase system allows for the expression of a gene following delivery with a Cre-dependent viral vector only in cells expressing [45]. In those embodiments transfection can be performed unilaterally within the brain in a small cell population located deep within the midbrain and thus difficult to reach with traditional invasive approaches, and performed FUS mediated BBB opening applied to the midbrain concomitant with injection of a Cre-dependent AAV9-encoded hM3receptor (muscarinic receptor M3). The virus induced the activation of tyrosinehydroxylase-positive dopaminergic neurons of the midbrain in tyrosine hydroxylase (TH)-Cre transgenic mice following peripheral administration of CNO. After confirming successful viral infection by mCherry immunofluorescence, activation of the targeted neurons was measured by imaging c-Fos expression, an immediate early gene linked to neuronal activity that is commonly used as a marker of cellular activation. ATAC increased c-Fos activation CRE-expressing strain with the CRE activities restricted to one or more specific areas of the brain region. (see Example 5)

Embodiments performed with an intersectional approach allow delivery and expression of chemogenetic protein in target brain region of micrometer size.

In particular, in embodiments herein described, the type of vector (in view of related tropism to the target brain cell and transfer speed of from the blood stream to the target cells), the, the related elements of the vectors and configuration, and related concentration are selected to allow an expression level of the chemogenetic protein is sufficient for the chemogenetic to be able to activate or inhibit the activity of the target cell when in an operative state, such as expression levels allowing detectability of the target brain cell following the administering. [46]

In some embodiments, the type, configuration and concentration of the expression vector carrying the chemogenetic protein genes are selected to express the chemogenetic protein in at least 40% of the targeted gene population, where 40% constitutes cells that show delivery and expression of the chemogenetic proteins in the cells by, immunohistology or PET imaging.

In particular, the detection of expression of the expression vector can be achieved in vivo by introducing a chemogenetic ligand that has been radiolabeled and imaging it with positron emission tomography. This approach yields information about both quantitative levels of expression and the ability of a receptor to bind a specific ligand. In some individual such as research animals, immunostaining can be used to evaluate expression and proper subcellular localization of the receptors [11]. In those embodiments positive immunostaining is indicative that the genetic material encoding the chemogenetic protein has been successfully delivered to the cell. or other detection techniques.

The expression vector can be administered to the target region by routes of administration allowing the vector to be provide in blood of the individual, typically by intravenous injections.

In general, in embodiments herein described, the administration of the expression vector is performed to have a presence of vectors carrying genetic material in the blood concurrently with the occurrence of the BBB opening. In particular, the timing of the administration of the vectors with respect to the ultrasound application depends on the serum half-lives of the vectors. For vectors with short serum half-lives, the ultrasound application is performed within 10 minutes of the administration of gene delivery vectors. The injection can be performed either shortly before, or after, the focused ultrasound procedure. In some embodiments, the microbubbles and vectors are co-injected within 1 minute before the focused ultrasound procedure. Vectors with long serum half-lives can be injected longer than 10 minutes before the FUS-BBBO procedure.

In some embodiments, the administration of an expression vector encoding a chemogenetic protein to the target brain region can be simultaneously combined with or in sequential of the administration of the microbubbles.

In embodiments herein described, acoustically delivering to a target brain cell an expression vector herein described to provide a chemogenetically treated target brain region is performed in combination with administering to the individual a chemical actuator configured to switch the expressed chemogenetic protein conformation into the operative state.

In the method, the administering of the chemical actuator is performed for a time and under condition to allow binding of the chemical actuator or of a metabolite thereof with the expressed chemogenetic protein in the target brain cell of the chemogenetically treated brain region, and activation or inhibition of the target brain cell activity through stimulation of the target brain cell by the expressed chemogenetic protein in the operative state In some embodiments herein described the chemical actuator or metabolite thereof can be configured to be able to enter the brain from blood stream through BBB via a direct passage or via chemical alteration such as metabolism or prodrug conversion processes and then bind to the chemogenetic proteins. Examples of chemical actuators include CNO, compound 21, perlapine, clozapine or others identifiable to a person skilled in the art.

In some embodiments, chemical actuators are configured to cross through the BBB based on the lipid-mediated free diffusion. These drugs typically have a molecular weight below 500 Daltons and have fewer than 10 hydrogen bonds [16-18]. An example of such molecule is clozapine, which at low doses has limited side effects and can activate chemogenetic receptors of DREADD class.

In some embodiments, chemical actuators can be conjugates of molecules present in the body that naturally cross the BBB, such as amino acids or hexoses. Exemplary chemical actuators in this class include molecules having a binding affinity to GLUT1 and LAT1 transporters. The conjugates of a given molecule are defined as molecules having identical structures of the given molecule with exception of at least one atom or bond which are used to connect to another molecule.

Chemical actuators also include small molecule drugs capable of crossing the BBB through active transport by the transporters present in the BBB. Exemplary chemical actuators in this class include α-amino acids having a binding affinity to LAT1, LAT2, transporter (e.g. melphalan), or molecules that place the amino- and carboxyl-groups within 0.4 nm radius of the relative positions of these two functional groups in α-amino acids (e.g. gabapentin) in the solution structure of the molecule. Other exemplary chemical actuators include beta-amino acids and conjugates capable of crossing the BBB through pathways analogus to transport of beta-alanine, as well as other conjugates of amino acids that are actively transported through the BBB [19].

In some embodiments, chemical actuators can be fatty acids and their conjugates capable of crossing the BBB through fatty acid transporteras well as molecules passing through the BBB using transcytosis of engineered immunoglobulin or fusion proteins that bind to receptors present in the BBB[23].

Additional chemical actuators include protein or peptide therapeutics capable of crossing the BBB. Exemplary chemical actuators in this class include conjugates or protein fusions of antibody or antibody-fragments targeting endogenous protein transporters that are present in the BBB[19, 21], such as TfR, PepT1, PepT2, Oatp2, OAT-K1, OATP, and allow trans-BBB transport. Additional examples include other binding agents exhibiting affinity to the endogenous protein transporters present in the BBB, such as peptides evolved by directed evolution, or through in silico protein engineering methods[22].

In some embodiments, chemical actuators once administered to individual in an effective amount they can activate chemogenetic proteins by direct binding, which will cause a receptor agonism or antagonism[47] which can be identified by a skilled person upon review of the present disclosure in view of the specific actuator and chemogenetic protein and brain regions to be targeted.

For example Clozapine can be administered in doses up to 0.5 mg/kg to activate DREADD receptors, Clozapine-N-Oxide can be administered in doses up to 20 mg/kg for DREADD receptors; Compound 21 can be administered in doses up to 10 mg/kg, doxycycline can be administered in doses up to 20 mg/kg in research species, and up to 4.4 mg/kg in humans and non-human primates, Ivermectin can be administered in doses up to 400 micrograms/per kg to activate GluCl chemogenetic receptor) in humans and non-human primates; 200 micrograms to 10 mg per kg in mice and rats with a preferred dose of 500 mcg/kg).

In methods and systems herein described the chemical actuator can be administrated to an individual through various administration routes including oral ingestion, intravenous, intraperitoneal, or subcutaneous injections, inhalation, intranasal application and others as will be recognized by a person skilled in the art. In preferred embodiments, the chemical actuator can be administered by intravenous administration The chemical actuators can be in a form of an aqueous solution, solid powder, tablets, aerosols or other forms as will be understood by a person skilled in the art.

In some embodiments, administration of the chemical actuator is performed to chemogenetically treated target brain regions which are target brain regions where the expression vector of the disclosure has been delivered and the chemogenetic protein has been expressed.

Typical timing between applying focused ultrasound in combination with the administering the contrast agent and administering the expression vector of the disclosure, and expression of the chemogenetic protein in the target brain region is at least 1 week or later, to ensure BBB closure and allow gene expression in the brain cells.

In an exemplary embodiment, administration of the chemical actuator is first performed 6 to 8 weeks after the acoustically delivering herein described. Proof of concept shows efficacy at 6 to 22 weeks after acoustic delivery.

Conversion of the chemogenetic proteins from inactive to active, or from active to inactive state can be evaluated by measuring their levels of activity appropriate for the given receptors (e.g. histological levels of nuclear c-Fos protein for GPCR activation) or changes in membrane potentials through patch-clamping or electrophysiological recording in the brain for ion channels [12, 48].

In some embodiments of the methods and systems herein described, the focused ultrasound is applied with single and/or multi-element ultrasound transducers operating at frequencies between 0.2 and 10 MHz, and particularly between 1 and 10 MHz for rats and mice, and 0.2 to 1.5 MHz for non-human primates and humans. The mechanical index is maintained between 0.2 and 1.9, preferably between 0.2 and 0.6. Microbubbles are systematically administered prior to the application of the focused ultrasound at a concentration in the range of and 1.2E7-1E10 per kg of body weight of the individual. The methods further comprise before or after applying focused ultrasound, systematically administering a viral vector encoding a chemogenetic protein gene, preferably AAV and variants thereof, in a concentration between 1E9 and 1E12 viral particle per gram of body weight of the individual. The chemogenetic proteins can be kinases, non-kinase enzymes, G protein-coupled receptors (GPCRs). ligand-gated ion channels or transcription factors that can be recognized by a corresponding chemical actuator, which upon binding to the chemogenetic protein triggers the activation or inhibition of the targeted brain cells. The chemical actuator can be administered at least one week after the administration of the viral vectors. The methods and systems described herein can achieve in some embodiments the controlled percentage population of at least 40% and preferably at least 50% in the target brain region.

In some embodiments of the methods and systems of the disclosure chemogenetic protein and a corresponding chemical actuator or metabolite thereof are selected to activate or inhibit the activity of a target brain cell associated with the target behavior or physiological function of an individual.

In those embodiments, the applying, the systemically administering an effective amount of a microbubble contrast agent and the systemically administering an effective amount of an expression vector are performed to
deliver and express the gene encoding a chemogenetic protein in a controlled percentage population of the target brain cell in the target brain region associate with the target behavior or physiological function, and to obtain a chemogenetically treated target brain region in which the controlled percentage population of the target brain cell comprises the chemogenetic protein.

In preferred embodiments, the controlled percentage population is preferably at least 40% more preferably at least 50%.

In some embodiments of the methods and systems of the disclosure, chemogenetic protein and a corresponding chemical actuator or metabolite thereof are selected to activate or inhibit the activity of a target brain cell associated with treatment or prevention of a condition in the individual.

The term "treatment" as used herein indicates any activity that is part of a medical care for, or deals with, a condition, medically or surgically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" indicates a physical status of the body of an individual (as a whole or as one or more of its parts e.g., body systems), that does not conform to a standard physical status associated with a state of complete physical, mental and social well-being for the individual. Conditions herein described comprise disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms in an individual.

The term "neurological condition" refers to a condition of the central and peripheral nervous system, including the brain, spinal cord, cranial nerves, peripheral nerves, nerve roots, autonomic nervous system, neuromuscular junction, and muscles. These conditions include epilepsy, Alzheimer disease and other dementias, cerebrovascular diseases including stroke, migraine and other headache disorders, multiple sclerosis, Parkinson's disease, sequelae after neuroinfections or brain tumors and anti-tumor treatment, traumatic disorders of the nervous system due to head trauma, and neurological disorders as a result of malnutrition. Major types of neurological conditions include diseases or disorders caused by faulty genes, such as Huntington's disease, degenerative diseases, such as Parkinson's disease and Alzheimer's disease, seizure disorders such as epilepsy, cancer such as brain tumors, diseases of the blood vessels that supply the brain, such as stroke, and sequelae after infections such as meningitis. Other exemplary neurological conditions include epilepsy, headache, memory disorders, peripheral neuropathy, spinal cord tumor, and others identifiable by a person skilled in the art. Detailed information on neurological diseases can be found in related public sources such as MedlinePlus®, World Health Organization and other resources identifiable to a person skilled in the art.

Psychiatric conditions in the sense of the disclosure comprise any condition which arises from the dysfunctional activity of neural cells. Example conditions include major depressive disorder, eating disorders such as anorexia, and addiction. Detailed information on the types of psychiatric conditions can be found in related public resources such as the webpage of National Institute of Mental Health. [49-51]

In embodiments wherein chemogenetic protein and a corresponding chemical actuator or metabolite thereof are selected to activate or inhibit the activity of a target brain cell associated with treatment or prevention of a condition in the individual, the applying, the systemically administering an effective amount of microbubble contrast agents and the systemically administering an effective amount of an expression vector are performed to deliver and express the gene encoding a chemogenetic protein in a controlled percentage population of the target brain cell in the target brain region, the controlled percentage population associated with the treating or preventing of the condition in the individual, and to obtain a chemogenetically treated target brain region in which target brain cells of the controlled percentage population comprise the chemogenetic protein.

In preferred embodiments, the controlled percentage population is at least 40% preferably at least 50% or more at least 60% or at least 75%.

In some embodiments, the methods and systems herein described can be performed to treat mood disorders where dopaminergic cells can be modulated in ventral tegmental area, feeding disorders where food intake can be regulated by targeting AgRP/PoMC cells in arcuate nucleus, and Parkinson's disease where lack of dopaminergic signaling in SNC can be countered by stimulation of the cells efferent to SNC. The methods and systems can also be targeted on site of a seizure onset as defined by EEG source localization[52], or through MRI imaging[53].

Activation and inhibition of the specific neural circuits can be evaluated in subjects such as research animals and patients through behavioral evaluation. One can verify the functionality of the treatment by administering a drug and then performing a behavioral task affected by the circuit. A lack of side effects indicates activation of non-specific circuits. Additionally, the outcomes of the treatment can be quantified and the dose to achieve optimal benefit/side effect profile can also be tailored.

Activation of specific neural circuits can also be verified through noninvasive imaging such as fMRI, where the patterns of sites within the brain that change activity in response to ATAC and drug administration will yield information on the identity of activated circuits. Identification of activated circuitry through fMRI is commonly practiced [54-56] including the cases where drug administration induces localized changes in the brain activity and cases where neuromodulation is used to turn on specific circuits that are then monitored with fMRI[57].

In some subjects such as research animals, the activity of specific circuits can also be evaluated through invasive recordings or through histology [11].

In order to treat a neurological condition, targeted brain region are anatomically identified from general or patient specific tests to be involved in behavioral or disease that the treatment is designed to affect.

Such brain regions and cell populations are identifiable by their involvement in formation of the disease. One would first identify a disease to treat, then perform a search of a specific cell population up- or -downregulation of whose activity with a chemogenetic receptor, expressed under a cell-specific promoter, delivered in a vector delivered by an invasive injection caused modification of a behavior, or improvement of a disease outcome. Using a brain atlas, one would then identify this region in another species (e.g. human) and target that site with a combination of targeted FUS-BBBO, delivery of the same chemogenetic receptor, and the cell-specific promoter. For example, in our study we targeted a hippocampus, which is well known to a skilled person to be involved in formation of memory. By down-regulating activatory cells in hippocampus, we decreased the propensity of the hippocampus to consolidate new memories, as has been shown in our proof of concept.

In those embodiments, for each target brain regions at least 40% of neurons are transduced to affect the behavioral function and the disease outcome.

In some embodiments, the methods herein described are directed to treat Alzheimer's, epilepsy or other neurological and psychiatric conditions such as anxiety and the acoustic delivery of the expression vector is performed to a target brain regions of hippocampus as will be understood by a person skilled in the art.

Any target brain region of an individual that contains neurons that are alive and capable of expressing proteins can be targeted with FUS-BBBO and therefore can be targeted with methods and systems of the disclosure and related vectors and compositions. Additionally, the target brain regions have a BBB that is not permeable to AAVs and therefore the BBB is not disrupted to the point that AAVs can pass without help of the FUS-BBBO.

In some embodiments herein described, the methods and systems can be used to selectively stimulate or inhibit targeted neurons several weeks after the spatial targeting procedures (see Example 3).

In some embodiments herein described, when targeted on brain regions such as ventral and dorsal hippocampus, the methods have demonstrated specificity to the inhibition of memory formation while imposing minimal effect on exploratory behavior (Example 4).

In particular, a single injection of CNO several weeks after the FUS-BBBO procedure resulted in a 2.4-fold reduction in fear memory formation without any effects on normal exploratory behavior. In addition, both the cell types modulated in the chosen brain region and the polarity of the modulation can be chosen precisely using cell type-specific promoters and excitatory or inhibitory receptors (Example 4).

In some other embodiments, the methods and systems herein described have also shown compatibility with intersectional genetic targeting in transgenic animals, making it potentially useful in a wide variety of basic and disease model studies (Example 5).

In some embodiments, the expression vectors and contrast agent are comprised in a composition together with a compatible vehicle.

The term "vehicle" as used herein indicates any of various media acting usually as solvents, carriers, binders or diluents for the expression vectors, genes, contrast agent and/or chemical actuators herein described that are comprised in the composition as an active ingredient. In particular, the composition including the expression vectors, genes, contrast agent and/or chemical actuators can be used in one of the methods or systems herein described In some embodiments, the vehicle is a pharmaceutically acceptable vehicle and the composition is a pharmaceutically acceptable composition.

As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

The pharmaceutical preparations of an expression vector and chemical actuator can be given by forms suitable for each administration route. For example, pharmaceutical compositions comprising one or more chemical actuators can be formulated in tablets or capsule form, by injection, inhalation, eye lotion, eye drops, ointment, suppository, and additional forms identifiable by skilled person, administration by injection, infusion or inhalation; topical by lotion or ointment; and rectal by suppositories. The injection can be bolus or can be continuous infusion. Depending on the route of administration, a pharmaceutical preparation of a chemical actuator can be coated with or disposed in a selected material to protect it from natural conditions that can detrimentally affect its ability to perform its intended function.

The term "excipient" as used herein indicates an inactive substance used as a carrier for the active ingredients of a medication. Suitable excipients for the pharmaceutical compositions herein described include any substance that enhances the ability of the body of an individual to absorb the chemical actuators herein described or combinations thereof. Suitable excipients also include any substance that can be used to bulk up formulations with the one or more chlorate salts or combinations thereof, to allow for convenient and accurate dosage. In addition to their use in the single-dosage quantity, excipients can be used in the manufacturing process to aid in the handling of the one or more chlorate salts or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In some embodiments herein described, the expression vectors, genes, contrast agent and/or chemical actuators can be provided as part of a system to control neural circuits is described. The system can comprise expression vectors encoding a chemogenetic receptor gene, one or more chemical actuators, and optionally a contrast agent for simultaneous, combined or sequential use in the method to noninvasively control neural cell activities.

In preferred embodiments, a system of the disclosure, comprises any combination of a cell specific promoter, an expression vector, a chemogenetic actuator selected in view of the target brain cell and target brain region in effective amounts depending on the experimental design. In particular, in preferred embodiments the combination and effective amount can be selected to modify a target a target behavior or physiological function of an individual associated with a target brain cell activity with respect to a neural circuit of the individual. In preferred embodiments the combination and effective amount can also be selected to treat or prevent a condition associated with a target brain cell activity with respect to a neural circuit of the individual.

The systems herein disclosed can be provided in the form of kits of parts. In kit of parts for performing any one of the methods herein described, the expression vectors, genes, contrast agent and/or chemical actuators can be included in the kit alone in the presence of additional labels for the related detection as well as additional components identifiable by a skilled person.

In a kit of parts, the expression vectors, contrast agent and/or chemical actuators and additional reagents identifiable by a skilled person are comprised in the kit independently possibly included in a composition together with suitable vehicle carrier or auxiliary agents. For example, one or more expression vectors can be included in one or more compositions together with reagents for detection also in one or more suitable compositions.

Additional components can include labels, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure Embodiments of methods and systems herein described here described allow to specifically and/or selectively activate or inhibit the target brain cell activity and in preferred embodiments, to modify an existing behavior and/or physiology of the individual associated with the target brain cell activity, through the specific and/or selective activation or inhibition of the target brain cell of the target circuit.

The wording "specific" "specifically" as used herein with reference to activation or inhibition of brain cells activity refers to activation or inhibition of activity in targeted brain cells with substantially less to no expression in other populations of brain cells.

The wording "selective" "selectivity" refers to the ability of the methods and systems herein described to particularly choose among various regions, neural circuits, cells, and pathways while filtering out the others.

In particular in several embodiments, the methods and systems herein described can achieve noninvasive neuromodulation with a unique combination of spatial, cell-type and temporal specificity. Accordingly, methods and systems herein described do not require multiple brain penetrations to cover the desired area (up to dozens in larger species[6, 7]), FUS-BBBO enables comprehensive transduction of an entire brain region in a single session with relatively minimal tissue disruption, and can more easily be scaled to larger animals and humans.

Additionally compared to emerging ultrasonic neuromodulation techniques in which ultrasound directly activates or inhibits brain regions or locally delivers neuromodulatory compounds[58-66], methods and systems herein described do not require an ultrasound transducer to be mounted on the subject during modulation. After transduction and expression of chemogenetic receptors in a genetically defined subset of cells at the FUS-targeted site, neuromodulation can be controlled using a systemically bioavailable chemical actuator. The fact that a single FUS-BBBO session is sufficient to perform a desired regulation of a target brain cell activity, also minimize the potential for non-specific cellular-level effects seen after multiple FUS-BBBO treatments[67, 68].

In particular in embodiments wherein transfection of more than 40% of the target cell population in a target brain region is performed, a robust modulation of the brain region of interest can be achieved (see e.g., Examples section and FIG. 15A) more robust of modulation achievable with existing methods. In addition, in methods and systems of the disclosure transfection of a high percentage of population is achieved without major tissue damage. Achieving a consistent robust modulation of brain regions while minimizing tissue damage is surprising in view of existing approaches. Existing approaches typically require high ultrasound intensities, to achieve a BBB opening suitable to deliver vectors in size and amount for an effective expression of chemogenetic proteins leading to tissue damage [69], or are typically accompanied by unquantified gene expression levels and/or inconsistent chemogenetic expression in a percentage population of target brain cell above 40% if low ultrasound intensity is selected to minimize tissue damage[70-75]. Tissue damage is defined as damage with a volume occupying less than 0.1% of the volume targeted with focused ultrasound (and in most cases, no damage at all). For comparison, this volume is between more than 30-fold smaller than the size of needles used for direct injection into the brain in mice (which would be larger in larger species).

Additionally, in embodiments herein described a delivery and expression of chemogenetic protein can be achieved minimizing tissue damages, in at least 40% of the target cell population of selected target brain regions (e.g. hippocampus, CA2 and CA3, in Example 3 of the instant disclosure)

Furthermore methods and systems herein described allow control of a specific cell population in the brain minimizing significant expression of the chemogenetic protein in the peripheral nervous system (PNS), so as to avoid undesirable systemic effects. Methods and systems herein described allow achieving the goal of efficient brain transfection of targeted regions while minimizing transfection of PNS neurons, as exemplified by the dorsal root ganglia of Example 2 (FIG. 8) and Example 5 (FIG. 11) of the present disclosure.

A skilled person will be able to identify suitable combination of vector concentrations and ultrasound frequency taking into account vascularization of the target region, viral tropism and transfer speed of a vector from the blood brain barrier to the target brain region, all factors that may require higher doses as will be understood by a skilled person.

EXAMPLES

The, methods and systems herein disclosed and related vectors and compositions are further illustrated in the following examples, which are provided by way of illustration and are not intended to be limiting.

In particular, the following examples illustrate exemplary methods and systems to control a target brain cell activity with respect to a target neural circuit of an individual. A person skilled in the art will appreciate the applicability and the necessary modifications to adapt the features described in detail in the present section, to additional methods and systems and related vector and compositions, according to embodiments of the present disclosure.

The following materials and methods were used.

Animals:

C57BL6J mice were obtained from JAX laboratories. Transgenic TH-CRE mice were obtained from a Caltech's internal colony, and were originally generated [76] at Uppsala University, Sweden. Animals were housed in 12 hr light/dark cycle and were provided water and food ad libitum. All experiments were conducted under a protocol approved by the Institutional Animal Care and Use Committee of the California Institute of Technology.

FUS-BBBO:

Male, 13-18 week old C57BL6J mice were anesthetized with 2% isoflurane in air, the hair on their head removed with Nair depilation cream and then cannulated in the tail vein using a 30 gauge needle connected to PE10 tubing. The cannula was then flushed with 10 U/ml heparin in sterile saline (0.9% NaCl) and affixed to the mouse tail using tissue glue. Subsequently, mice were placed in the custom-made plastic head mount and imaged in a 7T MRI (Bruke Biospec). A FLASH sequence (TE=3.9 ms, TR=15 ms, flip angle 20 degrees) was used to record the position of the ultrasound transducer in relation to the mouse brain. Subsequently, mice were injected via tail vein with AAV9 (1E10 viral particles (VP)/g) encoding DREADDs: pAAV-CaMKIIa-hM4D(Gi)-mCherry (Addgene plasmid #50477) or pAAV-CaMKIIa-hM3D(Gq)-mCherry (Addgene plasmid #50476), both plasmids a gift from Bryan Roth.

Immediately after viral injection, the mice were also injected with approximately 1.5E6 of Definity microbubbles (Lantheus) and 0.125 µmol of Prohance (Bracco Imaging) dissolved in sterile saline, per g of body weight. The dose of Definity was optimized through preliminary studies from a starting point obtained from literature[77]. The dose of Prohance was based on the manufacturer's recommendations. Within 30 seconds, the mice were insonated using an 8-channel focused ultrasound system (Image Guided Therapy, Pessac, France) driving an 8-element annular array transducer with a diameter of 25 mm and a natural focal point of 20 mm, coupled to the head via Aquasonic gel. Gel was placed on the top and both sides of the animal's head to minimize reverberations from tissue-air interfaces.

The focal distance was adjusted electronically as shown in FIG. 14 to target specific brain regions. The ultrasound parameters used were 1.5 Mhz, 1% duty cycle, and 1 Hz pulse repetition frequency for 120 pulses and were derived from a published protocol[78]. The pressure was calibrated using a fiber optic hydrophone (Precision Acoustics, UK), with 21 measurements and an uncertainty of ±3.8% (SEM). The pressure chosen for FUS-BBBO was based on multiple studies[78, 79] and preliminary experiments in our lab. The ultrasound parameters were 1.5 MHz, 0.42 MPa pressure accounting for skull attenuation (18%[80]), 1% duty cycle, and 1 Hz pulse repetition frequency for 120 pulses. For each FUS site, Definity and Prohance were re-injected before insonation.

After FUS-BBBO, the mice were imaged again using the same FLASH sequence to confirm opening of the BBB and appropriate targeting. Immediately afterwards, mice were placed in the home cage for recovery. The TH-CRE animals, aged 18 weeks, were subjected to FUS-BBBO using the same protocol, and using the same dose of AAV9, as for C57BL6J mice. All TH-CRE animals were females.

MRI images were analyzed using imagej measurement function. To estimate size of the BBB opening, a single FUS-beam using standard parameters was used. The hyperintense area from Prohance extravasation was delineated manually and the dimensions of minor and major axis recorded for n=7 animals. The volumes were calculated assuming ellipsoid shape. For Mill intensity calculation, the 4 sites of FUS-BBBO in dorsal hippocampus were delineated manually and average signal intensity calculated within the region for each mouse. The result was then divided by a mean signal intensity in an untargeted thalamus 1.5-2 mm below hippocampus. The result was then compared to the size of an ultrasound beam Intracranial Injection:

Solutions AAV9 encoding hM4Di-mCherry under a CamkIIa promoter were injected into the hippocampus of male C57BL6J mice (Jackson Laboratory) at 18 weeks of age using a Nanofil blunt-end 33 g needle coupled with a motorized pump (World Precision Instruments) at 100 nl min$^{-1}$ using a stereotaxic frame (Kopf). The coordinates of the two pairs of sites with respect to bregma were −2.2 mm anterior-posterior, ±2 mm medio-lateral, −1.7 dorso-ventral and −3.2 mm anterior-posterior, ±3.5 mm medio-lateral and −3 mm dorso-ventral. The needles remained in place after injection for 5 min to avoid backflow along the needle tract. The total volume of injection used was 500 nl. The total viral load was 5E8 in 0.5 µl per each site, following previously published dosing [81], and 7 weeks was allowed for expression to match the timeline used for analysis of expression and damage following FUS-BBBO.

C-Fos Activation and Immunostaining:

C57BL6J male mice of 13 weeks of age underwent FUS-BBBO to administer AAV9 carrying hM3Dq-mCherry into the hippocampus. Subsequently, mice were housed singly to reduce background C-fos expression. After 22 weeks of expression, mice received an IP injection of 1 mg/kg CNO in sterile saline, and were returned to home cages. After 150 minutes, mice were anesthetized using Ketamine/Xylazine solution (80 mg/kg and 10 mg/kg, respectively, in PBS) and perfused with a cold PBS/Heparin (10 U/ml), and immediately afterwards with 10% Neutral Buffered Formalin (NBF). Their brains were extracted and post-fixed in 10% NBF for at least 24 hours. Brain sections (50 µm) were obtained using a VF-300 compresstome (Precisionary Instruments). Subsequently, sections were blocked in 10% Normal Donkey Serum and 0.2% Triton-X solution in PBS for 1 hr in room temperature, and immunostaining with primary antibody was performed using a goat anti-c-Fos antibody (SC-253-G, SCBT, Santa Cruz, Calif.) in 10% Normal Donkey serum and 0.2% Triton-X, overnight at 4° C. Afterwards, sections were washed three times in PBS and incubated with a secondary donkey anti-goat antibody conjugated to Alexa-488 (A-11055, Thermofisher).

For activation of hippocampus, the histological evaluation was performed by an observer blinded to the identity (hM3Dq positive, or negative) of granular layer nuclei in dCA3. The expression status of the neurons was determined after the scoring of c-Fos positivity. The activation of TH neurons was evaluated by an observer blinded to the presence of FUS-BBBO targeting at a given site. TH-CRE mice expressed hM3Dq for 9 weeks after FUS-BBBO, and then were given 1 mg/kg CNO. After 2 h, they were anesthetized with ketamine/xylazine (80/10 mg/kg in PBS) and perfused using cold heparine/PBS (10 u) and then 10% NBF. At least two sections per animal were used for c-Fos immunostaining of hM3Dq activation experiments, and all of the pyramidal neurons (for hippocampus experiments) or TH cells (for intersectional ATAC experiments) within each section were used for analysis. The saline control of c-Fos activation experiments in intersectional ATAC used one section per mouse and all TH cells within each section were used for analysis. A three-dimensional reference atlas[82] was used to choose the appropriate regions and brain sections for each mouse and contralateral and ipsilateral controls to ascertain consistency in choice of analyzed sections. One region of interest in 1 out of 6 TH-CRE mice was damaged during sectioning and the mouse couldn't be included in c-Fos evaluation. The timepoints chosen for c-Fos testing were based on previous literature[83, 84].

Gene Expression Evaluation:

The gene expression timeline was chosen based on previous studies indicating that expression of genes delivered with AAV9 is stable after 6 weeks[85], and showing activity of DREADDs after that time point[86, 87]. In addition, the long-term expression of 22 weeks in FIG. 4 was chosen to establish if DREADDs remain active after a longer period of time following FUS-BBBO delivery.

To visualize DREADD expression across brain regions, immunostaining was used with a polyclonal rabbit anti-mCherry antibody (PA534974, Thermofisher), a polyclonal goat anti-CaMKIIa antibody (PA519128, Thermofisher) and a polyclonal goat anti-Gad67 (Lifespan, 103220-296) antibody in 10% Normal Donkey Serum (NDS, D9663-10ML, Sigma-Aldrich) and 0.2% Triton-X in PBS, overnight at 4° C. The TH expression was evaluated using an anti-TH chicken antibody (TYH, Ayes lab) incubated in normal Goat Serum (NS02L-1ML, Sigma-Aldrich) and 0.2% triton-x in PBS at 4° C., overnight. The expression of PGP9.5 was evaluated using rabbit anti-PGP9.5 (Abcam, ab10404), incubated in 0.2% Triton-x in PBS at 4° C., overnight. Secondary antibodies were donkey anti-rabbit conjugated to Dylight-650 (#84546, ThermoFisher), donkey anti-goat conjugated to Dylight-488 (SA510086) and goat anti-chicken conjugated to Alexa 488 (A-11039, ThermoFisher). Secondary antibodies were incubated in 10% NDS/0.2% triton-x in PBS for 4 h at room temperature.

For quantitative comparison of expression levels between various regions of the hippocampus, mCherry fluorescence localized to cytoplasmic compartments was used and the number of cells in the pyramidal layers of hippocampus showing detectable fluorescence was counted. Cells were co-stained with a nuclear stain (DAPI) to allow delineation of nuclei and surrounding cytoplasmic regions. Cells that showed mCherry fluorescence surrounding the nucleus for at least 50% of its circumference were counted as positive to allow for a consistent comparison of expression between different hippocampal regions and conditions. The non-cytoplasmic localization of DREADD-mCherry necessitated the selection of this threshold.

All the images were background-normalized to allow for comparable evaluation of expression. Sections were obtained at 50 μm serially, in order. All sections were inspected for expression at a low-power fluorescent microscope and representative sections were then imaged on a confocal microscope. Expression was evaluated for 3-5 sections per animal, and cells from each subfield of hippocampus were added for each animal and normalized by a number of DAPI cells in the granular cell layer of that field. The inter-experimenter variability was determined for two different researchers (B.L., J.O.S), for n=6 samples, with the difference in means smaller than 2.5% (mean=42.5% vs 41.5%, p=0.92, heteroscedastic,two-tailed, t-test).

Behavioral Testing:

Behavioral studies for fear conditioning were performed in sound-attenuated fear conditioning chambers (30×25×25 cm, Med Associates). Animals were trained and tested for context fear in Context A, which comprised a staggered wire grid floor, white light, 5% acetic acid for scent and no background noise. Locomotor testing was performed in Context B, which was differentiated from Context A by chamber shape, floor, illumination, odor, background noise and room location. Animal activity was recorded and quantified using Video Freeze software (Med Associates). For cued training, the tone was 80 dB and 30s.

Fear Conditioning:

Mice were injected with CNO (10 mg/kg, IP) or saline (IP), and after 40-60 minutes underwent context and cued fear conditioning in Context A. This timeframe was chosen to allow CNO to reach its pharmacokinetic peak[88]. A 3-minute initial baseline period was followed by 3×30-s presentations of a tone co-terminated with a 2-s foot shock (0.7 mA), with inter-trial interval of 60 s. After the trials, the mice remained in the context for an additional 60 s, after which they were transported back into the vivarium. After 24 h, mice were placed in Context A to record context fear for the duration of training (8 min. and 40 s).

Exploratory Behavior Analysis:

Between 30 and 45 minutes after the context fear test, mice were transported to another room, placed in Context B and allowed to explore the chamber for 3 minutes while their activity was recorded. Due to automated data acquisition and evaluation, no blinding was necessary.

Fear Conditioning Analysis:

Mice were recorded using automated near-infrared video tracking in the fear conditioning chamber using VideoFreeze software. Mouse motion was measured using the activity score, from a video recording at 30 frames/s, with the motion threshold set at 18 activity units (standard value set in software). Freezing was defined as an activity score below 18 units for at least 1 s. Average freezing in the context test was scored over the whole trial. Due to automated data acquisition and evaluation, no blinding was necessary.

Exclusions:

mice were excluded from statistical analysis if their histologically determined DREADD expression was below 30% of cell bodies in dorsal CA3 region of the hippocampus. This threshold was chosen based on previous studies showing that behavioral effects generally require modulation of at least 30% of the neurons in a targeted region[89, 90] and dorsal CA3 being the most robustly transfected hippocampus region. The resulting analyzed groups had identical levels of expression (55.1% for Saline and 60.5% for CNO groups, p=0.26, heteroscedastic, two-tailed, t-test). In analyses including all mice, we found that DREADD expression in dorsal CA3 correlated with the formation of context fear memories in mice treated with CNO (r=0.62, n=11) but not in mice receiving saline (r=0.14, n=14) (FIG. 15, panel a). Even without excluding the four mice who had expression below 30%, a direct comparison between ATAC mice treated with CNO and saline showed a statistically significant reduction of context fear (53.2 vs 34%, n=13, 11; p=0.0193; heteroscedastic, two-tailed, t-test). Variability in gene expression may have been due to variability in intravenous injections of virus during the FUS-BBBO procedure, since we found no difference between these mice in $T_1$ MRI signal enhancement post FUS-BBBO (FIG. 15, panel b).

Statistical Analysis:

Data was analyzed using either two-tailed t-test with unequal variance (when two samples were compared and when data was deemed normal with Shapiro-Wilk test) or one-way ANOVA with a Tukey HSD post-hoc test (when more than two samples were compared).All data with p<0.05 were considered significant. Error bars used throughout the study represent standard error of mean (SEM). "*" Corresponds to p<0.05, "*" to p<0.01 and "***" to p<0.001. All data was tested for normality using Shapiro-Wilk test. Samples with two conditions and non-normal distributions were tested by a nonparametric test (Mann-Whitney). All central tendencies reported are averages.

Histological Analysis:

Analysis of the FUS-BBBO safety was performed using hematoxylin staining and autofluorescence. All of the vibratome sections (50 micron) within the hippocampus were imaged under 10× objective under microscope to identify potential lesions (n=14 mice). The sections showing largest anomalies were then observed in a greater magnification (20× objective). The FUS-induced lesions were autofluorescent and fluorescence microscopy was used for measurements. The volumes were calculated assuming ellipsoid shape of the damage, with maximum diameters within a section used for major and minor axes. The volume of lesions was calculated using ellipsoid volume formula (v=4/3×π×(width/2)$^2$×length/2). To confirm the anatomy of the lesions, hematoxylin staining was performed: vibratome sections were stained for 30-45 seconds in 20% Gill no. 3 hematoxyllin, followed by a brief wash in PBS and 5 second dip in RapidChrome blueing solution (Thermofisher). Each section was then washed twice in PBS and mounted in a water-based medium (ProLong Gold, Thermofisher).

Figure 1:
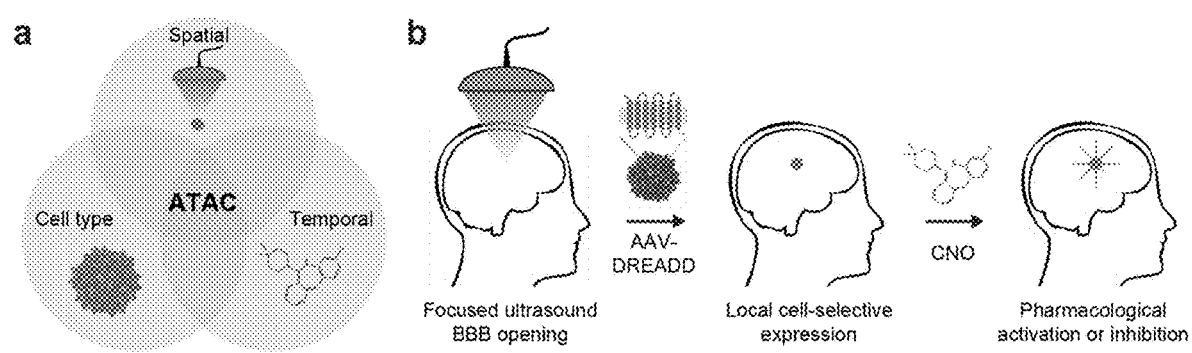
FIG. 1 shows a schematic providing an exemplary illustration of the acoustically targeted chemogenetics (ATAC) paradigm. In particular FIG. 1, Panel (a) provides a schematic illustration of the combination of effects surprisingly associated with the ATAC methods and systems herein described. The ATAC paradigm provides a combination of millimeter-precision spatial targeting using focused ultrasound (spatial), cellular specificity using viral vectors with cell type-specific promoters driving the expression of chemogenetic receptors (cell type), and temporal control via the administration of the chemogenetic ligand (temporal.

Illustrations:

The structure of AAV9[91] in FIG. 1 has been rendered using QuteMol[92]. The 3D rendering of hippocampus in FIG. 2 was generated using Rhinoceros 3D software with models obtained from 3D brain atlas reconstructor[93] and waxholm space dataset[94].

Example 1: ATAC Paradigm

In methods and systems herein described and related approach, herein also indicated as acoustically targeted chemogenetics (ATAC) combines focused-ultrasound blood-brain barrier opening ("FUS-BBBO") employed for spatially targeting a specific region in the brain, expression vectors for the delivery of genes of interest to specific cell types in a target region, and chemogenetic receptors for modulation of targeted neurons upon activation by a chemogenetic receptor FIG. 1 illustrates a schematic of acoustically targeted chemogenetics (ATAC) paradigm. As shown in FIG. 1, panel (a), the ATAC paradigm provides a combination of millimeter-precision spatial targeting using focused ultrasound, cellular specificity using expression vectors with cell type-specific promoters driving the expression of chemogenetic receptors, and temporal control via the administration of the chemogenetic actuator/ligand. As shown in panel (b), in the ATAC sequence, the blood-brain barrier (BBB) is opened locally using focused ultrasound, and systemically injected an expression vector such as adeno-associated virus (AAV) encoding a chemogenetic receptor such as designer receptor exclusively activated by designer drug (DREADD) enters the treated area. After a period of time (e.g. several weeks), the chemogenetic receptor is expressed in the targeted region in cells possessing selected promoter activity. At any desired subsequent time, the DREADD-expressing neurons can be excited or inhibited through a chemogenetic drug such as clozapine-n-oxide (CNO).

Example 2: Anatomical and Genetic Targeting of DREADD Expression

Figure 2:
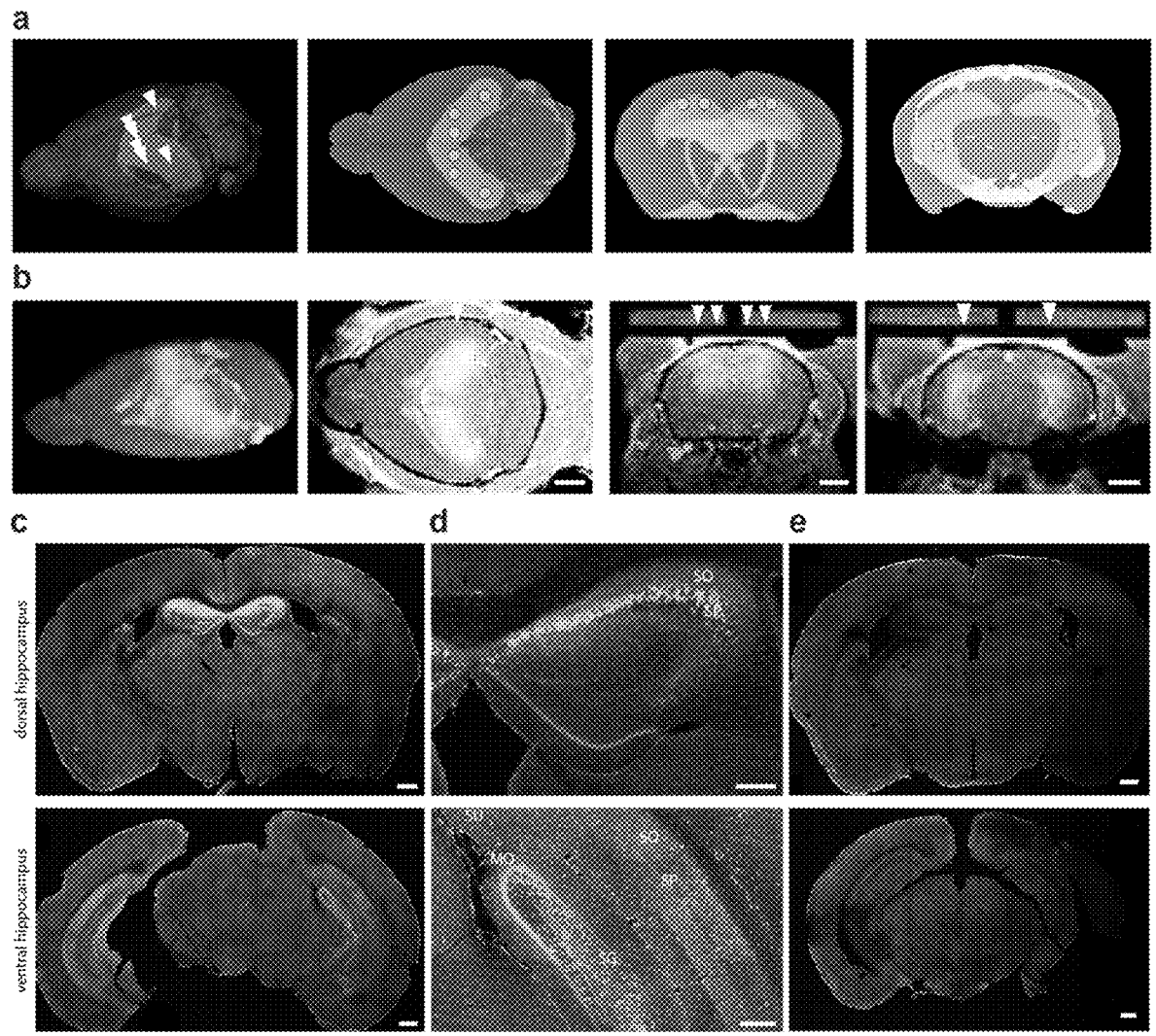
FIG. 2 shows images reporting an exemplary opening of blood-brain barrier and targeted expression of DREADD in the hippocampus.

To evaluate the ability of ATAC to target the expression of DREADDs to a specific location in the brain, FUS-BBBO was first performed on the hippocampus of wild-type mice. The hippocampus is a brain region involved in memory formation and implicated in several neurological and psychiatric diseases, including anxiety, epilepsy and Alzheimer's[95]. To achieve expression throughout this brain structure, FUS-BBBO was performed at 6 locations covering the ventral and dorsal hippocampus using an MRI-guided focused ultrasound instrument operating at 1.5 MHz (FIG. 2, panel a). FUS was applied immediately after an intravenous injection of microbubbles and viral vector, with a gadolinium contrast agent co-administered to visualize regions with successful BBBO (FIG. 2, panel b). AAV9, a serotype of AAV with favorable tropism for neurons and large spatial spread after direct intracranial delivery[96], was selected as the viral vector. This vector encoded the DREADD receptor hM4Di, fused to the fluorescent reporter mCherry to facilitate histological visualization. This gene was encoded downstream of a CaMKIIa promoter, which was used to target ATAC specifically to excitatory neurons[97].

After allowing 6-8 weeks for transgene expression, the targeted locations showed widespread hM4Di expression in histological sections, covering most hippocampal regions and a small segment of cortex above the dorsal hippocampus (FIG. 2, panel c). Expression was especially strong in the molecular and polymorph layers of dentate gyrus (DG), the stratum oriens and stratum radiatum of the CA1, CA2 and CA3 fields, as well as the pyramidal cells of the DG, CA2, and CA3 (FIG. 2, panel d). Expression was present broadly throughout the hippocampus (FIG. 7).

By comparison, mice that received an intravenous injection of the same AAV9 vector without FUS-BBBO showed essentially no fluorescent signal in these brain regions (FIG. 2, panel e), confirming that BBBO was required for gene delivery at the viral dose used in this study.

To assess the possibility of off-target expression in the peripheral nervous system immunostaining was performed against hM4Di-mCherry in dorsal root ganglia (DRG). No expression of DREADDs was found (FIG. 8) in DRG, consistent with another study showing poor efficiency of peripheral nerve transduction with AAV9[98].

Figure 3:
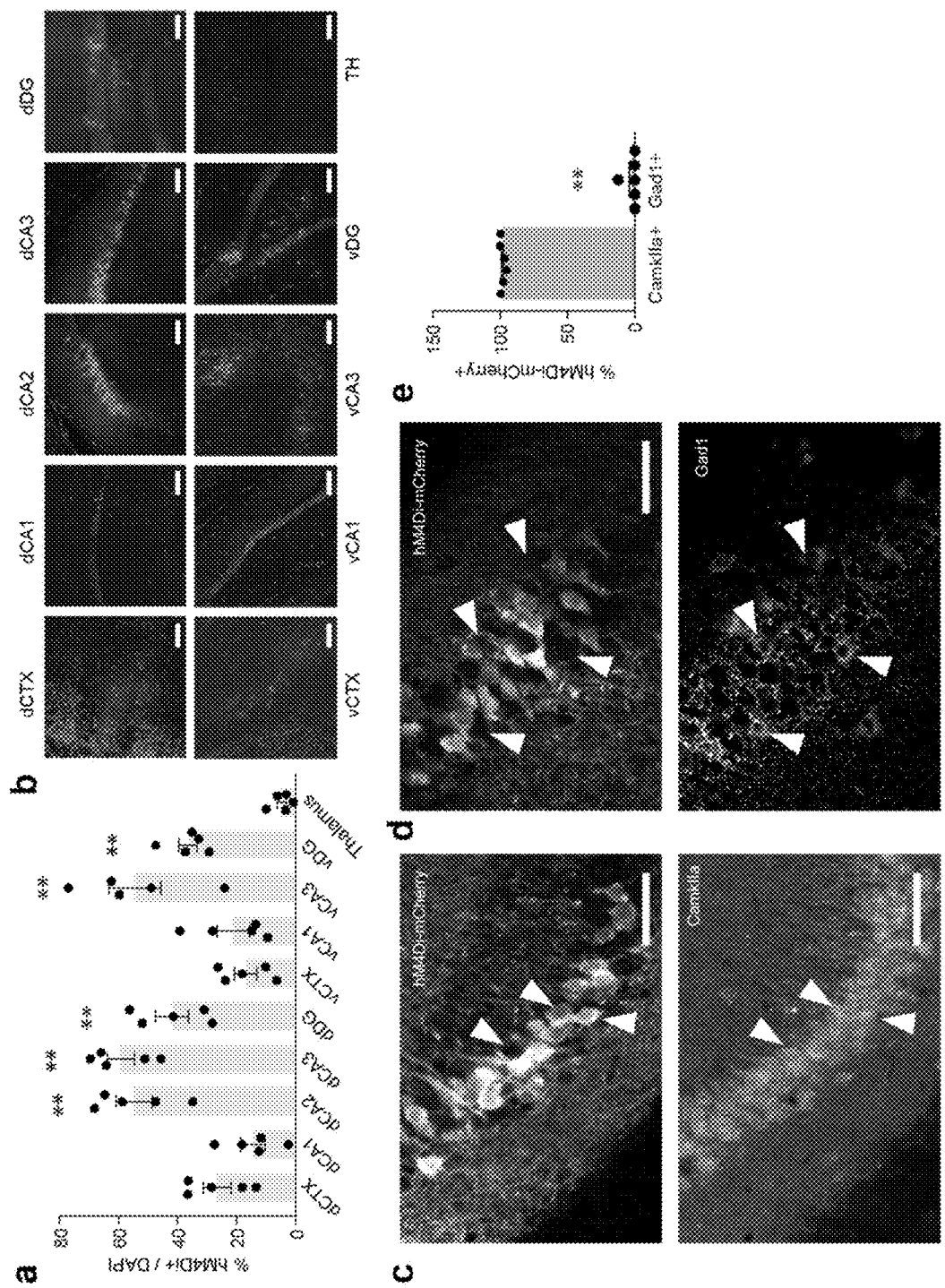
FIG. 3 shows graphs and images reporting spatial and cell type specificity of an exemplary DREADD expression.

A quantitative comparison of expression in FUS-targeted areas across 5 mice was performed using mCherry fluorescence in cell bodies of granular cell layers, which allowed for a direct comparison of transfection efficiency between hippocampal regions. The analysis showed that more than 50% of the cells in dorsal and ventral CA3 and dorsal CA2 were successfully transfected, and that ventral and dorsal DG contained 42% and 36% positive cell bodies, respectively (FIG. 3, panel a-b). Cortex and CA1 typically had lower transfection efficiencies, suggesting that these regions are less susceptible to transfection after BBBO than other hippocampal fields. As a representative non-targeted region, the expression in the thalamus was further investigated, which was shown in previous studies to be particularly susceptible to transfection following systemic delivery of AAV9[42], and found no significant expression (<5%, FIG. 3, panel a-b). Full results of the statistical tests can be found in Table 3.

In particular, Table 3 below shows the results of the one-way ANOVA with Tukey HSD post-hoc test comparing susceptibility of transfection of different fields of hippocampus with FUS-BBBO compared to a negative control (untargeted thalamus). (v—ventral and d—dorsal). n=5 mice tested for each condition

TABLE 3

Comparison of susceptibility of transfection of different fields of hippocampus with FUS-BBBO compared to a negative control (untargeted thalamus)

| Hippocampus field | Tukey HSD Q-statistic | p-value | inference |
| --- | --- | --- | --- |
| dCTX | 4.2469 | 0.111836 | insignificant |
| dCA1 | 1.9 | 0.899995 | insignificant |
| CA2 | 9.7486 | 0.001005 | **p < 0.01 |
| dCA3 | 10.6203 | 0.001005 | **p < 0.01 |
| dDG | 7.2205 | 0.001005 | **p < 0.01 |
| vCTX | 2.3802 | 0.773106 | insignificant |
| VCA1 | 3.1823 | 0.444716 | insignificant |
| vCA3 | 9.6811 | 0.001005 | **p < 0.01 |
| vDG | 6.1661 | 0.003168 | **p < 0.01 |

When compared to a direct intracranial injection of the same genetic construct using established protocols[81], the percentage of mCherry positive cell bodies at the sites of injection was similar to regions strongly expressing the construct after FUS-BBBO (52.8±10.1%, n=4 mice, and 8 injections analyzed, FIG. 9).

To evaluate the cellular specificity of genetic targeting, expression of DREADDs in cells staining positively for CaMKIIa or Gad1 was compared, which serve as labels of excitatory and inhibitory neurons, respectively (FIG. 3, panel c-d). It was found that 98.4±0.8% of the cells expressing the DREADD receptor also stained positively for CaMKIIa, while only 2.08±2.08% of these cells co-stained for Gad1, confirming selective targeting of the constructs to excitatory neurons (n=6, p=4.75E-9, heteroscedastic, two-tailed, t-test FIG. 3, panel e).

Example 3: Targeted Stimulation of the Hippocampus

Depending on the DREADD encoded in the AAV vector, ATAC can be used to either stimulate or inhibit targeted neurons. To first assess the ability of this technique to provide cell-specific activation, AAV9 carrying the excitatory DREADD hM3Dq-mCherry, under the CaMKIIa promoter, was targeted to the dorsal hippocampus using 4 FUS-BBBO sites. After allowing time for expression, CNO intraperitonealy (IP) was administered and 2.5 hours later the mice was perfused to histologically monitor the expression of the activity-dependent gene product c-Fos in the dorsal CA3 region of the hippocampus (FIG. 4, panel a).

It was found that cells positive for hM3Dq expression were 5.8 times more likely to exhibit c-Fos staining than cells not expressing hM3Dq (FIG. 4, panel b, c, n=6, p=7.1E-4, two-tailed, paired t-test), indicating that systemic chemogenetic treatment allows ATAC-targeted neurons to be selectively activated several weeks after the spatial targeting procedure.

Example 4: Targeted Inhibition of the Hippocampus and Effect on Memory Formation To assess the ability of ATAC to inhibit targeted neurons, and to test the functionality of this technology in a behavioral paradigm, FUS-BBBO was used to target inhibitory DREADDs (hM4Di) to ventral and dorsal hippocampus (FIG. 5, panel a), and the impact of CNO administration on the formation of contextual fear memories was assessed. This well-established behavioral paradigm has been used in studies of anxiety, phobias, PTSD and fear circuitry[99]°[100]. Fear conditioning has also served as a testing ground for other novel neuromodulatory techniques[81, 101]. Since the hippocampus plays an essential role in memory formation, it is hypothesized that inhibiting it noninvasively using the ATAC strategy would reduce the ability of mice to form fear memories.

Coverage of the hippocampus was achieved with FUS-BBBO applied to 6 sites (FIG. 2), accompanied by intravenous administration of AAV9 containing hM4Di-mCherry under the CaMKIIa promoter, to obtain ATAC mice. Two groups of control mice were either completely untreated or received intravenous virus without FUS-BBBO. After 6-8 weeks, the mice underwent a fear conditioning protocol (FIG. 5, panel a). In this protocol, the mice are placed in a unique environment (defined by chamber shape, lighting, smell and sound; Context A in FIG. 5, panel a) while receiving three electric foot shocks, causing them to associate this environment with the noxious stimulus in a process known as context fear conditioning. 40-60 minutes before undergoing this protocol, each group of mice received injections of either CNO or saline to test the ability of targeted inhibition of ATAC-treated hippocampal neurons to reduce fear formation.

24 hours after conditioning, contextual fear recall was tested by placing mice in the same context and measuring freezing, an indication of fear[102] (FIG. 5, panel a). ATAC mice treated with saline during conditioning froze 53.2% of the time, indicating robust fear recall. By contrast, ATAC mice that received CNO before conditioning froze only 21.8% of the time—a more than 2-fold reduction in fear memory (p=1.9E-5; n=13 and 7, heteroscedastic, two-tailed, t-test). (FIG. 5, panel b). Comparing these two FUS-treated conditions to each other allowed us to evaluate the efficacy of ATAC while accounting for any potential behavioral effects caused by the FUS treatment itself[103, 104].

Additional controls showed that the activation of any DREADDs potentially expressed outside FUS-targeted brain regions (after a systemic AAV9 injection, but in the absence of FUS-BBBO), or CNO treatment alone in wild-type mice, did not result in a reduction in context fear relative to untreated controls (FIG. 5, panel c, d). To confirm that the effect of activation of DREADDs was specific to fear formation, and did not affect basic exploratory behavior, treated and untreated mice were monitored in an open field test. One day after fear conditioning, the mice were placed in a novel environment (Context B in FIG. 5, panel a), which they were allowed to explore freely for 3 minutes. The exploratory behavior of all groups of mice was likewise unaffected by CNO administration (FIG. 5, panel e-g).

To confirm that the effect of ATAC treatment was specific to inhibiting memory formation as opposed to sensation of stimuli such as pain, each foot shock with an audible tone was paired to produce an association between the tone and the shock in a process known as cued conditioning (FIG. 10). This process takes place immediately during training, and is not expected to be affected by inhibition of memory-forming regions of the hippocampus[81]. As expected, cued freezing measured at the end of the training session was unaffected by CNO treatment (FIG. 10, panel b-d), indicating that ATAC-treated mice were not compromised in their ability to experience salient sensory stimuli.

Example 5: Intersectional ATAC in Transgenic Animals

In addition to its potential therapeutic applications, ATAC may facilitate the study of neurological and psychiatric disease mechanisms in animal models by making it possible to modulate disease-related spatially defined neural circuits without surgery. A complementary resource for such studies is the large number of transgenic mouse and rat lines available with cell type-specific expression of the CRE recombinase. The delivery of a viral vector encoding any gene of interest in a CRE-dependent configuration allows the expression of this gene to be confined to the CRE-expressing cells in that animal[105].

To test whether ATAC could be used in combination with a CRE mouse line to provide noninvasive spatial and cell-type targeting of neuromodulation, FUS-BBBO was used to deliver a CRE-dependent DREADD construct into TH-CRE transgenic mice[76]. These animals express the CRE recombinase in tyrosine hydroxylase-positive dopaminergic neurons in the midbrain, especially in the substantia nigra pars compacta (SNc) and the ventral tegmental area (VTA). These regions are researched extensively in models of Parkinson's disease, addiction and reward and have previously been used to validate new neuromodulation techniques[106]. Due to their locations deep within the brain and their small size, surgical access to these sites is difficult, and a noninvasive approach could reduce surgical damage seen along the needle tract while providing spatial selectivity.

To establish the feasibility of intersectional ATAC in a CRE mouse line, FUS-BBBO was used to spatially target CRE-dependent DIO-Syn1-hM3Dq-mCherry encoded in AAV9 to the midbrain on a single side of the brain (FIG. 6, panel a), then tested the ability to activate TH-positive neurons in this region with CNO by imaging c-Fos accumulation (FIG. 6, panel b). FUS-BBBO applied to the midbrain resulted in BBB opening that partially overlapped with the expected location of the SNc/VTA (FIG. 6, panel c). Subsequent immunofluorescent imaging of brain sections revealed hM3Dq was present in the SNc/VTA region at the FUS-BBBO site (FIG. 6, panel d-e), and not at the contralateral site, or in the DRG (FIG. 11). The functionality of the DREADD receptor was then tested by staining for c-Fos positive nuclei at the site of FUS-BBBO and the contralateral region. Among TH-positive neurons, it was found a 7.3-fold increase in activation on the side targeted by the ATAC treatment after CNO administration (FIG. 6, panel f; n=5 mice, p=0.0011, paired, two-tailed t-test). Since ligand-independent activity of DREADDs has recently been shown to be present in peripheral neurons c-Fos accumulation was also tested in the absence of CNO to evaluate this possibility in the experiments. No activation after saline administration was found (FIG. 12, n=4, p=0.26, paired, two-tailed, t-test). These results demonstrate spatially selective, CNO-dependent, intersectional neuromodulation in a CRE mouse line.

Example 6: Tolerability of ATAC by Brain Tissue

To confirm that ATAC treatment is well tolerated by brain tissue, hematoxylin-stained brain sections from 14 mice with a total of 84 FUS-BBBO sites were examined. Consistent with previous findings[107], the majority of these sites (71.4%) had normal histology (FIG. 13, panel a-b). In the remaining FUS-targeted sites we found small areas of apparent tissue damage with mean dimensions of 115 μm by 265 μm, which were not visible on sections ±300 μm away from the site (FIG. 13, panel b-c). The average calculated volume of these features was $0.0027 \pm 0.0007$ mm$^3$. This represents less than 0.1% of the typical FUS-BBBO site, which has a volume of $2.81 \pm 0.51$ mm$^3$ (average of n=7 sites quantified by MRI) and 0.01% of the mouse hippocampus (volume, 26 mm$^3$)[108]. By comparison, the volume of brain displaced during invasive viral injections using typical needle gauges (27-33 gauge) is 0.1-0.4 mm$^3$ (FIG. 13, panel d), resulting in damage still present 7 weeks after the injection (FIG. 13, panel e).

These results are consistent with the normal performance of ATAC-treated mice in behavioral tests and the ability of ATAC-treated regions to become chemogenetically activated and express c-Fos. In future translational studies, this safety profile could be further improved with feedback-controlled FUS-BBBO[109].

In summary, provided herein are methods, systems, and related compounds, vectors and compositions allowing for noninvasive control of neural circuits. In particular, the methods and systems herein described utilize acoustically targeted chemogenetics to achieve a noninvasive neuromodulation in specifically selected cell-types among spatially selected brain regions.

In particular, according to a first aspect a method is described to control a target brain cell activity with respect to a target neural circuit of an individual, the method comprising applying focused ultrasound to a target brain region of the individual the target brain region comprising the target brain cell, and systemically administering to the individual an effective amount of microbubble contrast agents, the applying focused ultrasound and the systematically administering microbubble contrast agent is performed to induce transient blood-brain barrier opening at the target brain region.

before, simultaneously, in combination with or after applying focused ultrasound, systemically administering to the individual an effective amount of an expression vector configured to enter the brain at the transient blood-brain barrier opening and to specifically deliver and express in the target brain cell a gene encoding a chemogenetic protein under control of a promoter configured to be active in the target brain cell, the chemogenetic protein configured to activate or inhibit the target brain cell activity following binding with a corresponding chemical actuator or metabolite thereof.

the applying, the systemically administering an effective amount of microbubble contrast agents and the systemically administering an effective amount of an expression vector, performed to deliver and express the gene encoding a chemogenetic protein in a controlled percentage population of the target brain cell in the target brain region to obtain a chemogenetically treated target brain region in which target brain cells of the controlled percentage population comprise the chemogenetic protein and systemically administering to the individual the corresponding chemical actuator, to allow binding of the corresponding chemical actuator or a metabolite thereof with the chemogenetic protein in the target brain cells of the controlled population of the chemogenetically treated target brain region, and activation or inhibition of the target brain cell activity.

According the first set aspect, a system is also described to control a target brain cell activity with respect to a neural circuit, the system comprising:

an expression vector configured to enter the brain at the transient blood-brain barrier opening and to specifically deliver and express in the target brain cell a gene encoding a chemogenetic protein under control of a promoter configured to be active in the target brain cell, the chemogenetic protein configured to activate or inhibit the target brain cell activity following binding with a corresponding chemical actuator or metabolite thereof.

the corresponding chemical actuator configured to directly or indirectly convert the chemogenetic protein in an operative state; and a microbubble contrast agent for simultaneous combined or sequential use in the method of any one of the embodiments of the method according to the first aspect.

According to a second aspect, a method is described to modify a target behavior or physiological function of an individual associated with a target brain cell activity with respect to a neural circuit of the individual, the method comprising applying focused ultrasound to a target brain region of the individual the target brain region comprising the target brain cell, and systemically administering to the individual an effective amount of microbubble contrast agents, the applying focused ultrasound and the systematically administering microbubble contrast agent is performed to induce transient blood-brain barrier opening at the target brain region.

before, simultaneously, in combination with or after applying focused ultrasound, systemically administering to the individual an effective amount of an expression vector configured to enter the brain at the transient blood-brain barrier opening and to specifically deliver and express in the target brain cells a gene encoding a chemogenetic protein under control of a promoter configured to be active in the target brain cell, the chemogenetic protein configured to activate or inhibit the target brain cell activity following binding with a corresponding chemical actuator or metabolite thereof to modify the target behavior or physiological function of an individual the systemically administering an effective amount of a microbubble contrast agent and the systemically administering an effective amount of an expression vector are performed to deliver and express the gene encoding a chemogenetic protein in a controlled percentage population of the target brain cell in the target brain region associate with the target behavior or physiological function, and to obtain a chemogenetically treated target brain region in which the controlled percentage population of the target brain cell comprises the chemogenetic protein;

systemically administering to the individual the corresponding chemical actuator, to allow binding of the corresponding chemical actuator or a metabolite thereof with the chemogenetic protein in the controlled percentage population of the target brain cell of the chemogenetically treated target brain region, to modify the target behavior or physiological function of the individual.

According the second set aspect, a system is also described to modify a target behavior or physiological function of an individual associated with a target brain cell activity with respect to a neural circuit of the individual, the system comprising an expression vector configured to enter the brain at a transient blood-brain barrier opening and to specifically deliver and express in the target brain cells a gene encoding the chemogenetic protein under control of a promoter configured to be active in the target brain cell, a chemical actuator configured to activate the chemogenetic protein through direct binding to the chemogenetic protein of the chemical actuator or of a metabolite thereof, and the microbubble contrast agent for simultaneous, combined or sequential use in the method to modify a target behavior or physiological function of an individual according to any one of the embodiments of the method according to the second aspect.

According to a third aspect a method is described for treating or preventing in an individual a condition associated with a target brain cell activity with respect to a neural circuit of the individual, the method comprises applying focused ultrasound to a target brain region of the individual the target brain region comprising the target brain cell, and systemically administering to the individual an effective amount of microbubble contrast agents, the applying focused ultrasound and the systematically administering microbubble contrast agent is performed to induce transient blood-brain barrier opening at the target brain region.

before, simultaneously, in combination with or after applying focused ultrasound, systemically administering to the individual an effective amount of an expression vector configured to enter the brain at the transient blood-brain barrier opening and to specifically deliver and express in the target brain cells a gene encoding a chemogenetic protein under control of a promoter configured to be active in the target brain cell, the chemogenetic protein configured to activate or inhibit the target brain cell activity following binding with a corresponding chemical actuator or metabolite thereof to treat or prevent the condition in the individual;

the applying, the systemically administering an effective amount of microbubble contrast agents and the systemically administering an effective amount of an expression vector are performed to deliver and express the gene encoding a chemogenetic protein in a controlled percentage population of the target brain cell in the target brain region, the controlled percentage population associated with the treating or preventing of the condition in the individual, and to obtain a chemogenetically treated target brain region in which target brain cells of the controlled percentage population comprise the chemogenetic protein;

systemically administering to the individual the corresponding chemical actuator, to allow binding of the corresponding chemical actuator or a metabolite thereof with the chemogenetic protein in the target brain cells of the controlled population of the chemogenetically treated target brain region, thus treating or preventing the condition in the individual.

According the third set aspect, a system is also described to for treating or preventing in an individual a condition associated with a target brain cell activity with respect to a neural circuit of the individual, the method comprises a pharmaceutical composition comprising the expression vector configured to express the gene encoding for the chemogenetic protein in a target brain cell and a pharmaceutically acceptable vehicle.

a pharmaceutical composition comprising a chemical actuator configured to activate the chemogenetic protein through direct binding to the chemogenetic protein of the chemical actuator or of a metabolite thereof, for combined or sequential use in the method to treat or prevent in an individual a neurological condition according to any one of the embodiments of the method according to the second aspect.

In a first set of embodiments of the first, second and third aspect, the controlled percentage population is at least 20% of the target brain cell of the target brain region, preferably at least 40% of the target brain cell of the target brain region, more preferably at least 50% of the target brain cell of the target brain region.

In a second set of embodiments of the first, second and third aspect possibly including the first set of embodiments, the systemically administering an effective amount of microbubble contrast agents, the systemically administering an effective amount of an expression vector and/or the systemically administering to the individual the corresponding chemical actuator, is performed by intravenous injection.

In a third set of embodiments of the first, second and third aspect possibly including the first and/or the second set of embodiments, the applying focused ultrasound is performed at a frequency of 100 kHz to 100 MHz.

In a fourth set of embodiments of the first, second and third aspect possibly including the first and/or the second set of embodiments, the applying focused ultrasound is performed at a frequency of 0.2 to 1.5 mHz.

In a fifth set of embodiments of the first, second and third aspect possibly including the first and/or the second set of embodiments, the applying focused ultrasound is performed within an ultrasound having a mechanical index in a range between 0.2 and 0.6.

In a sixth set of embodiments of the first, second and third aspect possibly including any one of the first to the fifth set of embodiments, the expression vector is a viral vector. In some embodiments of the sixth set of embodiments, the expression vector is selected from the group consisting of AAV1, AAV2, AAV3, AAV5, AAV6, AAV7, AAV8, AAV9, AAV11, and AAV-DJ.

In a seventh set of embodiments of the first, second and third aspect possibly including any one of the first to the sixth set of embodiments, the chemogenetic protein is DREADD, PSAM, and/or TrpV1. In some embodiments of the seventh set of embodiments the chemogenetic protein is selected from the group consisting of hM2Di, hM4Di, hM1Dq, hM3Dq and hM5Dq.

In an eighth set of embodiments of the first, second and third aspect possibly including any one of the first to the seventh set of embodiments, the chemical actuator is selected from clozapine-N-oxide, clozapine, compound 21, and perlapine.

In a ninth set of embodiments of the first, second and third aspect possibly including any one of the first to the eighth set of embodiments, the target region has a size in a range between 1 and 10 mm.

In a tenth set of embodiments of the first, second and third aspect possibly including any one of the first to the ninth set of embodiments, the target region is selected from the group consisting of hippocampus, basal ganglia, arcuate nucleus, dorsal striatum, thalamus, medial prefrontal complex, and dorsal palidum.

In an eleventh set of embodiments of the first, second and third aspect possibly including any one of the first to the tenth set of embodiments, the microbubble has an average diameter between 1 and 5 microns. In first subset of embodiments of the eleventh set of embodiments the microbubble contrast agent is in a concentration of 1.2E7-1.2E9 per kg of body weight of the individual. In a second subset of embodiment of the eleventh set of embodiments possibly comprising the first subset of embodiment of the eleventh set of embodiments, the administering of the microbubble contrast agent is performed in combination with the administering the expression vectors.

In a twelfth set of embodiments of the first, second and third aspect possibly including any one of the first to the eleventh set of embodiments, the expression vector is in a concentration between 2E13-2E14 viral particles per kilogram of body weight of the subject.

In an thirteenth set of embodiments of the first, second and third aspect possibly including any one of the first to the twelfth set of embodiments, the administering of the chemical actuator is performed at least one week after the administrating of the expression vector and the applying of focused ultrasound.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art upon the reading of the present disclosure, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all sub-ranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which are not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Sakurai, T., *The role of orexin in motivated behaviours*. Nature Reviews Neuroscience, 2014.
2. Russo, S. J. and E. J. Nestler, *The brain reward circuitry in mood disorders*. Nature Reviews Neuroscience, 2013. 14(9): p. 609-625.
3. Apkarian, A. V., J. A. Hashmi, and M. N. Baliki, *Pain and the brain: specificity and plasticity of the brain in clinical chronic pain*. Pain, 2011. 152(3 Suppl): p. S49.
4. Shin, L. M. and I. Liberzon, *The neurocircuitry of fear, stress, and anxiety disorders*. Neuropsychopharmacology, 2009. 35(1): p. 169-191.
5. Koob, G. F. and N. D. Volkow, *Neurocircuitry of addiction*. Neuropsychopharmacology, 2009. 35(1): p. 217-238.
6. Eldridge, M. A. G., et al., *Chemogenetic disconnection of monkey orbitofrontal and rhinal cortex reversibly disrupts reward value*. Nature Neuroscience, 2015. 19: p. 37.
7. Thomsen, G. M., et al., *Delayed Disease Onset and Extended Survival in the SOD1(G93A) Rat Model of Amyotrophic Lateral Sclerosis after Suppression of Mutant SOD1 in the Motor Cortex*. The Journal of Neuroscience, 2014. 34(47): p. 15587-15600.
8. Akil, H., et al., *The Future of Psychiatric Research: Genomes and Neural Circuits*. Science, 2010. 327(5973): p. 1580.
9. Ressler, K. J. and H. S. Mayberg, *Targeting abnormal neural circuits in mood and anxiety disorders: from the laboratory to the clinic*. Nature Neuroscience, 2007. 10: p. 1116.
10. Tye, K. M. and K. Deisseroth, *Optogenetic investigation of neural circuits underlying brain disease in animal models*. Nature Reviews Neuroscience, 2012. 13: p. 251.
11. Szablowski, J. O., et al., *Acoustically targeted chemogenetics for the non-invasive control of neural circuits*. Nature Biomedical Engineering, 2018. 2(7): p. 475-484.
12. Betke, K. M., C. A. Wells, and H. E. Hamm, *GPCR mediated regulation of synaptic transmission*. Progress in neurobiology, 2012. 96(3): p. 304-321.
13. Slimko, E. M., et al., *Selective electrical silencing of mammalian neurons in vitro by the use of invertebrate ligand-gated chloride channels*. J Neurosci, 2002. 22(17): p. 7373-9.
14. Gossen, M. and H. Bujard, *Tight control of gene expression in mammalian cells by tetracycline-responsive promoters*. Proc Natl Acad Sci USA, 1992. 89(12): p. 5547-51.
15. !!! INVALID CITATION !!!
16. Banks, W. A., *Characteristics of compounds that cross the blood-brain barrier*. BMC neurology, 2009. 9 Suppl 1(Suppl 1): p. S3-S3.
17. Pardridge, W. M., *Drug transport across the blood-brain barrier*. Journal of cerebral blood flow and metabolism: official journal of the International Society of Cerebral Blood Flow and Metabolism, 2012. 32(11): p. 1959-1972.
18. Pardridge, W. M., *The blood-brain barrier: bottleneck in brain drug development*. NeuroRx: the journal of the American Society for Experimental NeuroTherapeutics, 2005. 2(1): p. 3-14.
19. Banks, W. A., *Peptides and the blood-brain barrier*. Peptides, 2015. 72: p. 16-19.
20. Adkison, K. D. and D. D. Shen, *Uptake of valproic acid into rat brain is mediated by a medium-chain fatty acid transporter*. Journal of Pharmacology and Experimental Therapeutics, 1996. 276(3): p. 1189.
21. Barar, J., et al., *Blood-brain barrier transport machineries and targeted therapy of brain diseases*. BioImpacts: BI, 2016. 6(4): p. 225-248.
22. Tinberg, C. E., et al., *Computational design of ligand-binding proteins with high affinity and selectivity*. Nature, 2013. 501(7466): p. 212-216.
23. Pardridge, W. M., *Drug transport across the blood-brain barrier*. J Cereb Blood Flow Metab, 2012. 32(11): p. 1959-72.
24. English, J. G. and B. L. Roth, *Chemogenetics—a transformational and translational platform*. JAMANeurology, 2015. 72(11): p. 1361-1366.
25. Smith, K. S., et al., *DREADDs: Use and Application in Behavioral Neuroscience*. Behavioral neuroscience, 2016. 130(2): p. 137-155.
26. Roth, B. L., *DREADDs for Neuroscientists*. Neuron, 2016. 89(4): p. 683-94.
27. Alexander, G. M., et al., *Remote control of neuronal activity in transgenic mice expressing evolved G protein-coupled receptors*. Neuron, 2009. 63(1): p. 27-39.
28. Armbruster, B. N., et al., *Evolving the lock to fit the key to create a family of G protein-coupled receptors potently activated by an inert ligand*. Proc Natl Acad Sci USA, 2007. 104(12): p. 5163-8.
29. al., K. J. T.e., *DREADD Agonist 21 Is an Effective Agonist for Muscarinic-Based DREADDs in Vitro and in Vivo*. ACS Pharmacol. Transl. Sci., 2018. 1(1): p. 12.
30. Magnus, C. J., et al., *Chemical and genetic engineering of selective ligand-ion channel interactions*. Science (New York, N.Y.), 2011. 333(6047): p. 1292-1296.

31. Carpentier, A., et al., *Clinical trial of blood-brain barrier disruption by pulsed ultrasound*. Sci Transl Med, 2016. 8(343): p. 343re2.
32. Sheikov, N., et al., *Cellular mechanisms of the blood-brain barrier opening induced by ultrasound in presence of microbubbles*. Ultrasound Med Biol, 2004. 30(7): p. 979-89.
33. Wang, D. S., et al., *Cationic versus neutral microbubbles for ultrasound-mediated gene delivery in cancer*. Radiology, 2012. 264(3): p. 721-732.
34. Huang, Q., et al., *Effective Gene Transfer into Central Nervous System Following Ultrasound-Microbubbles-Induced Opening of the Blood-Brain Barrier*. Ultrasound in Medicine & Biology, 2012. 38(7): p. 1234-1243.
35. Ginn, S. L., et al., *Gene therapy clinical trials worldwide to 2012 an update*. Journal of Gene Medicine, 2013. 15(2): p. 65-77.
36. Mendell, J. R., et al., *Single-Dose Gene Replacement Therapy for Spinal Muscular Atrophy*. New England Journal of Medicine, 2017. 377(18): p. 1713-1722.
37. Rangarajan, S., et al., *AAV5-Factor VIII Gene Transfer in Severe Hemophilia A*. New England Journal of Medicine, 2017.
38. Bender, E., *Gene therapy: Industrial strength*. Nature, 2016. 537: p. S57.
39. Kotterman, M. A., T. W. Chalberg, and D. V. Schaffer, *Viral Vectors for Gene Therapy: Translational and Clinical Outlook*. Annu Rev Biomed Eng, 2015. 17: p. 63-89.
40. Russell, S., et al., *Efficacy and safety of voretigene neparvovec (AAV2-hRPE65v2) in patients with RPE65-mediated inherited retinal dystrophy: a randomised, controlled, open-label, phase 3 trial*. Lancet, 2017. 390(10097): p. 849-860.
41. Rangarajan, S., et al., *AAV5-Factor VIII Gene Transfer in Severe Hemophilia A*. New England Journal of Medicine, 2017. 377(26): p. 2519-2530.
42. Deverman, B E, et al., *Cre-dependent selection yields AAV variants for widespread gene transfer to the adult brain*. Nat Biotechnol, 2016. 34(2): p. 204-9.
43. Watakabe, A., et al., *Comparative analyses of adeno-associated viral vector serotypes 1, 2, 5, 8 and 9 in marmoset, mouse and macaque cerebral cortex*. Neuroscience Research, 2015. 93: p. 144-157.
44. Aschauer, D. F., S. Kreuz, and S. Rumpel, *Analysis of transduction efficiency, tropism and axonal transport of AAV serotypes 1, 2, 5, 6, 8 and 9 in the mouse brain*. PLoS One, 2013. 8(9): p. e76310.
45. Heffner, C. S., et al., *Supporting conditional mouse mutagenesis with a comprehensive cre characterization resource*. Nat Commun, 2012. 3: p. 1218.
46. Gomez, J. L., et al., *Chemogenetics revealed: DREADD occupancy and activation via converted clozapine*. Science, 2017. 357(6350): p. 503.
47. Lambert, D. G., *Drugs and receptors*. Continuing Education in Anaesthesia Critical Care & Pain, 2004. 4(6): p. 181-184.
48. Camerino, D. C., D. Tricarico, and J. F. Desaphy, *Ion channel pharmacology*. Neurotherapeutics, 2007. 4(2): p. 184-98.
49. Hirtz, D., et al., *How common are the "common" neurologic disorders?* Neurology, 2007. 68(5): p. 326-37.
50. Pangalos, M. N., L. E. Schechter, and O. Hurko, *Drug development for CNS disorders: strategies for balancing risk and reducing attrition*. Nat Rev Drug Discov, 2007. 6(7): p. 521-32.
51. National-Institutes-of-Mental-Health, *The Numbers Count: Mental Disorders in America*.
52. Plummer, C., A. S. Harvey, and M. Cook, *EEG source localization in focal epilepsy: where are we now?* Epilepsia, 2008. 49(2): p. 201-18.
53. Cendes, F., et al., *Neuroimaging of epilepsy*. Handbook of clinical neurology, 2016. 136: p. 985-1014.
54. Libby, L. A. and J. D. Ragland, *FMRI as a measure of cognition related brain circuitry in schizophrenia*. Current topics in behavioral neurosciences, 2012. 11: p. 253-267.
55. Duyn, J. and A. P. Koretsky, *Magnetic resonance imaging of neural circuits*. Nature clinical practice. Cardiovascular medicine, 2008. 5 Suppl 2(Suppl 2): p. S71-S78.
56. Wang, K. S., D. V. Smith, and M. R. Delgado, *Using fMRI to study reward processing in humans: past, present, and future*. Journal of neurophysiology, 2016. 115(3): p. 1664-1678.
57. Bernal-Casas, D., et al., *Studying Brain Circuit Function with Dynamic Causal Modeling for Optogenetic fMRI*. Neuron, 2017. 93(3): p. 522-532.e5.
58. Tufail, Y, et al., *Transcranial pulsed ultrasound stimulates intact brain circuits*. Neuron, 2010. 66(5): p. 681-694.
59. King, R. L., et al., *Effective parameters for ultrasound-induced in vivo neurostimulation*. Ultrasound in medicine & biology, 2013. 39(2): p. 312-331.
60. Deffieux, T., et al., *Low-intensity focused ultrasound modulates monkey visuomotor behavior*. Current Biology, 2013. 23(23): p. 2430-2433.
61. LANDHUIS, E., *Ultrasound for the brain*. Nature 2017. 551: p. 257-259.
62. Airan, R D., et al., *Noninvasive Targeted Transcranial Neuromodulation via Focused Ultrasound Gated Drug Release from Nanoemulsions*. Nano Letters, 2017. 17(2): p. 652-659.
63. Sato, T., M. Shapiro, and D. Tsao, *Ultrasonic Neuromodulation Causes Widespread Cortical Activation via an Indirect Auditory Mechanism*. bioRxiv, 2017.
64. McDannold, N., et al., *Targeted, noninvasive blockade of cortical neuronal activity*. Scientific reports, 2015. 5.
65. Mehić, E., et al., *Increased anatomical specificity of neuromodulation via modulated focused ultrasound*. PLoS One, 2014. 9(2): p. e86939.
66. Tyler, W. J., S. W. Lani, and G. M. Hwang, *Ultrasonic modulation of neural circuit activity*. Current Opinion in Neurobiology, 2018. 50: p. 222-231.
67. Leinenga, G. and J. Gotz, *Scanning ultrasound removes amyloid-beta and restores memory in an Alzheimer's disease mouse model*. Sci Transl Med, 2015. 7(278): p. 278ra33.
68. Burgess, A., et al., *Alzheimer disease in a mouse model: MR imaging-guided focused ultrasound targeted to the hippocampus opens the blood-brain barrier and improves pathologic abnormalities and behavior*. Radiology, 2014. 273(3): p. 736-45.
69. Chen, H. and E. E. Konofagou, *The size of blood-brain barrier opening induced by focused ultrasound is dictated by the acoustic pressure*. Journal of Cerebral Blood Flow & Metabolism, 2014. 34(7): p. 1197-1204.
70. Alonso, A., et al., *Focal Delivery of AAV2/1-transgenes Into the Rat Brain by Localized Ultrasound-induced BBB Opening*. Molecular therapy. Nucleic acids, 2013. 2(2): p. e73-e73.
71. Thévenot, E., et al., *Targeted delivery of self-complementary adeno-associated virus serotype 9 to the brain, using magnetic resonance imaging-guided focused ultrasound*. Human gene therapy, 2012. 23(11): p. 1144-1155.

72. Wang, S., et al., *Non-invasive, Focused Ultrasound-Facilitated Gene Delivery for Optogenetics*. Scientific Reports, 2017. 7: p. 39955.
73. Wang, S., et al., *Noninvasive, neuron-specific gene therapy can be facilitated by focused ultrasound and recombinant adeno-associated virus*. Gene therapy, 2015. 22(1): p. 104-110.
74. Hsu, P.-H., et al., *Noninvasive and Targeted Gene Delivery into the Brain Using Microbubble-Facilitated Focused Ultrasound*. PLOS ONE, 2013. 8(2): p. e57682.
75. Song, K. H., et al., *Microbubble gas volume: A unifying dose parameter in blood-brain barrier opening by focused ultrasound*. Theranostics, 2017. 7(1): p. 144-152.
76. Lindeberg, J., et al., *Transgenic expression of Cre recombinase from the tyrosine hydroxylase locus*. Genesis, 2004. 40(2): p. 67-73.
77. Wang, S., et al., *Microbubble Type and Distribution Dependence of Focused Ultrasound Induced Blood Brain Barrier Opening*. Ultrasound in medicine & biology, 2014. 40(1): p. 130-137.
78. Thevenot, E., et al., *Targeted delivery of self-complementary adeno-associated virus serotype 9 to the brain, using magnetic resonance imaging-guided focused ultrasound*. Hum Gene Ther, 2012. 23(11): p. 1144-55.
79. Choi, J. J., et al., *Noninvasive and localized neuronal delivery using short ultrasonic pulses and microbubbles*. Proceedings of the National Academy of Sciences, 2011. 108(40): p. 16539.
80. Choi, J. J., et al., *Noninvasive, transcranial and localized opening of the blood-brain barrier using focused ultrasound in mice*. Ultrasound Med Biol, 2007. 33(1): p. 95-104.
81. Zhu, H., et al., *Chemogenetic inactivation of ventral hippocampal glutamatergic neurons disrupts consolidation of contextual fear memory*. Neuropsychopharmacology, 2014. 39(8): p. 1880-92.
82. Lein, E. S., et al., *Genome-wide atlas of gene expression in the adult mouse brain*. Nature, 2007. 445(7124): p. 168-76.
83. Grippo, R. M., et al., *Direct Midbrain Dopamine Input to the Suprachiasmatic Nucleus Accelerates Circadian Entrainment*. Curr Biol, 2017. 27(16): p. 2465-2475.e3.
84. Koch, M., et al., *Hypothalamic POMC neurons promote cannabinoid-induced feeding*. Nature, 2015. 519(7541): p. 45-50.
85. Zincarelli, C., et al., *Analysis of AAV Serotypes 1-9 Mediated Gene Expression and Tropism in Mice After Systemic Injection*. Molecular Therapy, 2008. 16(6): p. 1073-1080.
86. Mahler, S. V., et al., *Designer receptors show role for ventral pallidum input to ventral tegmental area in cocaine seeking*. 2014. 17(4): p. 577-85.
87. Eliava, M., et al., *A New Population of Parvocellular Oxytocin Neurons Controlling Magnocellular Neuron Activity and Inflammatory Pain Processing*. Neuron, 2016. 89(6): p. 1291-1304.
88. Alexander, G. M., et al., *Remote control of neuronal activity in transgenic mice expressing evolved G protein-coupled receptors*. Neuron, 2009. 63(1): p. 27-39.
89. Sananbenesi, F., et al., *A hippocampal Cdk5 pathway regulates extinction of contextual fear*. Nat Neurosci, 2007. 10(8): p. 1012-9.
90. Kim, K M., et al., *Optogenetic mimicry of the transient activation of dopamine neurons by natural reward is sufficient for operant reinforcement*. PLoS One, 2012. 7(4): p. e33612.
91. DiMattia, M. A., et al., *Structural Insight into the Unique Properties of Adeno-Associated Virus Serotype 9*. Journal of Virology, 2012. 86(12): p. 6947-6958.
92. Tarini, M., P. Cignoni, and C. Montani, *Ambient occlusion and edge cueing to enhance real time molecular visualization*. Ieee Transactions on Visualization and Computer Graphics, 2006. 12(5): p. 1237-1244.
93. Majka, P., et al., *Common atlas format and 3D brain atlas reconstructor: infrastructure for constructing 3D brain atlases*. Neuroinformatics, 2012. 10(2): p. 181-97.
94. Johnson, G. A., et al., *Waxholm space: an image-based reference for coordinating mouse brain research*. Neuroimage, 2010. 53(2): p. 365-72.
95. Andersen, P., *The hippocampus book*. 2007, Oxford; New York: Oxford University Press. xx, 832 p.
96. Castle, M. J., et al., *Controlling AAV Tropism in the Nervous System with Natural and Engineered Capsids*. Methods Mol Biol, 2016. 1382: p. 133-49.
97. Dittgen, T., et al., *Lentivirus-based genetic manipulations of cortical neurons and their optical and electrophysiological monitoring in vivo*. Proc Natl Acad Sci USA, 2004. 101(52): p. 18206-11.
98. Chan, K. Y., et al., *Engineered AAVs for efficient noninvasive gene delivery to the central and peripheral nervous systems*. Nat Neurosci, 2017. 20(8): p. 1172-1179.
99. Whitaker, A. M., N. W. Gilpin, and S. Edwards, *Animal models of post-traumatic stress disorder and recent neurobiological insights*. Behav Pharmacol, 2014. 25(5-6): p. 398-409.
100. VanElzakker, M. B., et al., *From Pavlov to PTSD: the extinction of conditioned fear in rodents, humans, and anxiety disorders*. Neurobiol Learn Mem, 2014. 113: p. 3-18.
101. Kheirbek, M. A., et al., *Differential control of learning and anxiety along the dorsoventral axis of the dentate gyrus*. Neuron, 2013. 77(5): p. 955-68.
102. Blanchard, D. C. and R. J. Blanchard, *Ethoexperimental approaches to the biology of emotion*. Annu Rev Psychol, 1988. 39: p. 43-68.
103. Burgess, A., et al., *Therapeutic effects of focused ultrasound-mediated blood-brain barrier opening in a mouse model of Alzheimer's disease*. Journal of Therapeutic Ultrasound, 2015. 3(Suppl 1): p. 016-016.
104. Mooney, S. J., et al., *Focused Ultrasound-Induced Neurogenesis Requires an Increase in Blood-Brain Barrier Permeability*. PLoS One, 2016. 11(7): p. e0159892.
105. Luo, L., E. M. Callaway, and K. Svoboda, *Genetic Dissection of Neural Circuits*. Neuron, 2008. 57(5): p. 634-660.
106. Chen, R., et al., *Wireless magnetothermal deep brain stimulation*. Science, 2015. 347(6229): p. 1477-80.
107. Baseri, B., et al., *Multi-modality safety assessment of blood-brain barrier opening using focused ultrasound and definity microbubbles: a short-term study*. Ultrasound Med Biol, 2010. 36(9): p. 1445-59.
108. Badea, A., A. A. Ali-Sharief, and G. A. Johnson, *Morphometric analysis of the C57BL/6J mouse brain*. Neuroimage, 2007. 37(3): p. 683-93.
109. Tung, Y. S., et al., *In vivo transcranial cavitation threshold detection during ultrasound-induced blood-brain barrier opening in mice*. Phys Med Biol, 2010. 55(20): p. 6141-55.

The invention claimed is:

1. A method to perform a cell-specific control of activity of a target brain cell with respect to a target neural circuit of an individual, the method comprising:

(i) applying focused ultrasound to a target brain region of the individual at a mechanical index of 0.2 to 0.6 with a pulse duration of 1 to 10 ms, the target brain region comprising the target brain cell;

(ii) systemically administering to the individual an effective amount of microbubble contrast agents in an amount from 1.2E7 to 1.2E9 per kg of the individual; wherein the applying focused ultrasound and the systematically administering microbubble contrast agent are performed to induce transient blood-brain barrier opening at the target brain region;

the method further comprising (iii) systemically administering to the individual an effective amount, from 4E13 to 2E14 viral particles per kg of the individual, of an adenoassociated viral (AAV) expression vector configured to enter the brain at the transient blood-brain barrier opening and to specifically deliver and express in the target brain cell a gene encoding a chemogenetic protein under control of a cell-type specific promoter configured to be cell-type specifically active in the target brain cell, wherein the chemogenetic protein is configured to activate or inhibit the target brain cell activity following binding with a corresponding chemical actuator or metabolite thereof, the applying, the systemically administering an effective amount of microbubble contrast agents, and the systemically administering an effective amount of an expression vector, are performed in combination to specifically deliver and cell-type specifically express the gene encoding a chemogenetic protein in a controlled percentage population—of at least 20% of target brain cells in the target brain region to obtain a chemogenetically treated target brain region in which the target brain cells of the controlled percentage population comprise the chemogenetic protein; and the systemically administering of an expression vector is performed in combination with, the applying focused ultrasound, and the systematically administering microbubble contrast agent to have vectors carrying genetic material in blood concurrently with the occurrence of the transient blood-brain barrier opening;

the method further comprising (iv) systemically administering to the individual the corresponding chemical actuator or a metabolite thereof, to allow binding of the corresponding chemical actuator or a metabolite thereof with the chemogenetic protein in the target brain cells of the controlled population of the chemogenetically treated target brain region, and activation or inhibition of the target brain cell activity wherein the AAV expression vector comprises a vector regulatory region in series with a target brain cell regulatory region in a configuration in which expression of the gene encoding the chemogenetic protein is performed in presence and activity of both the vector regulatory regions and the target brain cell regulatory region independently activated or repressed in temporal succession, and wherein the target brain region is less than 1 mm in size.

2. The method of claim 1, wherein the controlled percentage population is at least 40% of the target brain cells of the target brain region.

3. The method of claim 1, wherein the controlled percentage population is at least 50% of the target brain cells of the target brain region.

4. The method of claim 1, wherein the systemically administering an effective amount of a microbubble contrast agent, the systemically administering an effective amount of an expression vector and/or the systemically administering to the individual the corresponding chemical actuator, is performed by intravenous injection.

5. The method of claim 1, wherein the applying focused ultrasound is performed at a frequency of 100 kHz to 100 MHz.

6. The method of claim 1, wherein the applying focused ultrasound is performed at a frequency of 0.2 to 1.5 MHz.

7. The method of claim 1, wherein the applying focused ultrasound is performed within an ultrasound having a mechanical index in a range between 0.2 and 0.6.

8. The method of claim 1, wherein the expression vector is selected from the group consisting of AAV1, AAV2, AAV3, AAV5, AAV6, AAV7, AAV8, AAV9, AAV11, and AAV-DJ.

9. The method of claim 1, wherein the chemogenetic protein is DREADD, PSAM, and/or TrpV1.

10. The method of claim 9, wherein the chemogenetic protein is selected from the group consisting of hM2Di, hM4Di, hM1 Dq, hM3Dq and hM5Dq.

11. The method of claim 1, wherein the chemical actuator is selected from clozapine-N-oxide, clozapine, compound 21, and perlapine.

12. The method of claim 1, wherein the target region is selected from the group consisting of hippocampus, basal ganglia, arcuate nucleus, dorsal striatum, thalamus, medial prefrontal complex, and dorsal pallidum.

13. The method of claim 1, wherein the microbubble has an average dimeter between 1 and 5 microns.

14. The method of claim 1, the administering of the microbubble contrast agent is performed simultaneously with the administering the expression vectors.

15. The method of claim 1, wherein the administering of the chemical actuator is performed at least one week after the administrating of the expression vector and the applying of focused ultrasound.

16. A method to modify a target behavior or physiological function of an individual associated with activity of a target brain cell with respect to a neural circuit of the individual, the method comprising (i) applying focused ultrasound to a target brain region of the individual at a mechanical index of 0.2 to 0.6, with a pulse duration of 1 to 10 ms, the target brain region comprising the target brain cell (ii) systemically administering to the individual an effective amount of microbubble contrast agents in an amount from 1.2E7 to 1.2E9 per kg of the individual; wherein the applying focused ultrasound and the systematically administering microbubble contrast agent are performed to induce transient blood-brain barrier opening at the target brain region;

the method further comprising (iii) systemically administering to the individual an effective amount, from 4E13 to 2E14 viral particles per kg of the individual, of an of an adenoassociated viral (AAV) expression vector configured to enter the brain at the transient blood-brain barrier opening and to specifically deliver and express in the target brain cells a gene encoding a chemogenetic protein under control of a cell-type specific promoter configured to be cell-type specifically active in the target brain cell, wherein the chemogenetic protein configured to activate or inhibit the target brain cell activity following binding with a corresponding chemical actuator or metabolite thereof to modify the target behavior or physiological function of an individual, the applying, the systemically administering an effective amount of a microbubble contrast agent and the systemically administering an effective amount of an expression vector are performed in combination to specifically deliver and cell-type specifically express the gene encoding a chemogenetic protein in a controlled percentage population of at least 20% of target brain cells in the target brain region associated with the target behavior or physiological function, and to obtain a chemogenetically treated target brain region in which the controlled percentage population of the target brain cells comprises the chemogenetic protein; and the systemically administering of an expression vector is performed in combination with, the applying focused ultrasound, and the systematically administering microbubble contrast agent to have vectors carrying genetic material in blood concurrently with the occurrence of the transient blood-brain barrier opening;

the method further comprising (iv) systemically administering to the individual the corresponding chemical actuator or a metabolite thereof, to allow binding of the corresponding chemical actuator or a metabolite thereof with the chemogenetic protein in the controlled percentage population of the target brain cell of the chemogenetically treated target brain region, to modify the target behavior or physiological function of the individual wherein the AAV expression vector comprises a vector regulatory region in series with a target brain cell regulatory region in a configuration in which expression of the gene encoding the chemogenetic protein is performed in presence and activity of both the vector regulatory regions and the target brain cell regulatory region independently activated or repressed in temporal succession, and wherein the target brain region is less than 1 mm in size.

17. A method for treating or preventing in an individual a condition associated with an activity of a target brain cell with respect to a neural circuit of the individual, the method comprises (i) applying focused ultrasound to a target brain region of the individual at a mechanical index of 0.2 to 0.6, with a pulse duration of 1 to 10 ms, the target brain region comprising the target brain cell (ii) systemically administering to the individual an effective amount of microbubble contrast agents in an amount from 1.2E7 to 1.2E9 per kg of the individual; wherein the applying focused ultrasound and the systematically administering microbubble contrast agent are performed to induce transient blood-brain barrier opening at the target brain region;

the method further comprising (iii) systemically administering to the individual an effective amount, from 4E13 to 2E14 viral particles per kg of the individual, of an of an adenoassociated viral (AAV) expression vector configured to enter the brain at the transient blood-brain barrier opening and to specifically deliver and express in the target brain cells a gene encoding a chemogenetic protein under control of a cell-type specific promoter configured to be cell-type specifically active in the target brain cell, wherein the chemogenetic protein configured to activate or inhibit the target brain cell activity following binding with a corresponding chemical actuator or metabolite thereof to treat or prevent the condition in the individual;

the applying, the systemically administering an effective amount of microbubble contrast agents and the systemically administering an effective amount of an expression vector are performed in combination to specifically deliver and cell-type specifically express the gene encoding a chemogenetic protein in a controlled percentage population of at least 20% of target brain cells in the target brain region, the controlled percentage population associated with the treating or preventing of the condition in the individual, and to obtain a chemogenetically treated target brain region in which the target brain cells of the controlled percentage population comprise the chemogenetic protein; and the systemically administering of an expression vector is performed in combination with, the applying focused ultrasound, and the systematically administering microbubble contrast agent to have vectors carrying genetic material in blood concurrently with the occurrence of the transient blood-brain barrier opening;

the method further comprising (iv) systemically administering to the individual the corresponding chemical actuator or a metabolite thereof, to allow binding of the corresponding chemical actuator or a metabolite thereof with the chemogenetic protein in the target brain cells of the controlled population of the chemogenetically treated target brain region, thus treating or preventing the condition in the individual wherein the AAV expression vector comprises a vector regulatory region in series with a target brain cell regulatory region in a configuration in which expression of the gene encoding the chemogenetic protein is performed in presence and activity of both the vector regulatory regions and the target brain cell regulatory region independently activated or repressed in temporal succession, and wherein the target brain region is less than 1 mm in size.

18. The method of claim 17, wherein the controlled percentage population is at least 40% of the target brain cells of the target brain region.

19. The method of claim 17, wherein the controlled percentage population is at least 50% of the target brain cells of the target brain region.

* * * * *